(12) United States Patent
Nolte

(10) Patent No.: US 9,514,271 B2
(45) Date of Patent: Dec. 6, 2016

(54) DIGITAL HOLOGRAPHIC METHOD OF MEASURING CELLULAR ACTIVITY AND MEASURING APPARATUS WITH IMPROVED STABILITY

(75) Inventor: David D. Nolte, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 868 days.

(21) Appl. No.: 13/704,438

(22) PCT Filed: Jun. 17, 2011

(86) PCT No.: PCT/US2011/040959
§ 371 (c)(1),
(2), (4) Date: Dec. 14, 2012

(87) PCT Pub. No.: WO2011/160068
PCT Pub. Date: Dec. 22, 2011

(65) Prior Publication Data
US 2013/0088568 A1    Apr. 11, 2013

Related U.S. Application Data

(60) Provisional application No. 61/397,885, filed on Jun. 17, 2010.

(51) Int. Cl.
*G01B 9/02* (2006.01)
*G06F 19/10* (2011.01)
(Continued)

(52) U.S. Cl.
CPC ............. *G06F 19/10* (2013.01); *A61B 5/0075* (2013.01); *A61B 5/4845* (2013.01); *G01N 21/27* (2013.01);
(Continued)

(58) Field of Classification Search
CPC ............. G03H 1/0443; G03H 1/0866; G03H 2001/0447; G03H 1/32; G03H 2001/0467; G03H 2001/0445; G03H 2001/045; G01N 21/27; A61B 5/0075; G01B 9/02091

USPC ................................... 356/457, 73, 319, 458
See application file for complete search history.

(56) References Cited

U.S. PATENT DOCUMENTS 6,014,204 A * 1/2000 Prahl .................... G01N 21/474
356/446
6,053,613 A * 4/2000 Wei ....................... A61B 3/1005
351/205

(Continued)

FOREIGN PATENT DOCUMENTS

JP   2009-053578 A  *  3/2009
WO   WO2009111609 A2   9/2009
WO   WO 2012/005952 A2 *  1/2012

OTHER PUBLICATIONS

Lu et al. "Low sidelobe limited deffection opticalcoherence Tomagraphy" (2002).*

(Continued)

*Primary Examiner* — David Harvey
(74) *Attorney, Agent, or Firm* — Bose McKinney & Evans LLP

(57) ABSTRACT

Motility contrast imaging (MCI) is a depth-resolved holographic technique to extract cellular and subcellular motion inside tissue. The holographic basis of the measurement technique makes it highly susceptible to mechanical motion. The motility contrast application, in particular, preferably includes increased mechanical stability because the signal is based on time-varying changes caused by cellular motion, which should not be confused with mechanical motion of the system. Apparatus for motility contrast imaging that provides increased mechanical stability is disclosed. It is based on common-path configurations, in which the signal and reference beams share optical elements in their paths to the detector. The two beams share mechanical motions in common, and hence these motions do not contribute to the signal.

31 Claims, 85 Drawing Sheets

(51) Int. Cl.
*A61B 5/00* (2006.01)
*G03H 1/04* (2006.01)
*G01N 21/27* (2006.01)
G03H 1/08 (2006.01)
G03H 1/32 (2006.01)

(52) U.S. Cl.
CPC .......... *G03H 1/0443* (2013.01); *G03H 1/0866* (2013.01); *G03H 1/32* (2013.01); *G03H 2001/045* (2013.01); *G03H 2001/0445* (2013.01); *G03H 2001/0447* (2013.01); *G03H 2001/0467* (2013.01); *G03H 2222/24* (2013.01)

(56) References Cited

U.S. PATENT DOCUMENTS

| | | | | |
|---|---|---|---|---|
| 6,144,449 | A * | 11/2000 | Knuettel | G01N 21/4795 356/450 |
| 6,268,921 | B1 * | 7/2001 | Seitz | G01B 11/026 356/407 |
| 7,327,463 | B2 * | 2/2008 | Alphonse | A61B 5/0066 356/479 |
| 7,364,296 | B2 * | 4/2008 | Miller | A61B 3/102 351/206 |
| 7,474,407 | B2 * | 1/2009 | Gutin | A61B 5/0066 356/479 |
| 7,551,293 | B2 * | 6/2009 | Yelin | G01B 9/02027 356/456 |
| 8,379,218 | B2 * | 2/2013 | Deck | G01B 11/2441 356/479 |
| 8,508,746 | B2 * | 8/2013 | Wax | G01B 9/02057 356/244 |
| 2004/0089800 | A1 | 5/2004 | Jackman | |
| 2005/0121596 | A1 * | 6/2005 | Kam | G01N 21/6458 250/201.2 |
| 2007/0073156 | A1 | 3/2007 | Zilberman et al. | |
| 2007/0236687 | A1 * | 10/2007 | Mikuriya | G02B 21/245 356/153 |
| 2008/0018966 | A1 * | 1/2008 | Dubois | G01B 9/021 359/9 |
| 2008/0097183 | A1 | 4/2008 | Monro | |
| 2009/0073529 | A1 * | 3/2009 | Imai | G02B 5/189 359/204.1 |
| 2009/0221920 | A1 * | 9/2009 | Boppart | A61B 5/0066 600/476 |
| 2010/0065751 | A1 | 3/2010 | Harra et al. | |
| 2010/0141829 | A1 * | 6/2010 | Jalali | A61B 1/00009 348/370 |
| 2010/0141954 | A1 * | 6/2010 | Kobayashi | G01B 9/02007 356/479 |
| 2011/0096291 | A1 * | 4/2011 | Buckland | A61B 3/102 351/206 |

OTHER PUBLICATIONS

Jeong, et al., "Volumetric motility-contast imaging of tissue response to cytoskeletal anti-cancer drugs," Optics Express, Oct. 2007, entire document, retrieved from the internet: www.physics.purdue.edu/nlo/publication/JoengOE07.pdf/.

Dailey et al., "Confocal Microscopy of Living Cells," Handbook of Biological Confocal Microscopy, 3rd Ed. SpringerScience+Business Media, New York, 2006, entire document retrieved from the internet, www.3dcourse.ubc.ca/2011/docs/chapters/PHC19.pdf.

International Search Report corresponding to international application No. PCT/US2011/040954, date of mailing Oct. 17, 2011, (6 pages).

* cited by examiner

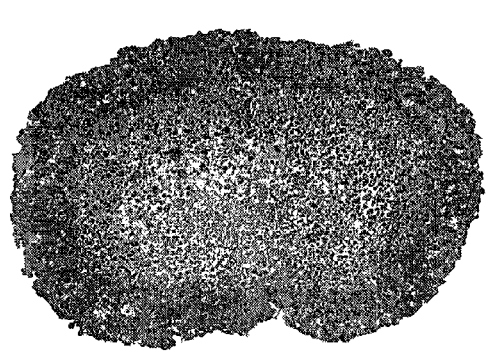
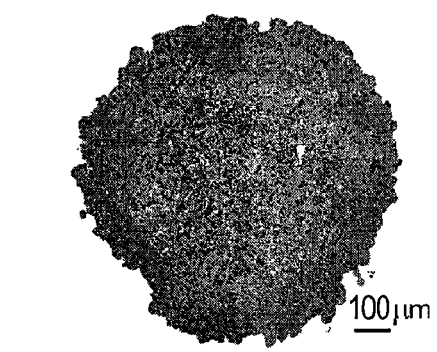
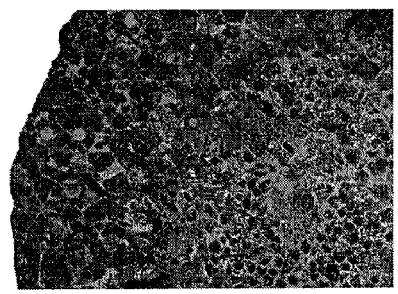
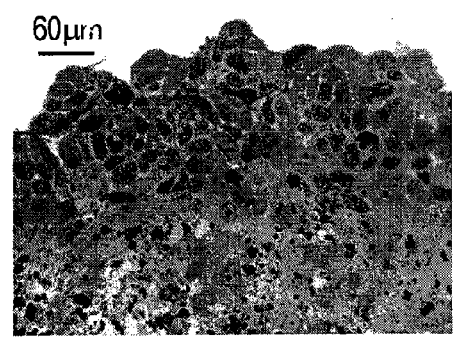
FIG. 5a  FIG. 5b
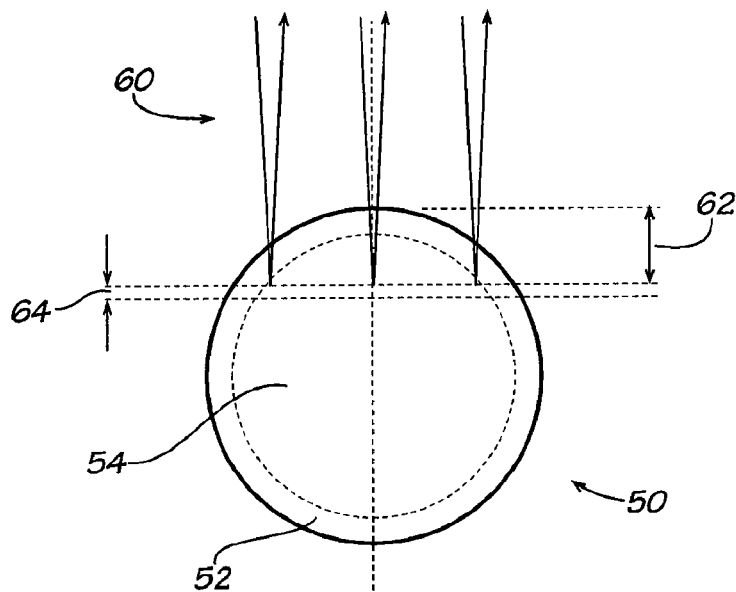
FIG. 6

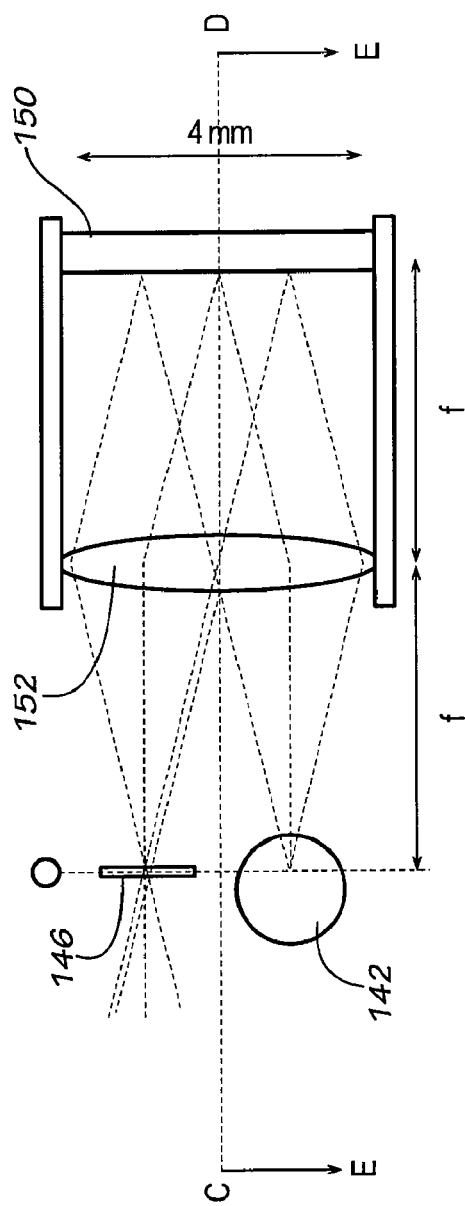
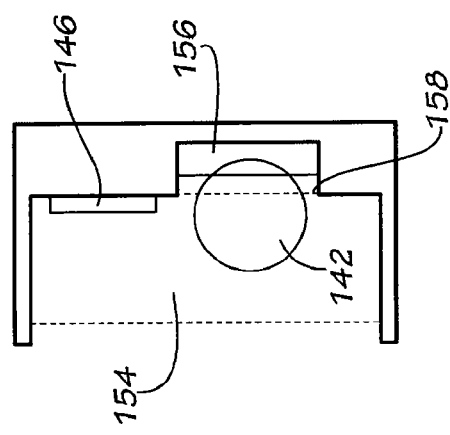
FIG. 15a
FIG. 15b

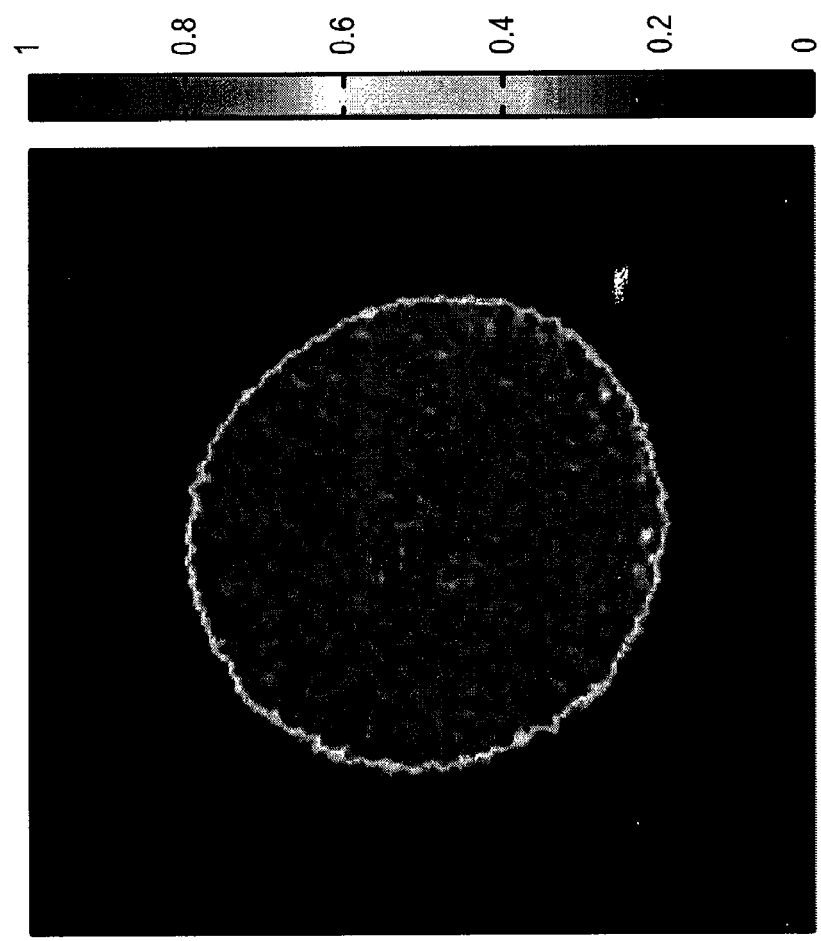
FIG. 26a1

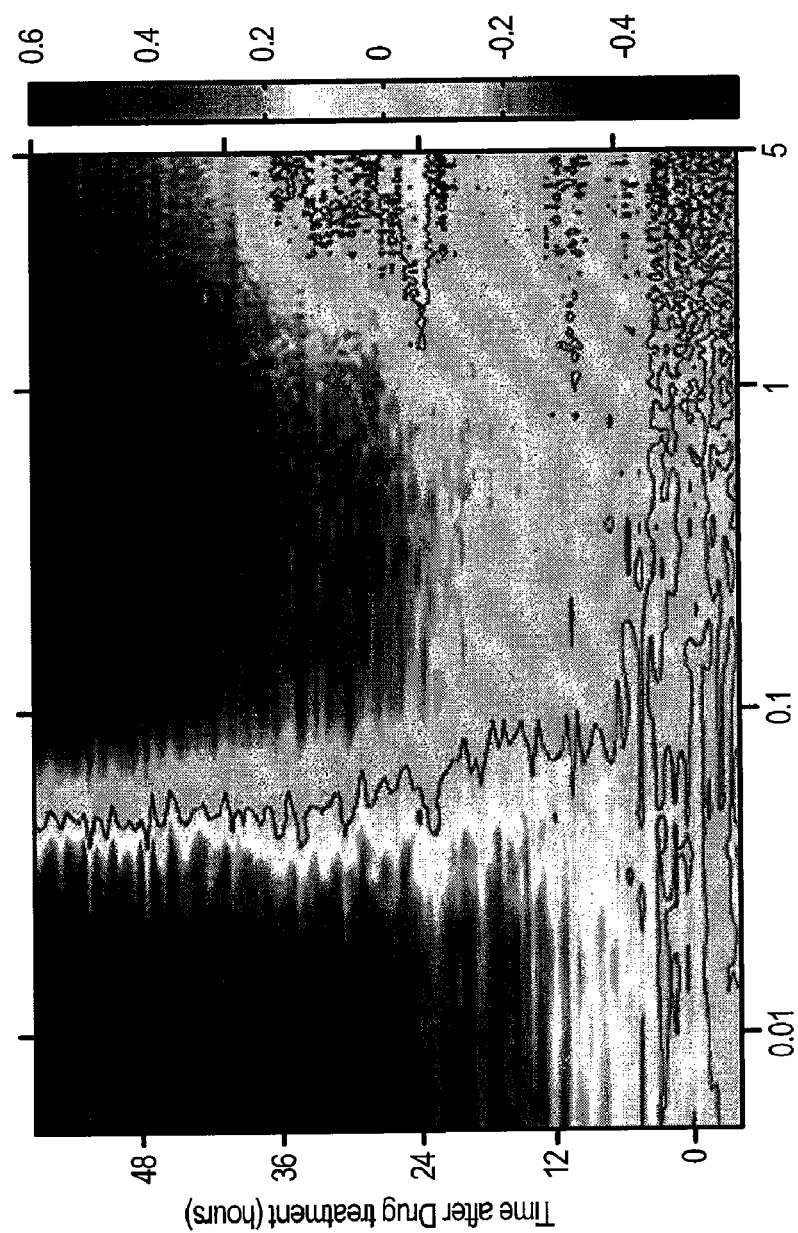
FIG. 26a2

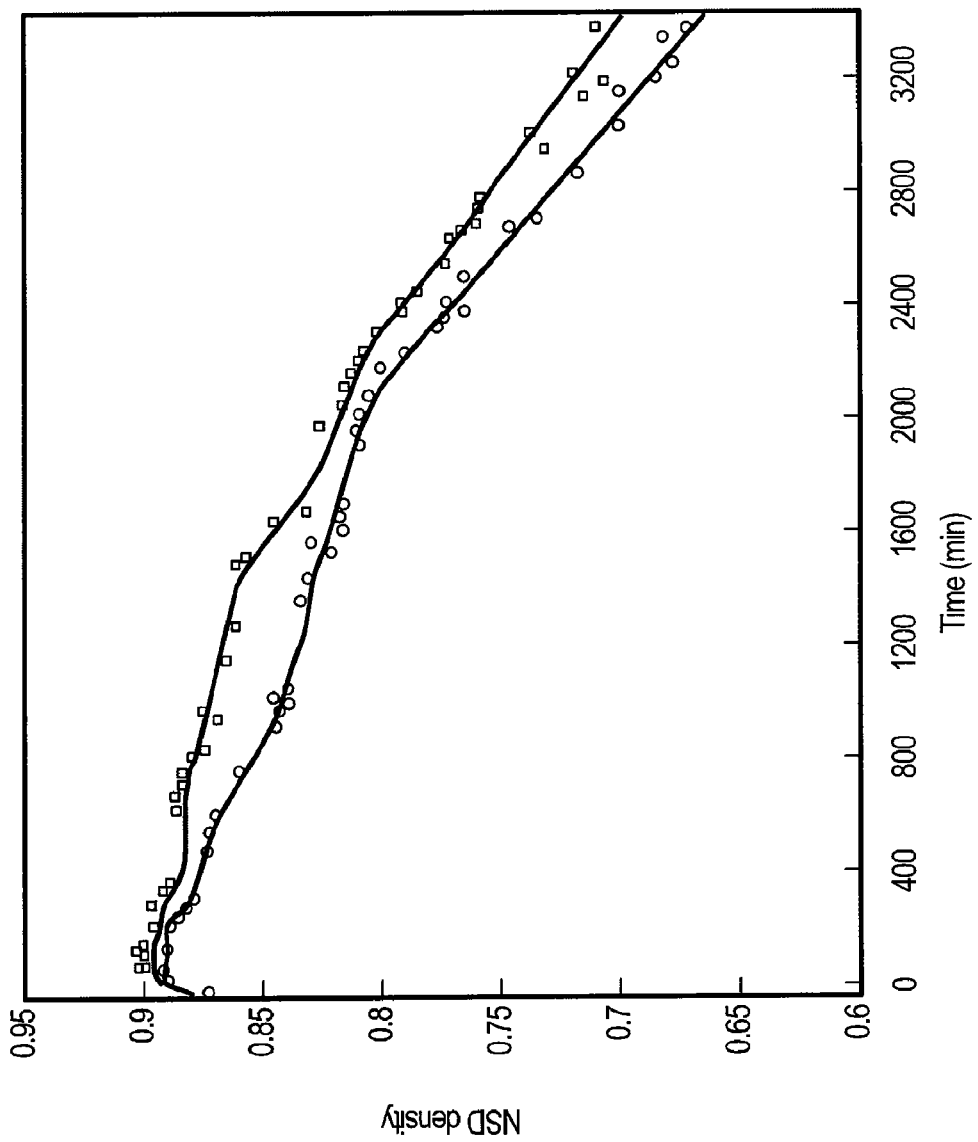
FIG. 26a3

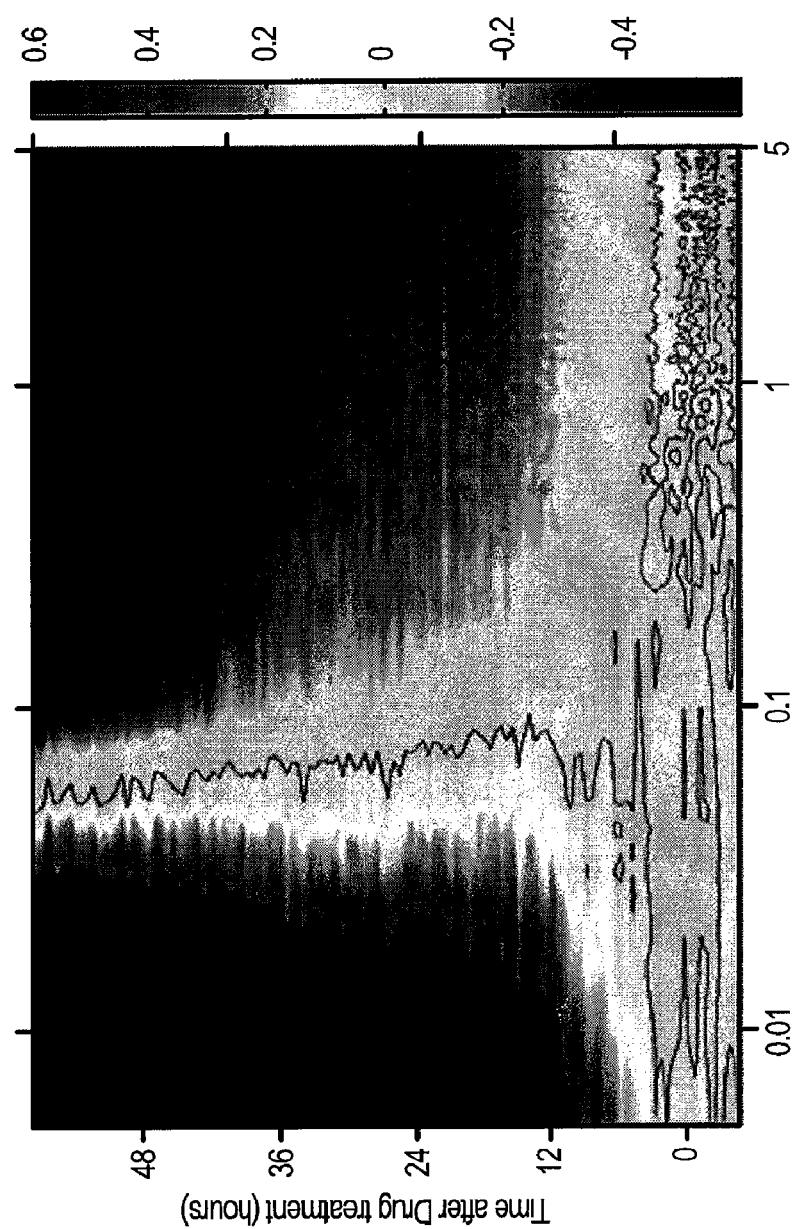
FIG. 26a4

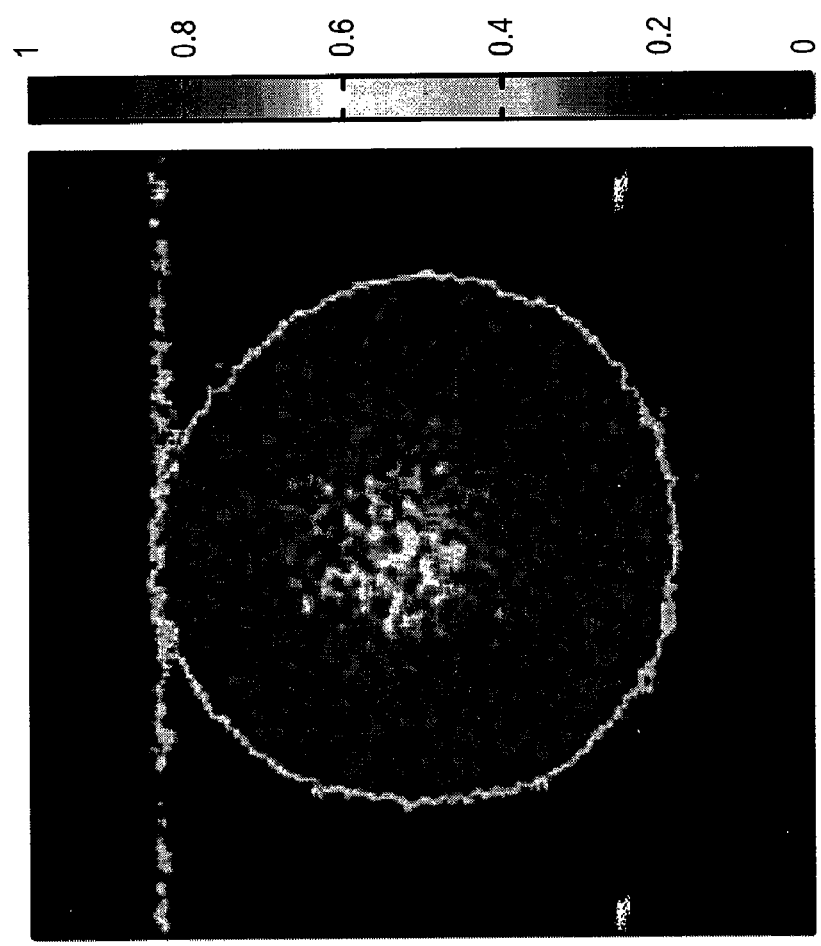
FIG. 26b1

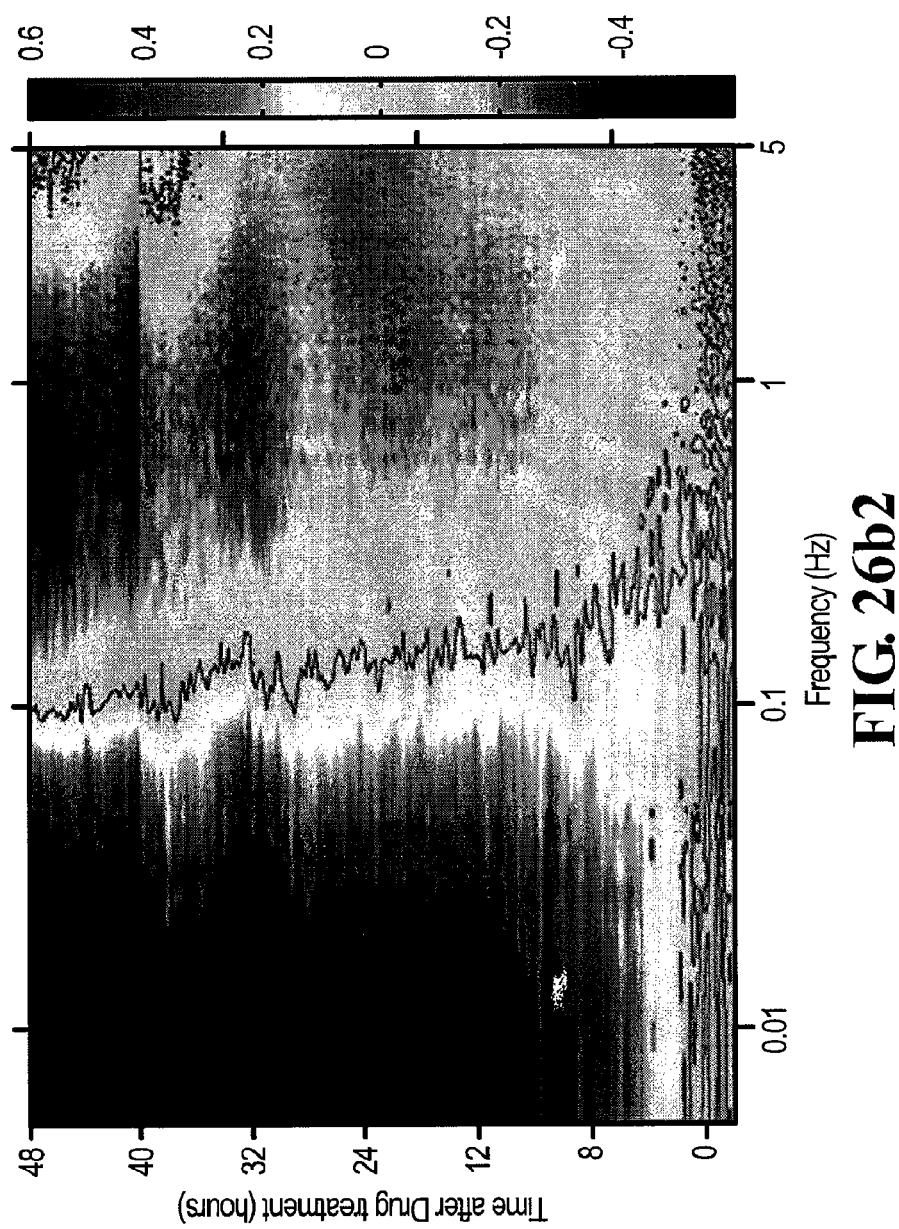
FIG. 26b2

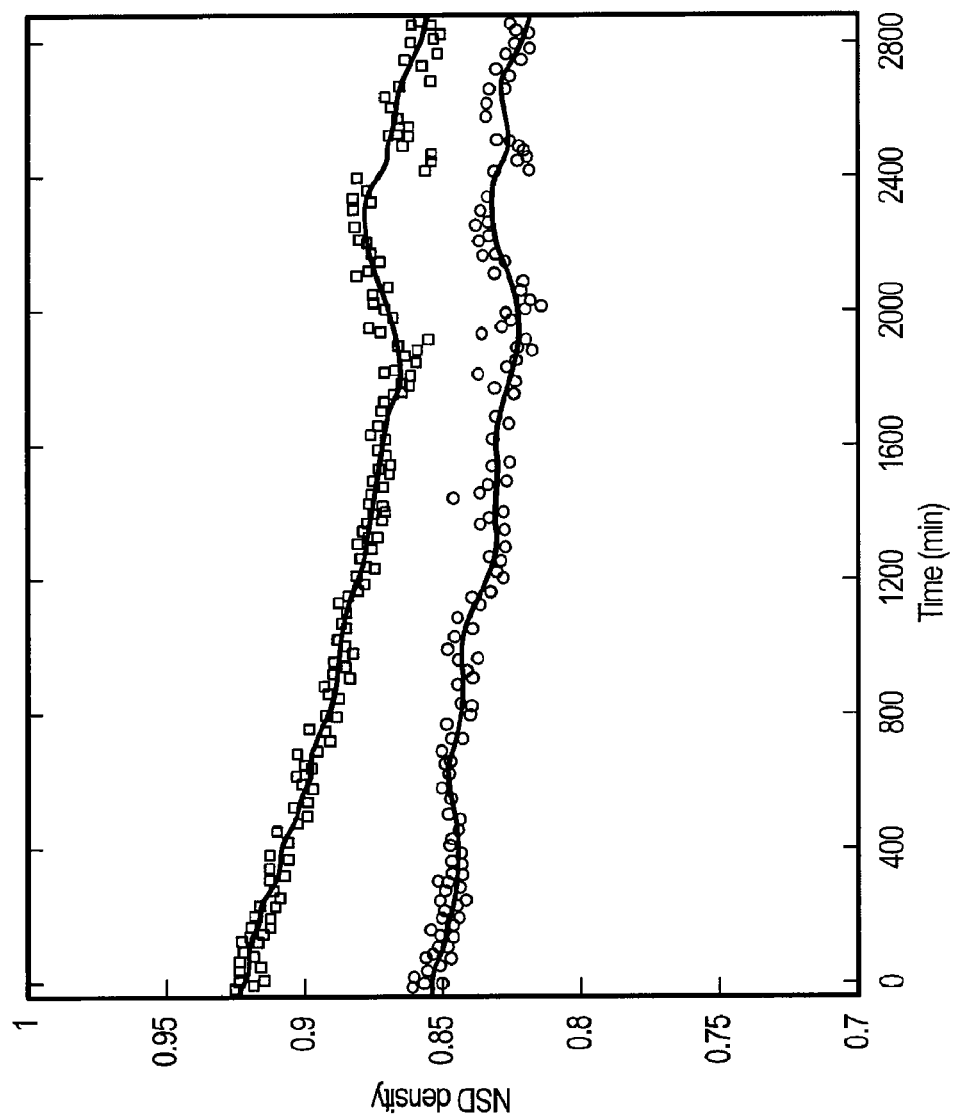
FIG. 26b3

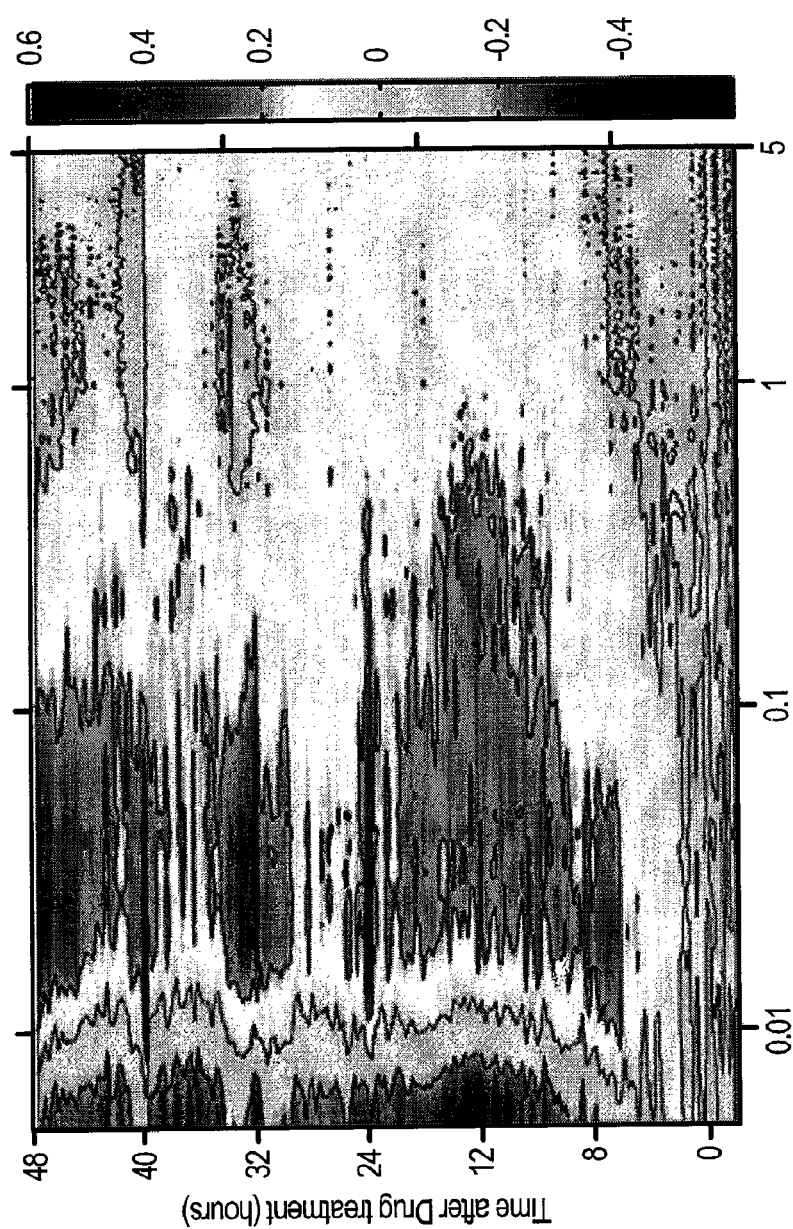
FIG. 26b4

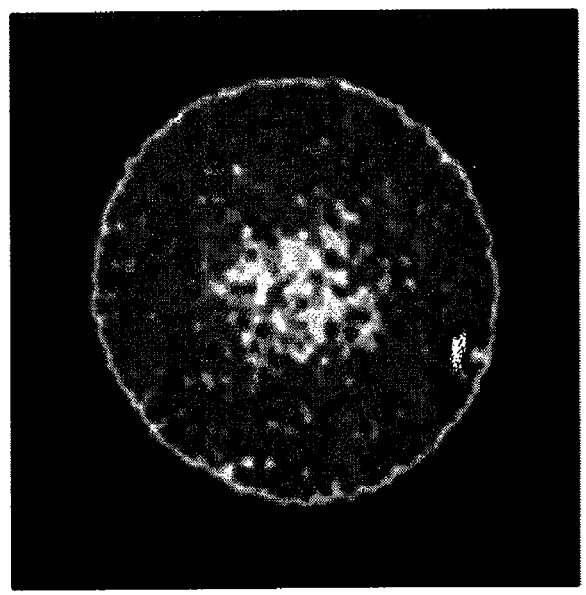
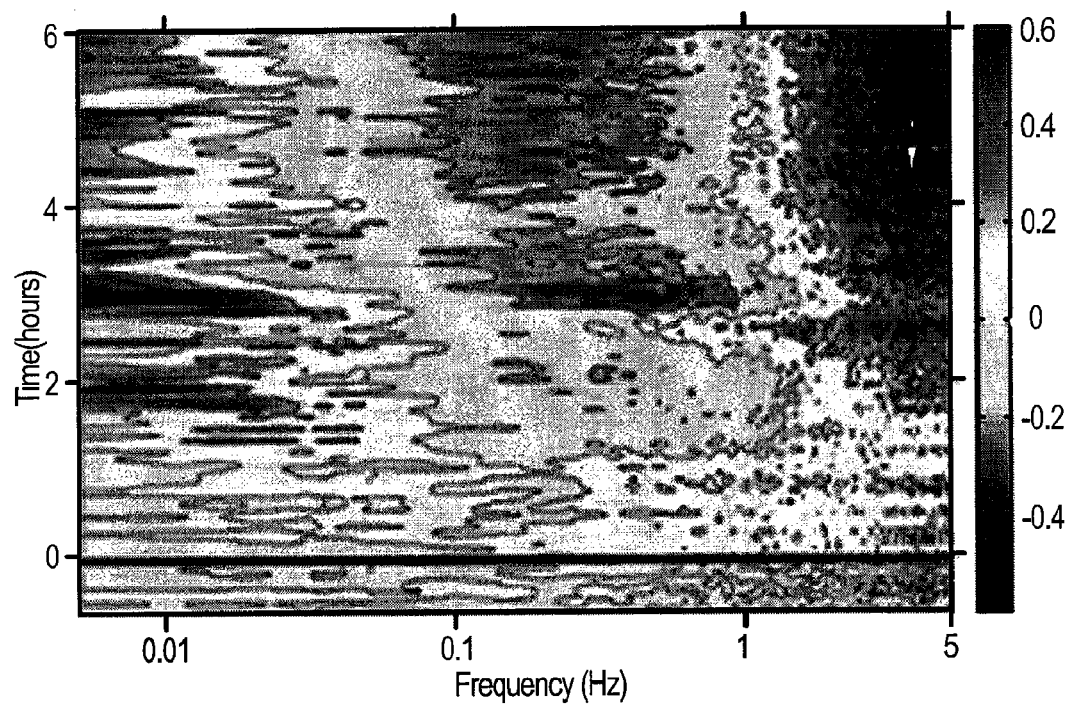
FIG. 36a

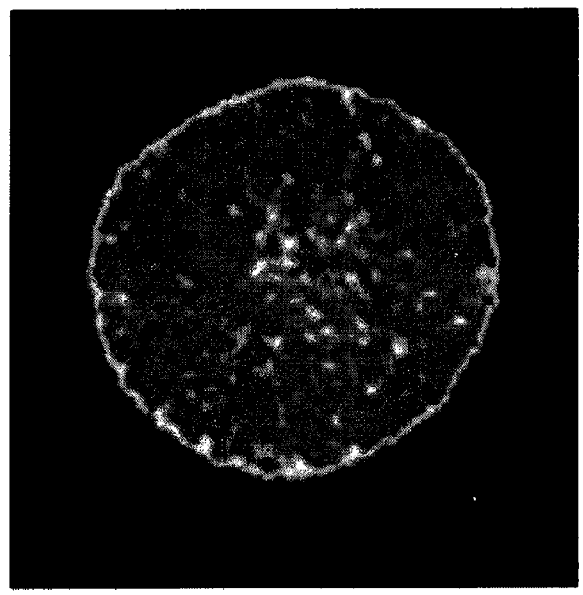
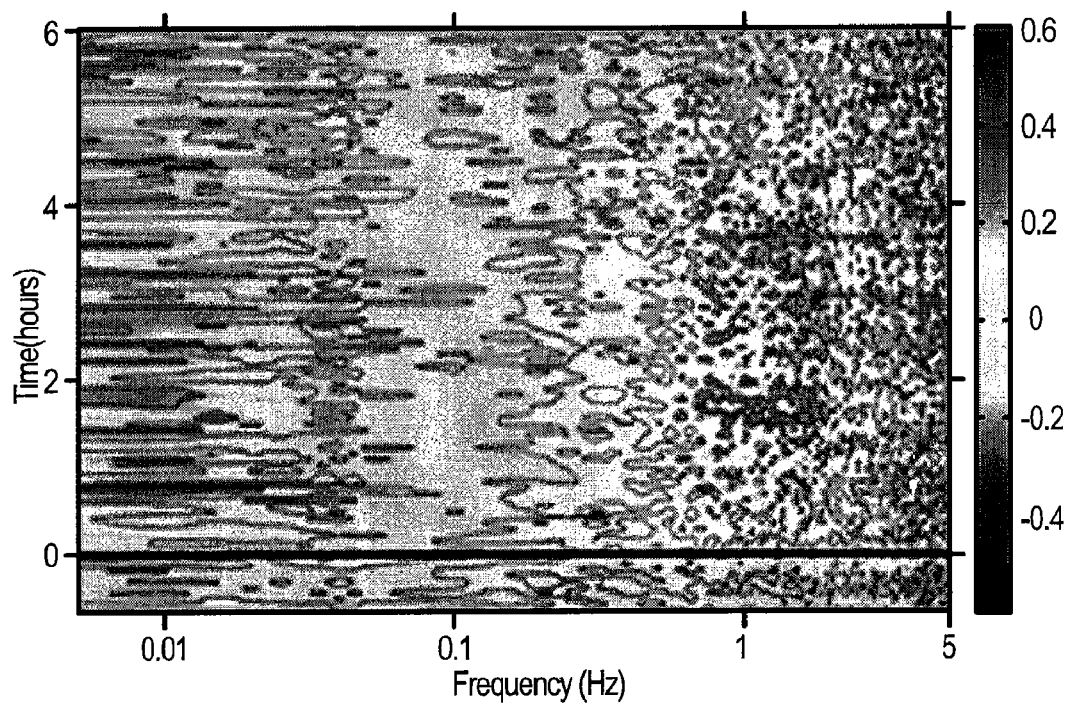
FIG. 36b

DIGITAL HOLOGRAPHIC METHOD OF MEASURING CELLULAR ACTIVITY AND MEASURING APPARATUS WITH IMPROVED STABILITY

CROSS-REFERENCE TO RELATED APPLICATIONS

This application claims the benefit of U.S. Provisional Application Ser. No. 61/397,885, filed on Jun. 17, 2010, entitled "Digital Holographic Method Of Measuring Cellular Activity And Of Using Results To Screen Compounds And Measuring Apparatus With Improved Stability" which is incorporated herein by reference.

GOVERNMENTAL SUPPORT INFORMATION

This invention was made with U.S. Government support from the National Science Foundation grant CBET-0756005. The Government has certain rights in the invention.

BACKGROUND

A discussion of basic principles of Fourier-domain holography is first presented, followed by a discussion of digital holography.

Fourier-Domain Holography

The optical configuration for Fourier-domain digital holographic imaging is shown schematically in FIG. 1, although not to scale. The object plane (x, y) is conjugate to the Fourier plane that is near the output face of the cube beam splitter. The CCD chip is on the Fourier plane. The focal distance between the lens and the Fourier plane is adjusted for the optical path through the glass beamsplitter. The reference plane wave is directed by the beam splitter to intersect with the object wave with a crossing angle θ. The reference wave is incident off-axis, providing a spatial heterodyne signal that modulates the speckle pattern from the object. The interference pattern is recorded on the CCD chip that resides on the Fourier plane (FP). Numerical reconstruction of the image using an FFT is represented as the read-out lens transforming the field back to the space-domain (η, ξ).

An example of a Fourier-domain hologram is shown in FIG. 2(a), with a magnified view of one section shown in FIG. 2(b). This hologram is of lettering on diffusing white paper. The diffuse nature of the target (light scattered into wide angles) ensures that there is a wide recording range on the Fourier plane. The fringe patterns are visible in FIG. 2(b), with a clear periodicity modulated by amplitude and phase across the speckles. The spatial interference fringes modulate the speckle pattern with approximately 2-3 fringes within a speckle coherence length.

The 1-D Fourier transform of the section denoted by the dashed line in FIG. 2(a) is shown in FIG. 3. The zero-order diffraction is the wide base at the center of the graph, including a DC spike at zero spatial frequency. The two broad sidebands at opposite symmetric spatial frequencies are the image information. The spatial frequency width of these first-order peaks is:

$$k_{max} = k \frac{D}{2f} \quad (1)$$

which is determined by the numerical aperture (f/#) of the imaging optics. A 2-D Fourier transform is shown in FIG. 4 using an Air Force test chart as the target. The power spectrum reconstruction produces an image and it's conjugate. The demodulated and transformed images shown in FIG. 4(a) are the direct image and it's conjugate. FIG. 4(b) is a magnified version of the lower-left reconstruction. Phase information can be retrieved by comparing the real and imaginary parts of the image and it's conjugate.

Digital Holography

Digital holograms (containing N×N=800×800 pixels) are encoded on a CCD chip with 4096 gray levels (12 bits). The pixel size is Δx'=Δy'=6.8 μm and the area of the CCD chip is L×L=5.44×5.44 mm². The FFT reconstruction of the digital hologram produces an image with N×N pixels with a pixel size Δξ (Δξ=Δη) given by $$\Delta \xi = \Delta \eta = \lambda f \Delta v_{x'} = \lambda f \Delta v_{y'} = \frac{\lambda f}{L} \quad (2)$$

where $\Delta v_{x'} (\Delta v_{x'} = \Delta v_{y'} = 1/L)$ is the sampling spatial frequency.

To record interference fringes in the digital hologram, the fringe spacing should range from twice the pixel size (minimum) to the CCD chip size (in-line holography). The spatial frequency corresponding to the maximum fringe spacing is $\Delta v_{x'} = 1/L$, and the spatial frequency for the minimum fringe spacing is $1/(2\Delta x') = N\Delta v_{x'}/2$, which is the spatial frequency limit. Four times the pixel size (4Δx') is the best fringe spacing, at which the sideband is located at half of the spatial frequency limit. When the fringe spacing is 4Δx', the maximum field of view for the holographic image is achieved with NΔξ/2=λf/(2Δx'). The fringe spacing for FIG. 2 was 3Δx' with the center of the sideband located at the spatial frequency of 1/(3Δx')=49 mm⁻¹ in FIG. 3.

The transverse resolution in FD-DHOCI (Fourier Domain-Digital Holographic Optical Coherence Imaging) depends on the area of the CCD chip. If the object beam at the Fourier plane covers the full span of the CCD, the transverse resolution at the Rayleigh criterion is $$R_s = 1.22 \lambda f/L = 1.22 \Delta \xi. \quad (3)$$

The longitudinal resolution depends on the coherence length of the short-coherence source and is $$\Delta z = \ln(2) \frac{2}{\pi} \frac{\lambda^2}{\Delta \lambda}. \quad (4)$$

where Δλ is wavelength bandwidth of the source intensity coherence envelope. The 12-bit CCD camera has Δx'=6.8 μm, N=800, λ=840 nm, and f=4.8 cm, and the bandwidth of the source is 17 nm. The transverse and the longitudinal resolution for this system are 9 μm and 18 μm, respectively.

In FD-DHOCI, the CCD camera is placed at the Fourier plane conjugate to the target plane in the object. The depth of focus is $$\Delta z = \frac{\lambda}{2 \cdot NA^2}, \quad (5)$$

where λ is the wavelength and NA is the numerical aperture. The depth of focus for the system with the transverse resolution of 9 μm is 131 μm. The volumetric targets (tumor spheroids) are typically thicker than the depth of focus. The spheroids range in size from 300 μm to 1 mm. To minimize out-of-focus in the numerical reconstruction, the object plane is placed about ⅓ of the way into the tumor from the incident face. In this way, the tumor images remain in focus, except for the back face of the tumor, where multiple scattering and the "showerglass effect" already limit the imaging resolution.

SUMMARY

The acquisition of dynamic speckle is a broad-ranging process shared by many light scattering techniques. In this disclosure we teach how to extract spectrogram fingerprints based on this speckle, with depth-gated selectivity that separates behavior from different parts of the tissue sample. The spectrogram fingerprints capture the different effects that differing drugs and environmental perturbations have on the tissue and the subcellular motion in the cells of the tissue.

By building a spectrogram library of the fingerprints of known drugs with known drug action and cellular toxicity, the library can be used to compare against the spectrogram fingerprints of unknown drug candidates. In this way similar mechanisms of action, and level of toxicity, can be discovered between known and unknown compounds. For classification in mechanism of action, the spectrogram of an unknown compound can be converted to spectrogram features that are compared against features of spectrums of known drugs. The unknown drugs can then be paired up with groups of drugs that share common spectrogram features.

For assessment of drug toxicity, the spectrogram markers for cell health can be established based on response to environmental perturbations. As cell spectrograms deviate from normal response to these stimuli, the degree of cellular health may be measured.

The signature differences between the shell and the core of the tumor spheroids can be measured. The core is either hypoxic, hypoglycemic (starved) or necrotic (or combinations) and hence depleted in ATP, while the shell contains cells in close contact with oxygen and nutrients and enriched in ATP. This tissue precondition affects the spectrogram fingerprints of drugs, and can control whether cells undergo necrosis or apoptosis. This separation of shell and core is unique to optical coherence imaging with its coherence-gated depth selectivity. However, drug toxicity and mechanism of action in healthy tissue can be ascertained without the need for the coherence gate, and can be applied to other imaging approaches that capture speckle from living tissue.

Speckle fluctuation spectroscopy of intra-cellular motion in living tissue using coherence-domain digital holography can be performed. A reference library of "fingerprints" of one or more known compounds can be created, and the "fingerprints" of new compounds can be compared to the reference library. The library might include the "fingerprint" of only one compound, or a plurality of compounds. The reference library may be used to screen compounds for those potentially possessing similar beneficial results. Such beneficial results might include mechanisms of action similar to current anti-mitotic drugs. Additionally, the same or a different reference library might be used to screen for toxicity.

Motility contrast imaging (MCI) is a depth-resolved holographic technique to extract cellular and subcellular motion inside tissue. The holographic basis of the measurement technique makes it highly susceptible to mechanical motion. The motility contrast application, in particular, can include increased mechanical stability because the signal is based on time-varying changes caused by cellular motion, which should not be confused with mechanical motion of the system. Apparatus are disclosed for motility contrast imaging that provide increased mechanical stability. It is based on common-path configurations, in which the signal and reference beams traverse the same optical elements to the detector. The two beams share mechanical motions in common, and hence these motions do not contribute to the signal.

A motility contrast imaging apparatus is disclosed for imaging a tissue sample at a detection plane. The imaging apparatus includes an illumination source, a focusing element, a mirror, a collecting element and a detector. The illumination source provides an illumination beam that is split into a collimated reference beam and a collimated signal beam, the collimated signal beam being scattered by the tissue sample at the detection plane. The focusing element focuses the reference beam onto the detection plane, and the mirror reflects the focused reference beam from the detection plane. The collecting element collects the reflected reference beam and the scattered signal beam, and the detector detects the collected reflected reference beam and the collected scattered signal beam. The apparatus can also include a beam expander for expanding the illumination beam before the illumination beam is split into the collimated reference and signal beams. The beam expander can be a cylindrical leans beam expander. The focusing element can be a cylindrical leans. The mirror can be located in a well containing the tissue sample. The collecting element can be a Fourier-transform lens where the detector is located at the Fourier plane; the crossing angle between the reference beam and the signal beam at the detector providing a carrier frequency for digital holography. The detector can be a CCD chip.

A motility contrast imaging apparatus for imaging a tissue sample is disclosed that includes an illumination source, an opaque aperture mask, a mirror, a Fourier transform lens, a prism, a variable compensator and a detector. The illumination source provides a signal beam and a reference beam. The opaque aperture mask has a signal opening where the signal beam is scattered by the tissue sample and passes through the signal opening. The mirror is located substantially adjacent laterally to the tissue sample and the reference beam is reflected by the mirror. The scattered signal beam passes through the Fourier transform lens. The prism is adjacent laterally to the Fourier transform lens, and the reflected reference beam is deflected by the prism to intersect an optical axis of the signal beam at the Fourier plane of the Fourier transform lens. The variable compensator is tuned to compensate for path length differences between the signal beam and the reference beam paths, the signal beam passing through the variable compensator. The detector is located at the Fourier plane, and detects the path-compensated scattered signal beam passing through the Fourier transform lens and the intersecting reference beam deflected by the prism. The apparatus can also include a polarizing beam splitter, the signal beam being deflected by the polarizing beam splitter and then backscattered by the tissue sample and passed through the polarizing beam splitter; the reference beam being deflected by the polarizing beam splitter and then reflected by the mirror and passed through the polarizing beam splitter. The mirror can be attached to the opaque aperture mask advance of the tissue sample to help compensate for the distance traveled by the reference beam relative to the signal beam. The tissue sample can be on a plate tilted relative to the optical axis of the signal beam to prevent specular reflection. The illumination source can generates a Gaussian beam, the signal beam being on the optical axis of the Gaussian beam and the reference beam being a side-lobe of the Gaussian beam. The mirror can be laterally adjacent to the tissue sample and the opaque optical mask can have a reference opening; the mirror and tissue sample being on one side of the opaque optical mask and the detector being on the opposite side of the opaque optical mask; the signal beam being side-scattered by the tissue sample and passing through the signal opening of the opaque optical mask towards the detector, and the mirror being positioned to reflect the reference beam through the reference opening of the opaque optical mask parallel to the signal beam towards the detector. The apparatus can also include a quarter wave plate located next to the opaque optical mask, the tissue sample and mirror being on one side of the quarter wave plate and the detector being on the opposite side of the quarter wave plate. The variable compensator can include a first dielectric plate placed in the signal path and a second dielectric plate placed in the reference path. The variable compensator can be tuned to define a depth gate within the tissue sample.

A motility contrast imaging apparatus for writing Fourier-domain holograms with speckle modulation from a tissue sample is disclosed that includes an illumination source, a focusing lens, a transparent coverslip, a beam splitter, a Fourier transform lens and a detector. The illumination source provides illumination pulses including a leading pulse and a trailing pulse. The focusing lens focuses the illumination pulses in front of the tissue sample. The transparent coverslip covers the tissue sample, the coverslip and tissue sample comprising a target. The beam splitter reflects the illumination pulses, after the illumination pulses pass through the focusing lens, onto the target and passes through the return pulses. The Fourier transform lens processes the return pulses, and the detector is located at the Fourier plane of the Fourier transform lens to receive the processed pulses. The leading pulse is scattered by the tissue sample and the trailing pulse is reflected by the coverslip. The leading pulse is time-coincident with the trailing pulse to define a coherence-gated depth of the target showing interference at the detector. The illumination source can be a fiber-optic interferometer configuration with a variable delay. The speckle on the detector can be modulated by moving the focusing lens. The detector can be a CCD array.

Multiple embodiments are disclosed and claimed herein. There are numerous refinements that are generally applicable to most, if not all, of these embodiments.

BRIEF DESCRIPTION OF THE FIGURES

FIG. 5(a) shows images of a human liver tumor spheroid and FIG. 5(b) shows images of a rat osteogenic tumor spheroid which have different shapes and texture, but both have outer proliferating shells 100-200 microns thick encapsulating a necrotic core; and the lower images are magnified portions of the full spheroid images;

FIG. 6 is a schematic of the tumor spheroid morphology and the coherence slab defined by the reference wave;

FIG. 15(a) shows a detection system for stable holography where the reference arm expands off the mirror of the sample well and is collimated by the Fourier-transform (FT) lens, the light scattered from the tumor is collected and transformed to the Fourier plane at the CCD chip, and a crossing angle between the reference arm and the signal arm, provides the carrier frequency for the digital holography;

FIG. 15(b) shows an exemplary well holding a tissue sample and mirror;

FIG. 26 shows the long-term effects of changing growth medium, where the data in FIG. 26(a) are for 2 days without changing the growth medium and the data in FIG. 26(b) are for 2 days while changing the growth medium every 8 hours showing that the tissue degrades significantly after 12 hours without new growth medium, and even with replenished growth medium, the healthy shell shows a strong shift to lower frequencies after about 8 hours but the core is significantly stabilized by the replenishment of the growth medium;

FIG. 36 shows a comparison of iodoacetate (FIG. 36(a)) and KCN (FIG. 36(b)) spectrograms at 37° C.;

DESCRIPTION OF EXEMPLARY EMBODIMENTS

Figure 1:
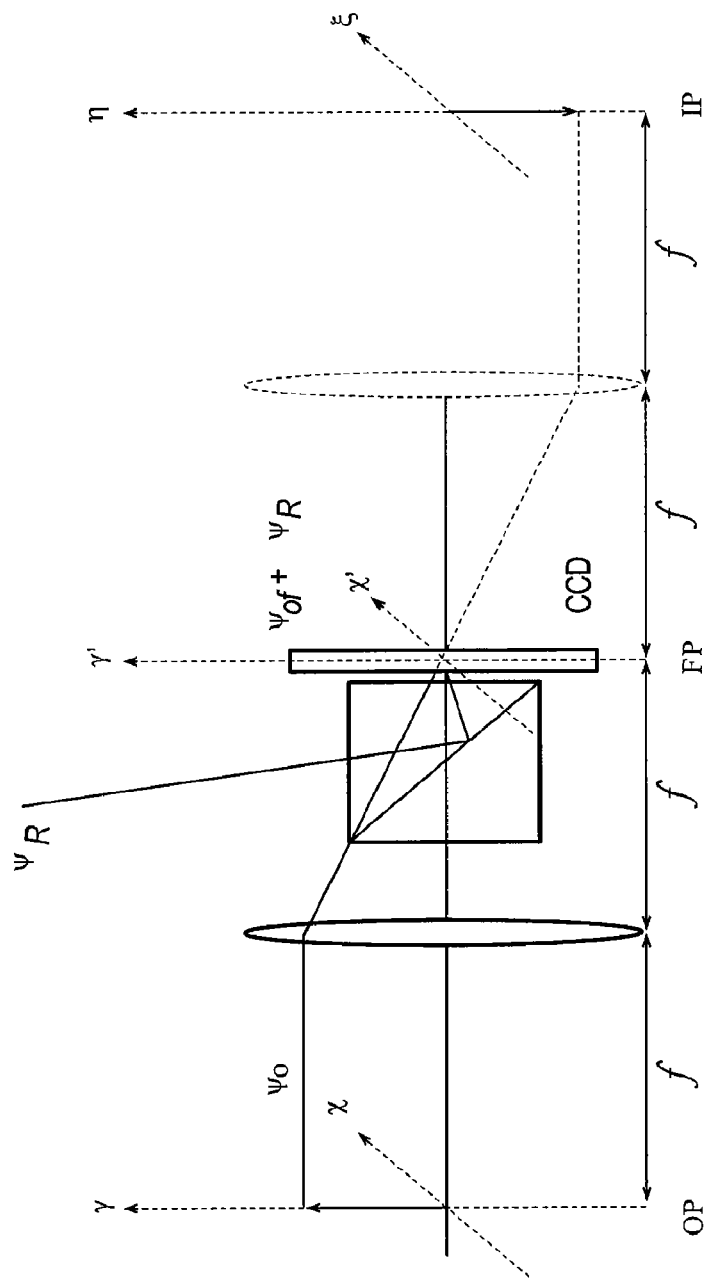
FIG. 1 illustrates a schematic of an optical configuration for digital holographic imaging where the CCD is on the Fourier plane that is conjugate to the object plane, and the reference wave is incident off-axis providing a spatial heterodyne signal that modulates the speckle pattern from the object.

For purposes of promoting an understanding of the principles of the inventions, reference will now be made to the embodiments illustrated in the drawings and specific language will be used to describe the same. It will nevertheless be understood that no limitation of the scope of the inventions is thereby intended, such alterations and further modifications in the illustrated devices, and such further applications of the principles of the inventions as illustrated therein being contemplated as would normally occur to one skilled in the art to which the inventions relate.

Multicellular Tumor Spheroids

Multicellular spheroids of normal cells or neoplastic cells (tumor spheroids) are balls of cells that may be easily cultured up to 1 mm in size in vitro. The spheroids can be used to simulate the optical properties of a variety of tissues such as the epidermis and various epithelial tissues and may be used to simulate the histological and metabolic features of small nodular tumors in the early avascular stages of growth. The multicellular tumor spheroids are a model of 3-D aggregates of permanent cell lines for the systematic study of tumor response to therapy.

Beyond a critical size (about 100 microns) most spheroids develop a necrotic core surrounded by a shell of viable, proliferating cells, with a thickness varying from 100 to 300 µm. The development of necrosis has been linked to deficiencies in the metabolites related to energy generation and transfer. The limiting factor for necrosis development is oxygen—the oxygen consumption and oxygen transport reflecting the status of the spheroid. Early work studied therapeutic strategies for cancer, and especially the spheroid response to different drugs. The response to drug therapy was quantified by spheroid volume growth delay, increase in the necrotic area, and change in survival capacity. This work focused on hypoxia and its induction by chemical agents To create tumor spheroids for our studies, two different cell lines were used: rat osteogenic sarcoma UMR-106 cells, and human liver carcinoma Hep G2 cells. These were cultured in a rotating bioreactor (Synthecon, Houston, Tex.) where they were maintained in suspension. The spheroids may be grown up to a mm in diameter. An advantage to using this continuous culture model is that fresh spheroids of varying size are easily prepared on a daily basis. Overall, the tumor spheroids provide a reasonable tissue model that does not require special handling of animal subjects.

Electron microscopy sections of the two types of tumor embedded in Toluidine-blue-stained epoxy resin and sectioned at 1 µm thickness are shown in FIG. 5. The tumors are nearly a millimeter in diameter and share common morphology. FIG. 5(a) shows a human liver tumor and FIG. 5(b) shows a rat osteogenic tumor. They each have different shapes and texture, but both have outer proliferating shells encapsulating a necrotic core. The upper images show the full spheroid and the lower images are magnified portions of the full spheroid images. The outermost layers of the tumors have healthy proliferating cells that form a shell from 100 microns to 200 microns thick. These cells are in close proximity to the nutrients and oxygen of the growth medium. This layer is structurally homogeneous and may be expected to be optically homogeneous as well. Deeper inside the tumors, the cells become apoptotic because of nutrient deprivation and oxidative stress caused by reduced nutrient and oxygen diffusion into these avascular spheroids. The apoptotic cells give way, deeper in the tumor spheroids, to necrotic regions characterized by voids of extracellular debris or by microcalcifications, which are especially pronounced in the osteogenic spheroids. The core is structurally heterogeneous, and may be expected to be optically heterogeneous as well. Therefore the tumor spheroids have the general morphology of a healthy outer shell that tends to be homogeneous, surrounding a necrotic core that is spatially heterogeneous. Optical studies of the spheroids would be expected to correspond with this overall structure.

The experimentally measured reduced scattering coefficient $\mu'$ of rat osteogenic tumor spheroids is on the order of 8 $mm^{-1}$ to 15 $mm^{-1}$ with decreasing extinction with increasing tumor size. A tumor with a diameter of 416 microns was fit best with an anisotropy factor of g=0.9, while a slightly larger tumor with a diameter of 484 microns was fit with a smaller factor of g=0.85. Overall, the rat osteogenic tumor spheroids are relatively translucent tumors with strong forward scattering.

Holographic Optical Coherence Imaging of Tumor Spheroids

The scattering geometry of a tumor spheroid 50 is shown in FIG. 6. The tumor spheroid 50 has a healthy shell 52 surrounding a necrotic core 54. Light 60 is incident from the top, uniformly illuminating the full tumor, and reflected back. The coherence gate set by the reference pulse defines the section depth 62, and the coherence length of the laser sets the section thickness 64. Because of the off-axis holography configuration in the recording, the actual section is tilted by half the crossing angle at the CCD between the signal arm and the reference arm. Data are acquired in a mode called a "fly through" in which the section depth is swept through the full volume of the tumor spheroid from top to bottom. (In inverted configurations, the light is incident from the bottom of the tumor and the section sweeps from bottom to top.) The step size between sections is 10 microns (approximately half of the coherence length) and the exposure time per section is approximately 1 second.

Figure 7A:
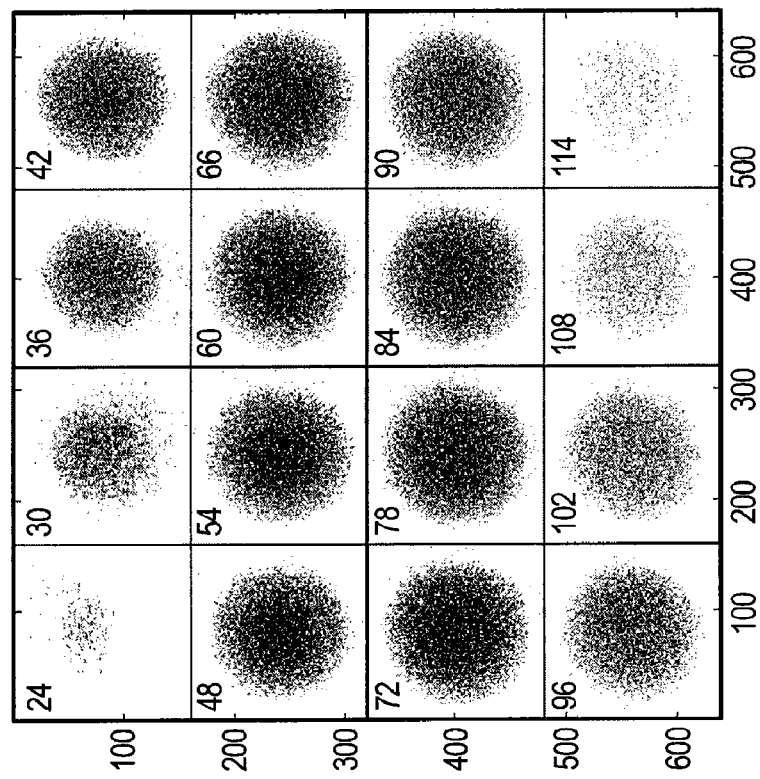
FIG. 7(a) shows selected en-face sections of an 800 micron-diameter tumor spheroid.
Figure 7B:
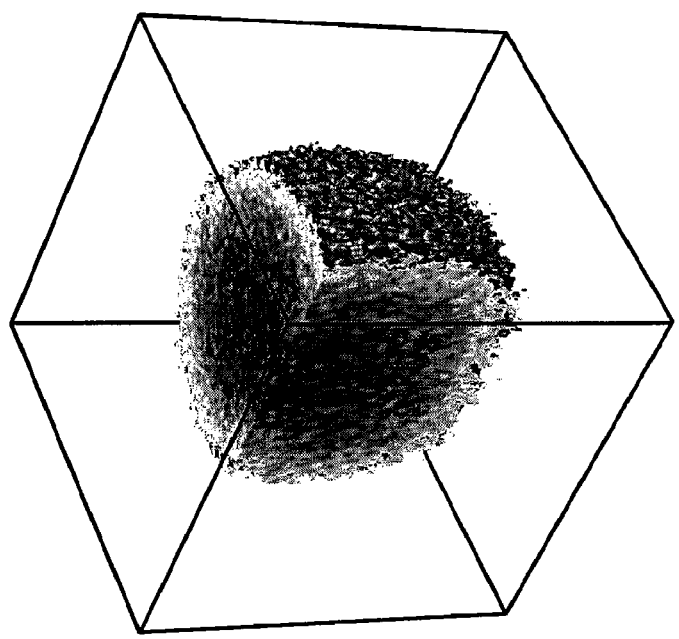
FIG. 7(b) shows a reconstructed volume showing reflectance (darker stands for more intense reflections) where the shades are on a logarithmic scale that span approximately 40 dB within the tissue.

FIG. 7(a) shows a stack of selected sections of an 800 micron diameter tumor spheroid. In this case the light was incident from the bottom (frame 24). The midsection is approximately at frame 60, and the top of the tumor is at frame 114. These stacks are combined into a reconstructed data volume representing the tumor in FIG. 7(b) showing reflectance. The grayscale is on a logarithmic scale spanning about 40 dB from brightest to darkest. The brightest reflections (darkest pixels) are near the center, corresponding to the necrotic core. The outer healthy shell has noticeably weaker reflections.

Figure 8:
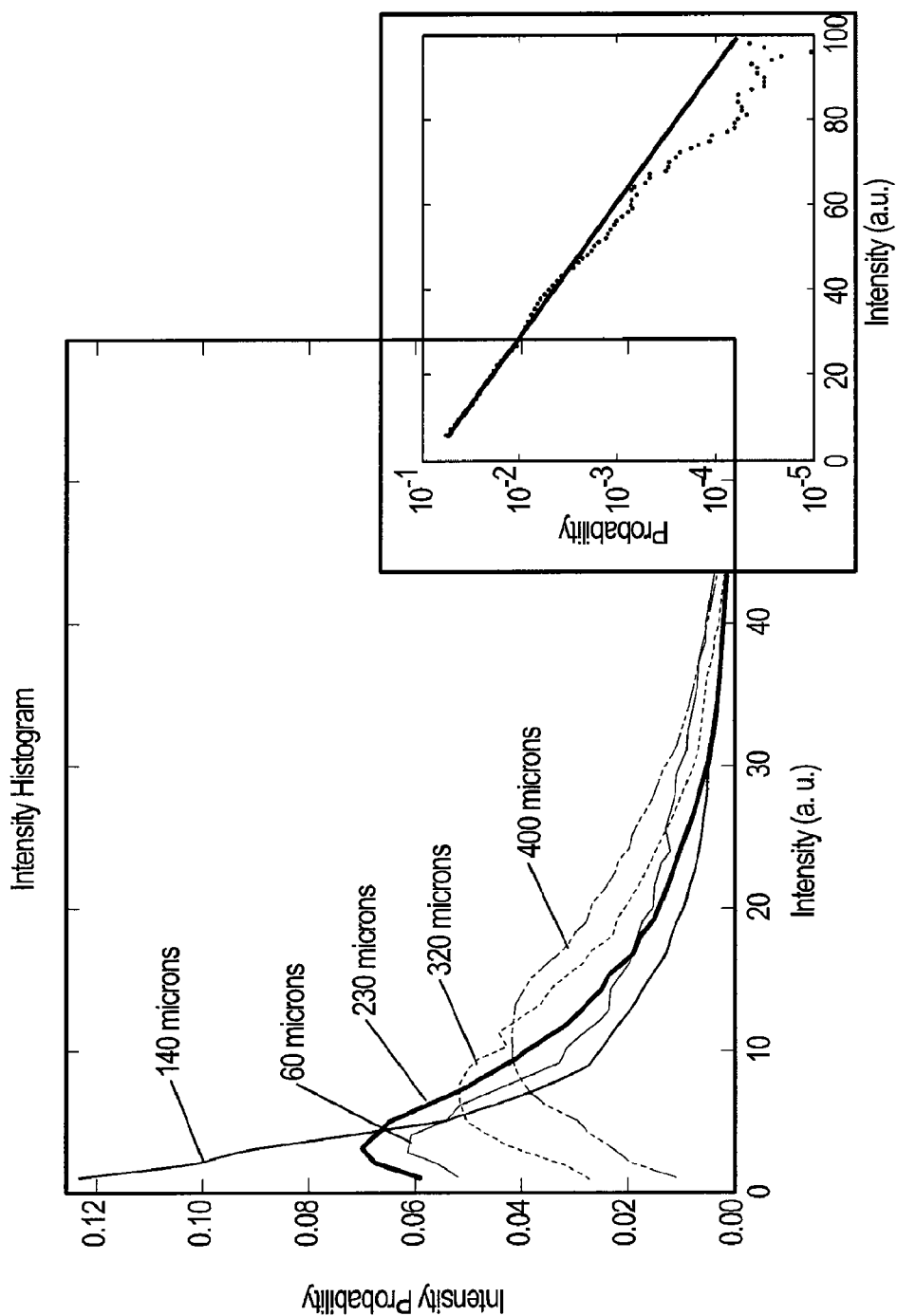
FIG. 8 shows histograms of speckle intensities from a 560 micron diameter tumor spheroid at several depths where the speckle data from a depth of 140 microns (near the transition from the healthy shell to the necrotic core) shows nearly perfect Poisson statistics.

The section images and the volume representation in FIG. 7 show strong speckle character. Histograms of the reconstructed intensities are shown in FIG. 8 at different depths through the tumor. The histogram at a depth of 140 microns (near the transition from the healthy shell to the necrotic core) shows a nearly perfect exponential decay (inset) typical of fully-developed speckle. Deeper in the core, there is a distinct peak to the intensity histograms, likely caused by the presence of strongly localized scattering regions. Therefore, the global structure of the tumor spheroid, delineating the healthy outer shell and the necrotic core, is captured by the statistical properties of the speckle. However, specific structures inside the tumor spheroids are difficult to identify. This is mainly because the tumor spheroids are highly homogeneous, consisting of undifferentiated cellular tissue. But this is also because of the strongly speckled character of the holographic reconstructions. This strong speckle becomes an important feature of dynamic imaging.

Subcellular Motility in Tissues

Motion is the over-arching characteristic that distinguishes living from inanimate matter. The cellular machinery that drives motion consists of molecular motors and their molecular tracks known as the cytoskeleton. The cytoskeleton is composed of three types of filaments: microtubules, actin and intermediate filaments. Of these, the best studied and understood are the microtubules and actin. Microtubules form interconnected pathways that span the cytosol that provide molecular highways for organelles carried by molecular motors like kinesin and dynein. The smaller actin filaments form a tight mesh called the cell cortex concentrated mostly near the cell membrane, but with lower densities throughout the cytosol. The actin skeleton lends mechanical stability to the cell membrane and allows its motion, including the crawling of metastatic cancer cells through tissue.

The most active use of the cytoskeletal machinery occurs during mitosis in which the entire cellular structure is reorganized prior to and during division. During mitosis, the microtubules form the mitotic spindle, which is an organized mechanical structure that helps divide the intracellular contents for cell division. Actin plays an important role in cytokinesis at the end of mitosis when the cell membrane pinches off, and the cell physically divides. For these reasons, drugs that inhibit the motors and their tracks are common anti-cancer agents, arresting the cell cycle by arresting motion.

The largest class of anti-cancer therapeutic agents are known as anti-mitotic drugs (AMD), also called cytoskeletal drugs. These drugs affect the cellular cytoskeleton and prevent cells from entering the mitosis phase of the cell cycle. Some of the best known anti-cancer drugs fall in this class, such as Taxol and Colchicine. Although efficacious, these drugs have serious toxic side effects because their action is non-specific as they affect the cytoskeleton of healthy and cancer cell alike. Morbidity and death from the side effects of chemotherapy rival the death rate from the disease itself. Therefore, a modern generation of anti-mitotic agents are being investigated that specifically target actively dividing cells, while leaving interphase cells alone. Some of these drugs act on certain myosin molecular motors that only function during mitosis and are quiescent otherwise. Others act on proteins of the signaling pathways that constitute the mitotic checkpoints of the cell cycle. By turning off selected molecular signals with these drugs, the cell cycle is arrested, and cancer cells do not proliferate.

Motility Contrast Imaging

Figures 9A, 9B:
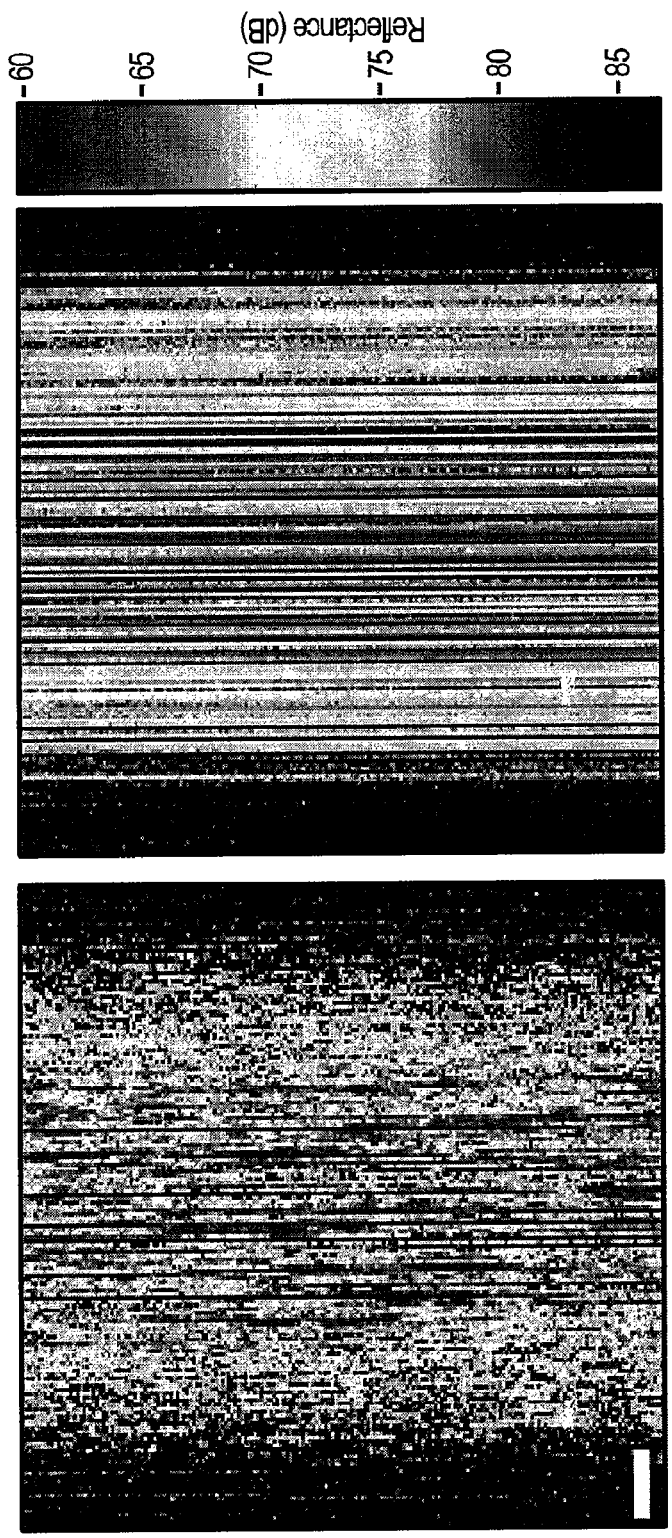
FIG. 9 shows constant-depth one-dimensional sections of a healthy tumor in FIG. 9(a) and of a tumor crosslinked with glutaraldehyde in FIG. 9(b) where the vertical axis is frame number at a rate of one frame per second.

Motility contrast imaging relies on dynamic light scattering combined with coherence gating. Digital holography fulfills the function of the coherence detection and hence the depth discrimination when using a short-coherence source, while consecutive images acquired at successive times fulfill the function of dynamic speckle recording. The data acquisition process includes setting the optical path of the reference arm (and hence the depth inside the tissue), and recording consecutive holograms on the CCD chip, followed by numerical reconstruction. Data from a fixed depth of about 300 microns inside two tumors are shown in FIG. 9. The data are the reconstructed pixel intensities plotted on a dB reflectance scale. The tumor in FIG. 9(a) was "healthy" while the tumor in FIG. 9(b) had been crosslinked with glutaraldehyde. The reconstructed data are displayed as a one-dimensional cut in space with distance along the horizontal axis and time along the vertical axis. The vertical axis is frame number at a rate of one frame per second. The healthy tumor displays strongly dynamic speckle fluctuations, with individual speckles blinking on and off, indicative of living tissue. The cross-linked tumor, on the other hand, displays static speckle.

Figures 10A, 10B:
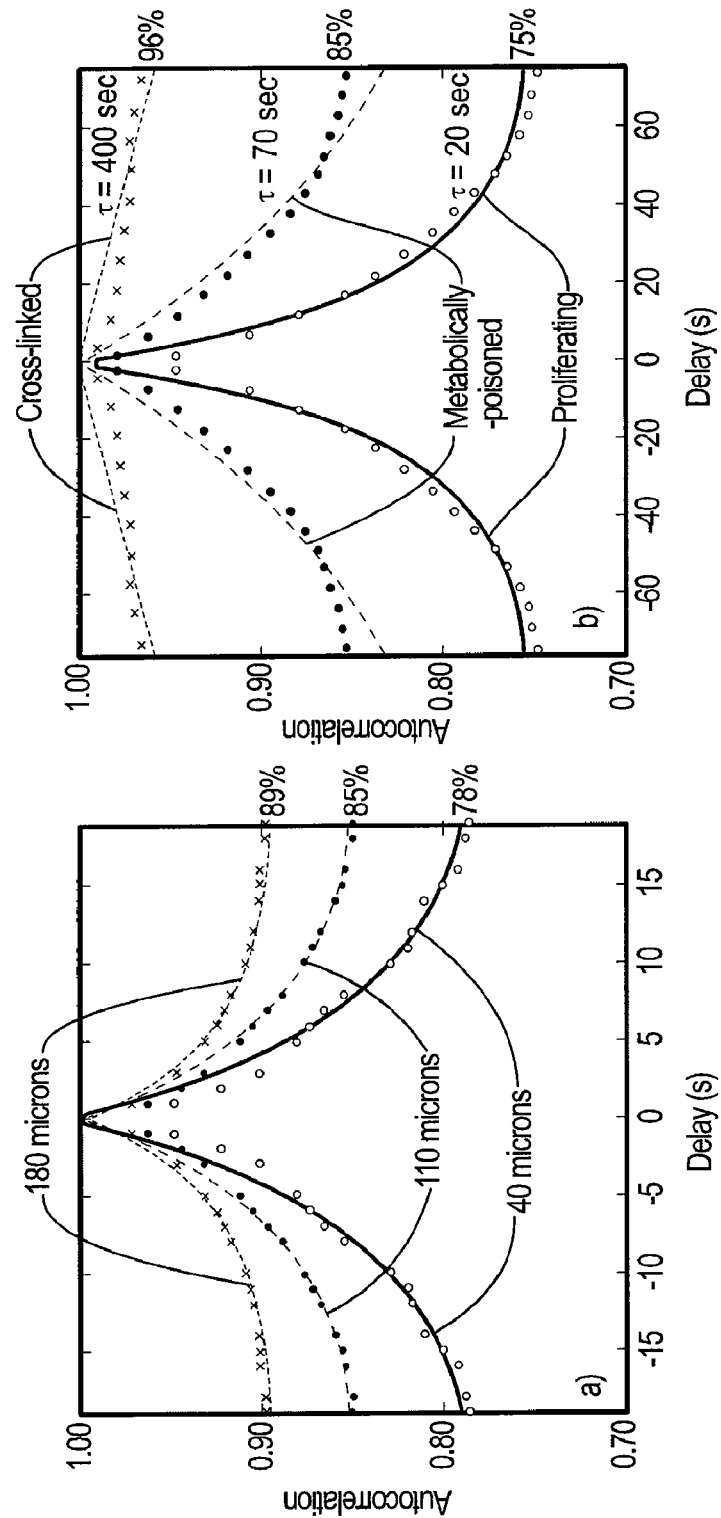
FIG. 10 shows autocorrelation graphs of fixed-depth time sequence data for a healthy tumor at selected depths in FIG. 10(a) and for tumors at a fixed depth but different metabolic conditions in FIG. 10(b)

One goal of the data analysis is to extract the statistical properties of the speckle and to relate them to structure and function. The average autocorrelation graph of a proliferating healthy tumor at depths of 40, 110 and 180 microns is shown in FIG. 10(a). The most dynamic tissue (shortest correlation time and lowest long-time correlation value) is near the surface of the tumor within the healthy shell of proliferating cells. The least dynamic tissue, by contrast, was the deepest section (in this figure at 180 microns). This depth is near the transition from the proliferating cells to the necrotic core. These correlation data show the clear difference between the highly motile outer shell and the quiescent necrotic layers deeper inside.

Tumors under different physiological conditions also show clear differences in the dynamic speckle. Autocorrelation graphs for the three physiological states of healthy/proliferating, metabolically poisoned and cross-linked are shown in FIG. 10(b). The cross-linked tumor shows nearly constant correlation as a function of delay. The healthy tumor shows the most dramatic decrease, while the metabolically poisoned tumor falls in between these two extremes. These autocorrelation data can be used to estimate the speed distribution in the tissue for motile scatterers dominated by drift. The speeds for the three tissue conditions are 3 nm/sec, 1 nm/sec and 0.1 nm/sec for healthy, poisoned and cross-linked tumors, respectively. These speeds are consistent with the fairly broad range of velocities for movements of the cell membrane. However, selecting autocorrelation times to differentiate healthy from necrotic tissue is not robust. There are other choices for a motility metric that can reliably differentiate between healthy and necrotic tissue, and these become the basis of motility contrast imaging.

Figure 11:
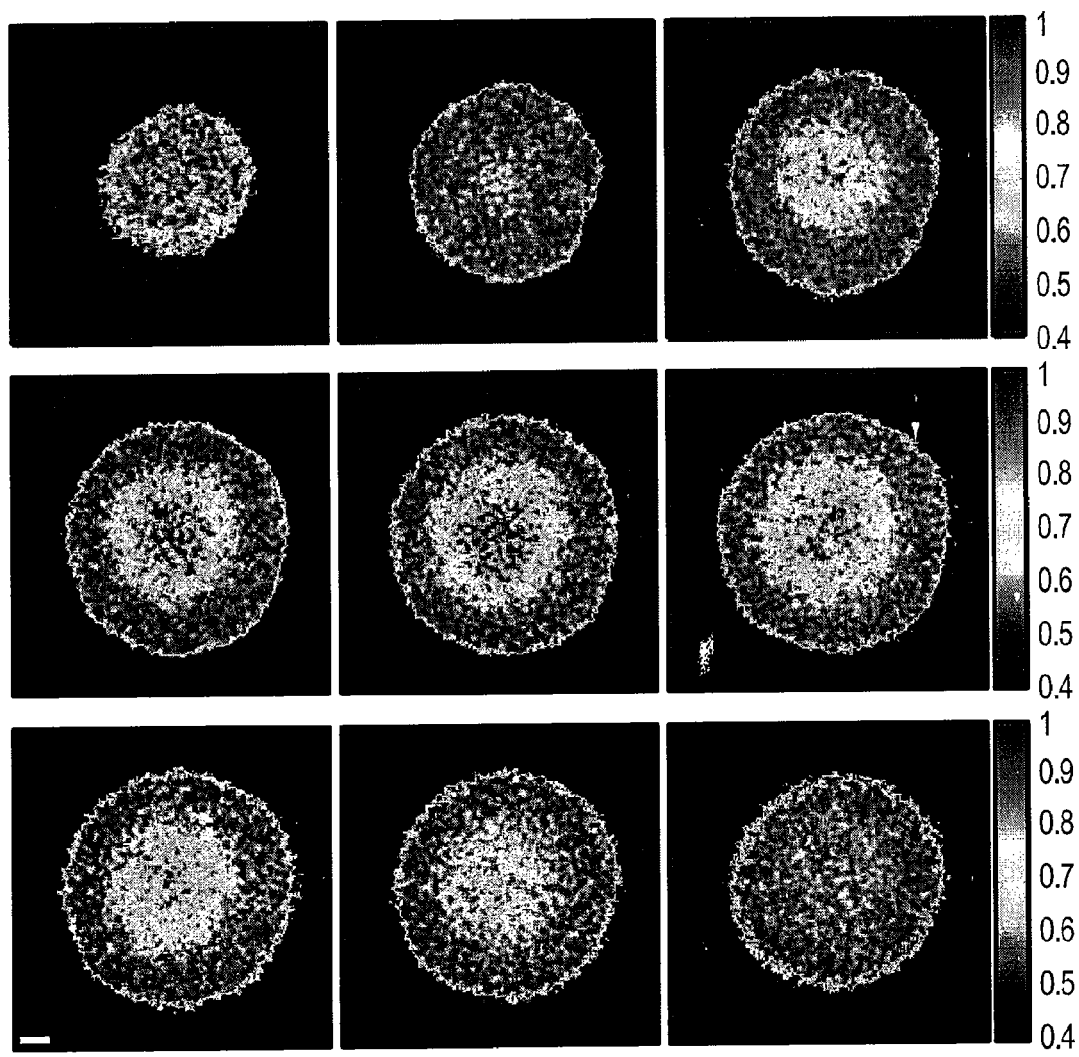
FIG. 11 shows color-coded motility metric of a healthy tumor at selected depths where the healthy outer shell shows strong cellular or sub-cellular motion, while the necrotic core is quiet.

Among the several possible ways to define a motility metric, one particularly robust approach simply calculates the coefficient of variance (known as the CV or as the normalized standard deviation) of a pixel value (after background subtraction) as a property related to the cellular and subcellular motion. The motility metric for individual pixels is plotted in FIG. 11 at nine selected depths inside a healthy tumor. The depths starting in the upper-left are 60 µm, 120 µm, 180 µm, 260 µm, 330 µm, 390 µm, 460 µm, 530 µm and 600 µm, respectively. The first frame is near the top of the tumor, while the central frame is near the center plane of the tumor. In the central plane there is a strong contrast between the healthy shell and necrotic core. The healthy shell appears highly motile, while the necrotic core shows low dynamic light scattering. These images correlate with the known structure of the tumor spheroids with a healthy outer shell and a necrotic core. In these images, the internal motions of the cells themselves have provided the imaging contrast agent. This is a truly endogenous functional imaging approach (i.e. without additional labeling or contrast agents).

Figure 12:
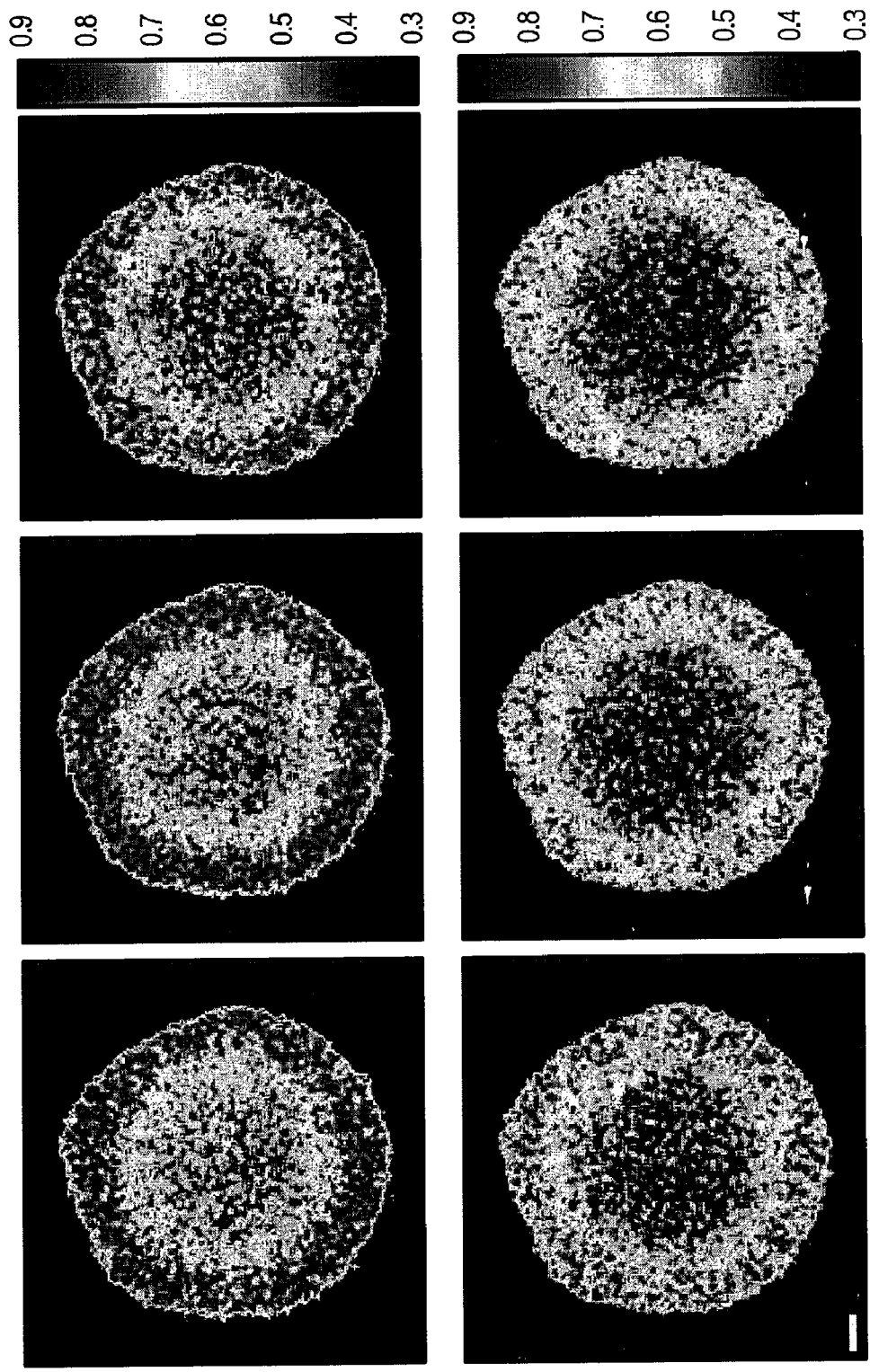
FIG. 12 shows motility maps of a tumor responding to 2 µg/ml of the anti-mitotic drug Nocodazole as a function of time from the initial state (first frame) to 119 minutes after the dose.

Armed with the motility metric and the maps of cellular motion, it is possible to image the effects of anti-mitotic drugs (AMD) on the motility images. A time series at a fixed depth is shown in FIG. 12 for Nocodazole, which is an antimitotic drug (AMD) that inhibits the polymerization of tubulin into microtubules. The first frame is the initial state of the tumor. By 3 minutes after application of 2 µg/ml of Nocodazole (second frame), the outer shell has increased its activity by a small amount. However, by 21 minutes (third frame) the motion is partially suppressed, and continues to be further suppressed at 50 minutes (fourth frame) and 79 minutes (fifth frame) until by 119 minutes after application of the drug (sixth frame), the motility in the outer shell has been significantly reduced. Nocodazole inhibits the polymerization of the microtubules, while treadmilling dissolves the microtubules from the other end, resulting in a significant reduction in the microtubule density within the cells. Without the microtubule cytoskeleton, organelle transport is suppressed, which is captured by the dynamic light scattering.

Figure 13A:
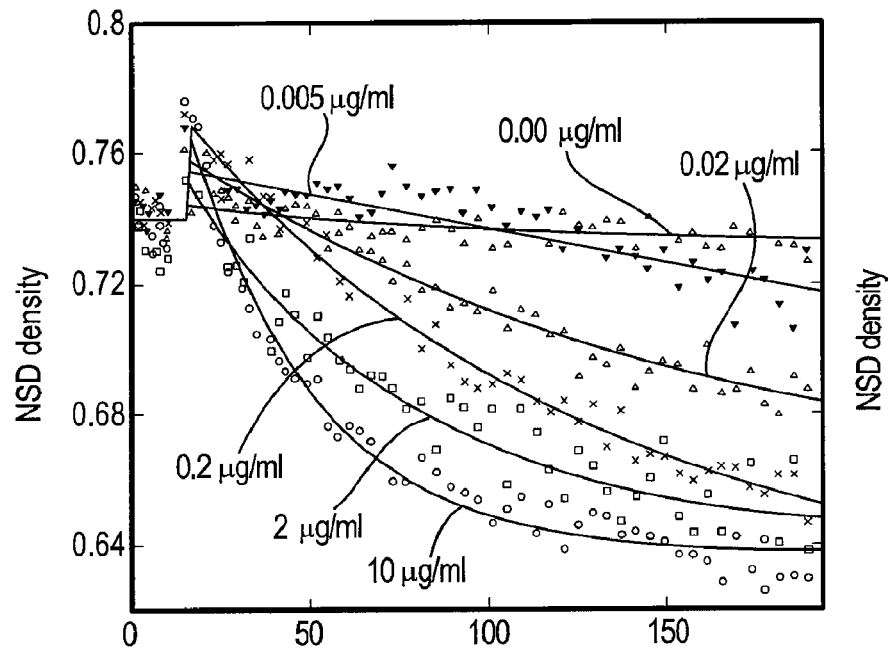
FIG. 13 shows time course of tumor responses as a function of dose for Nocodazole in FIG. 13(a), Colchicine in FIG. 13(b), Taxol (Paclitaxel) in FIG. 13(c), and the dose responses plotted as a reaction velocity in FIG. 13(d)
Figure 13B:
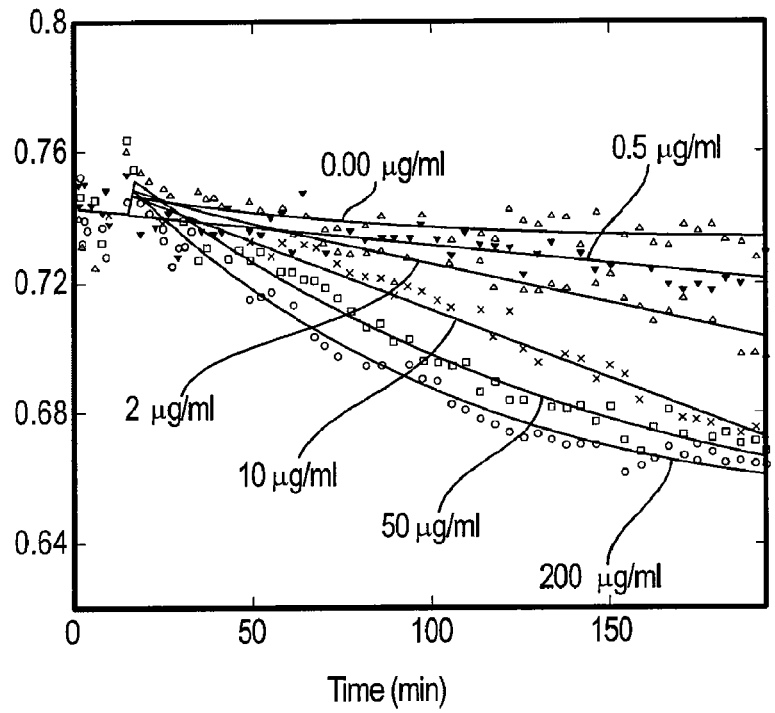
Figure 13C:
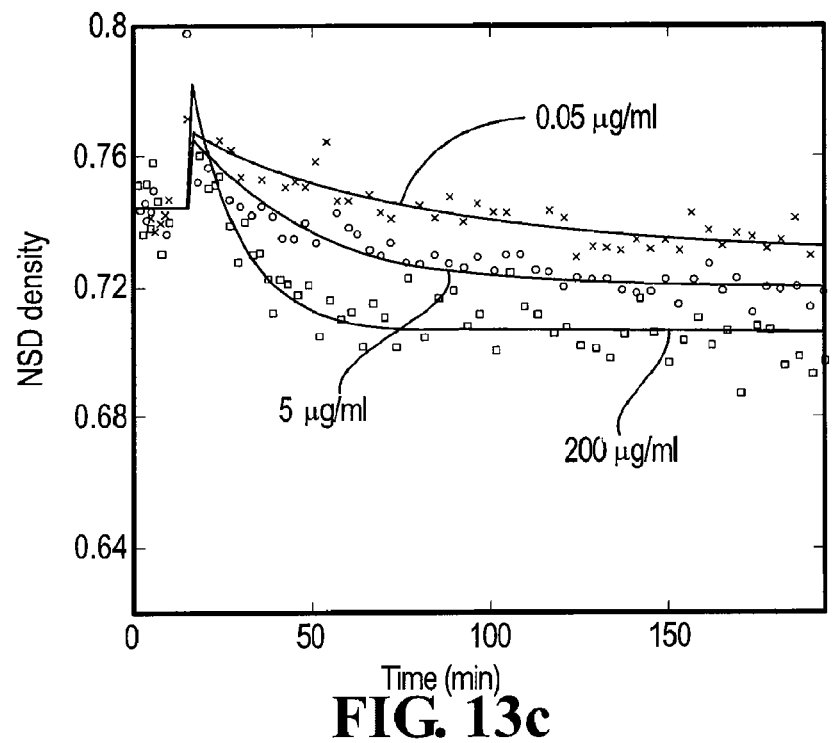
Figure 13D:
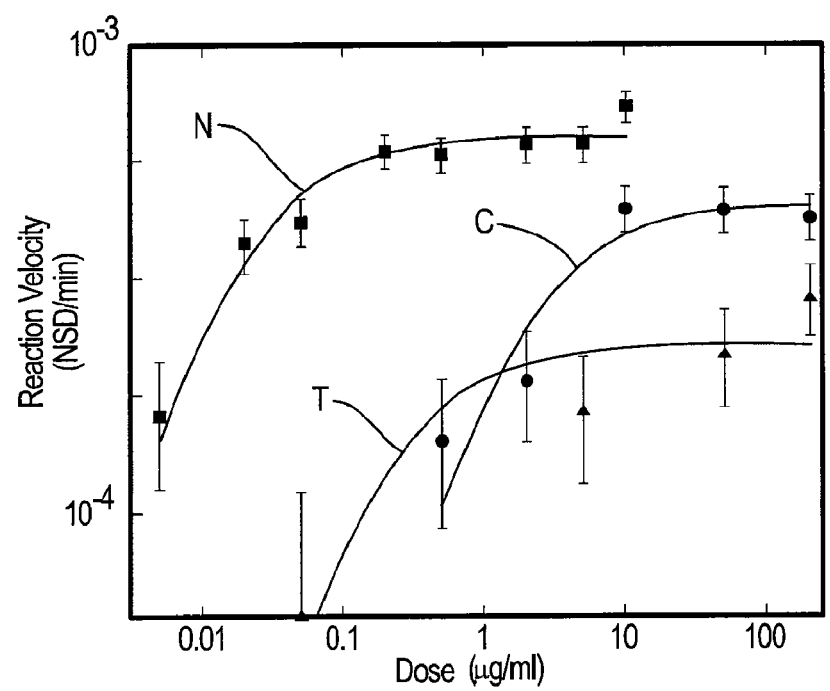

Time evolution under different doses is shown for Nocodazole in FIG. 13(a), for Colchicine in FIG. 13(b), and for Taxol in FIG. 13(c). Nocodazole is a synthetic variant to the natural Colchicine with higher potency. Taxol, on the other hand, operates by inhibiting depolymerization of the microtubules back into tubulin. This stabilizes the microtubules, keeping them available for organelle transport, but shutting down the cell cycle by preventing mitosis. For this reason, Taxol has less chemotherapeutic side effects. This is observed in the significantly smaller suppression of the motility in response to the Taxol. The dose-response curves for the three drugs Nocodazole (N), Colchicine (C), and Taxol (T) are plotted as a reaction velocity in FIG. 13(d). Taxol shows the weakest effect, consistent with the stabilization of the microtubules, while Nocodazole shows the strongest suppression of cellular motion at the lowest effective concentrations. The results of FIGS. 12 and 13 show the specific sensitivity that motility contrast imaging has to the cytoskeleton.

The above describes various aspects of the physical and biological phenomenon. Additional details relating to previously used apparatus that may be of use in the apparatus and/or methods disclosed herein are disclosed in International PCT Application Serial No. PCT/US2009/0362124 titled "Method And Apparatus For Motility Contrast Imaging" filed on 5 Mar. 2009 that published on 11 Sep. 2009 as WO 2009/111609 A2. The discussion below is of an aspect of the present invention in which the apparatus potentially provides increased stability over the apparatus described in the just mentioned PCT application.

Digital Holographic Apparatus With Improved Stability

The various configurations below can provide improved stability in a holographic apparatus for motility contrast imaging.

Off-Axis Holography

Figure 14:
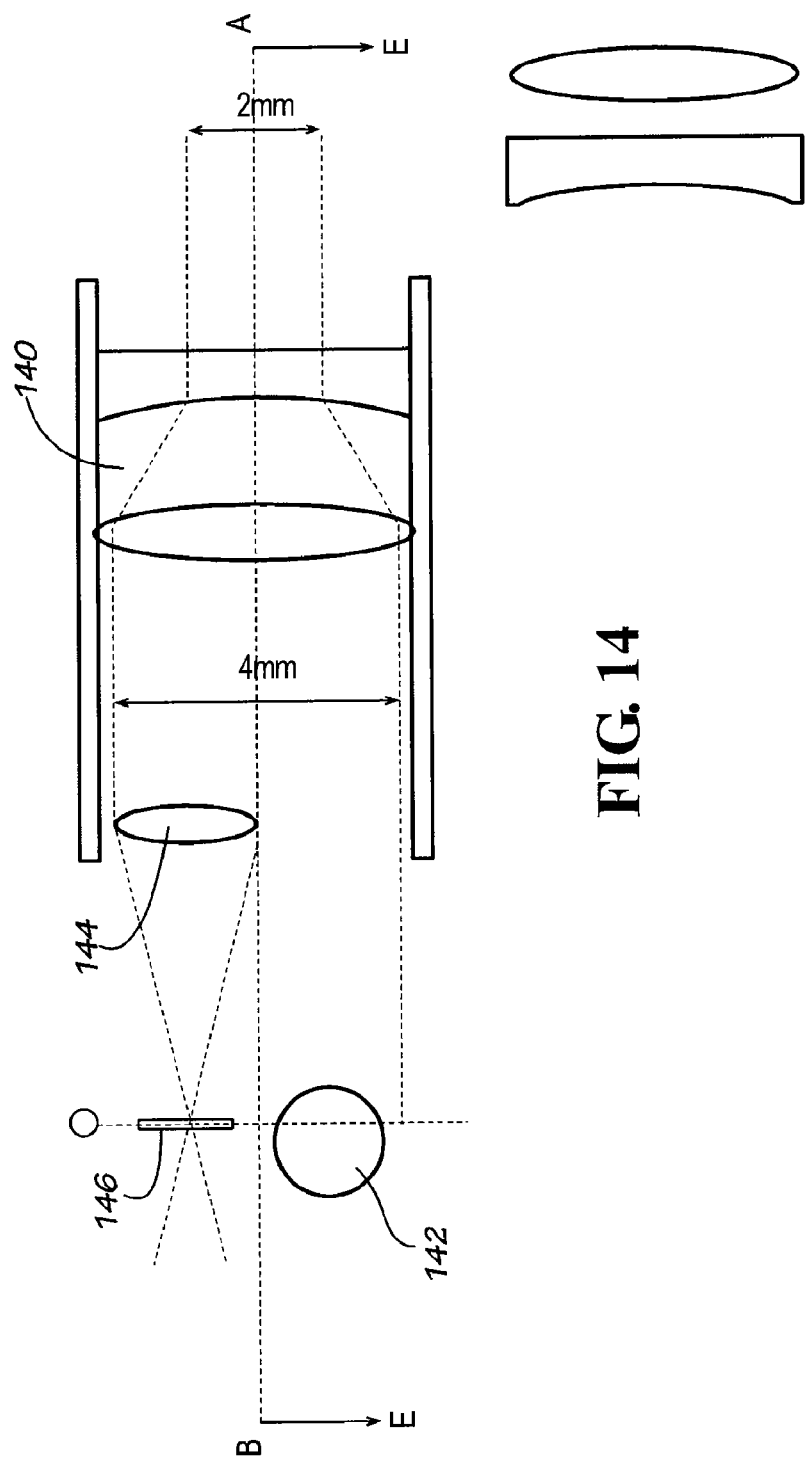
FIG. 14 shows an illuminator for stable holography at a fixed depth where the input beam at A is expanded by a factor of 2 using a cylindrical beam expander and the expanded beam exposes the tumor and passes through a cylindrical lens that focuses the reference arm onto a mirror in the sample well.
Figure 16:
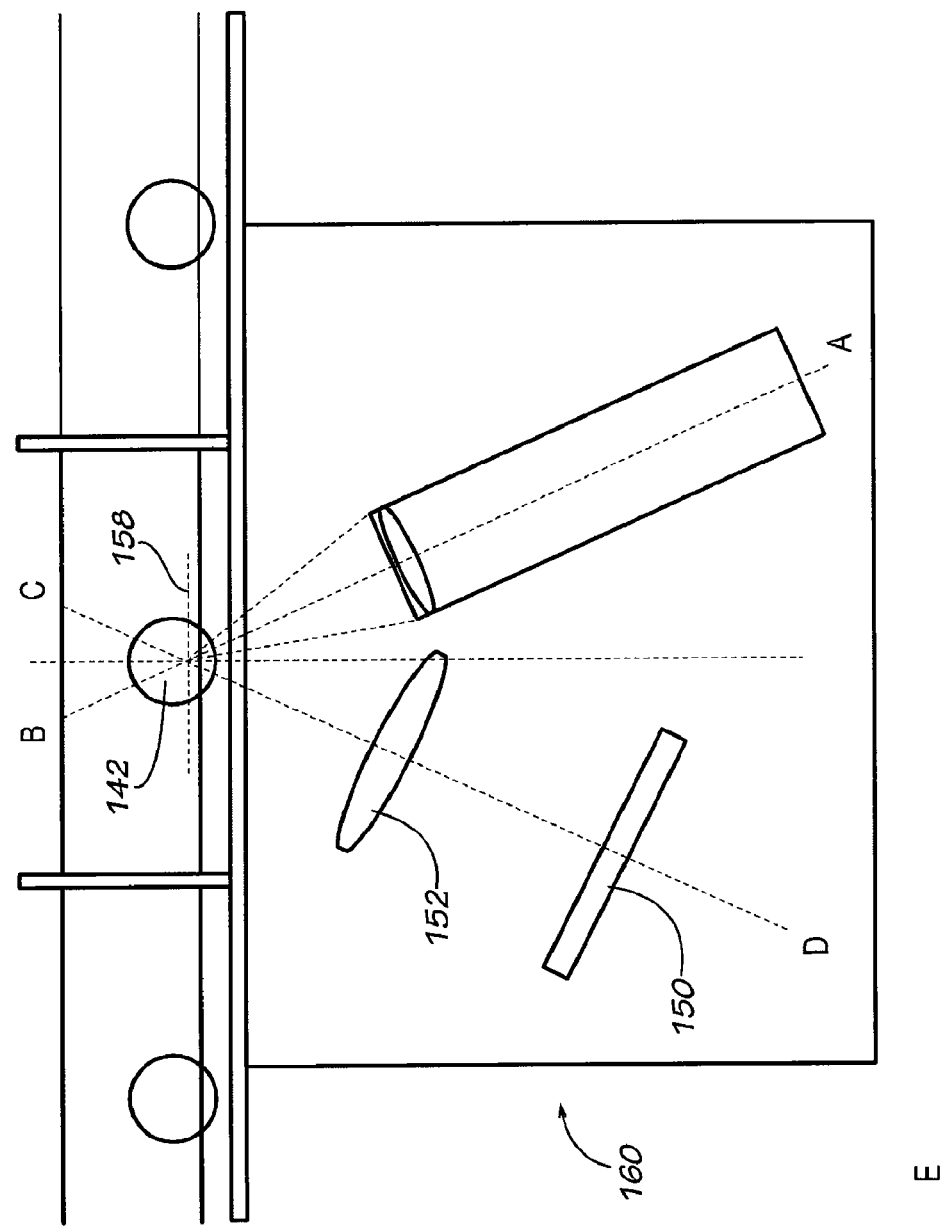
FIG. 16 shows a side-view of the illumination and detection systems of FIGS. 14 and 15 where the mirror on the bottom of the well is behind the tumor on the detection plane and the read head is on a translation stage that moves from well-to-well.

FIGS. 14-16 disclose an exemplary embodiment of a lens-based apparatus, a free-space holographic system. FIG. 14 shows an illuminator section and FIG. 15 shows a detection portion of the system for stable holography at a fixed depth. In FIG. 14, an input beam at A is expanded by a factor of two using a cylindrical beam expander 140. The expanded beam exposes a tumor 142 and passes through a cylindrical lens 144 that focuses the reference arm onto a mirror in the sample well.

In FIG. 15(a) the reference arm expands off the mirror 146 of the sample well and is collimated by the Fourier-transform (FT) lens 152. The light scattered from the tumor 142 is collected and transformed to the Fourier plane at the CCD chip 150. There is a crossing angle between the reference and the signal arm, providing the carrier frequency for the digital holography. FIG. 15(b) shows an exemplary sample well 154 containing the mirror 146 adjacent to the tumor 142 positioned in a growth medium 156 and indicating a sample plane 158.

FIG. 16 shows a side-view of both the illumination and detection systems of FIGS. 14 and 15. The mirror 146 on the bottom of the well 154 is behind the tumor 142 on the sample plane 158. The read head 160 is on a translation stage that moves from well-to-well.

Figure 17:
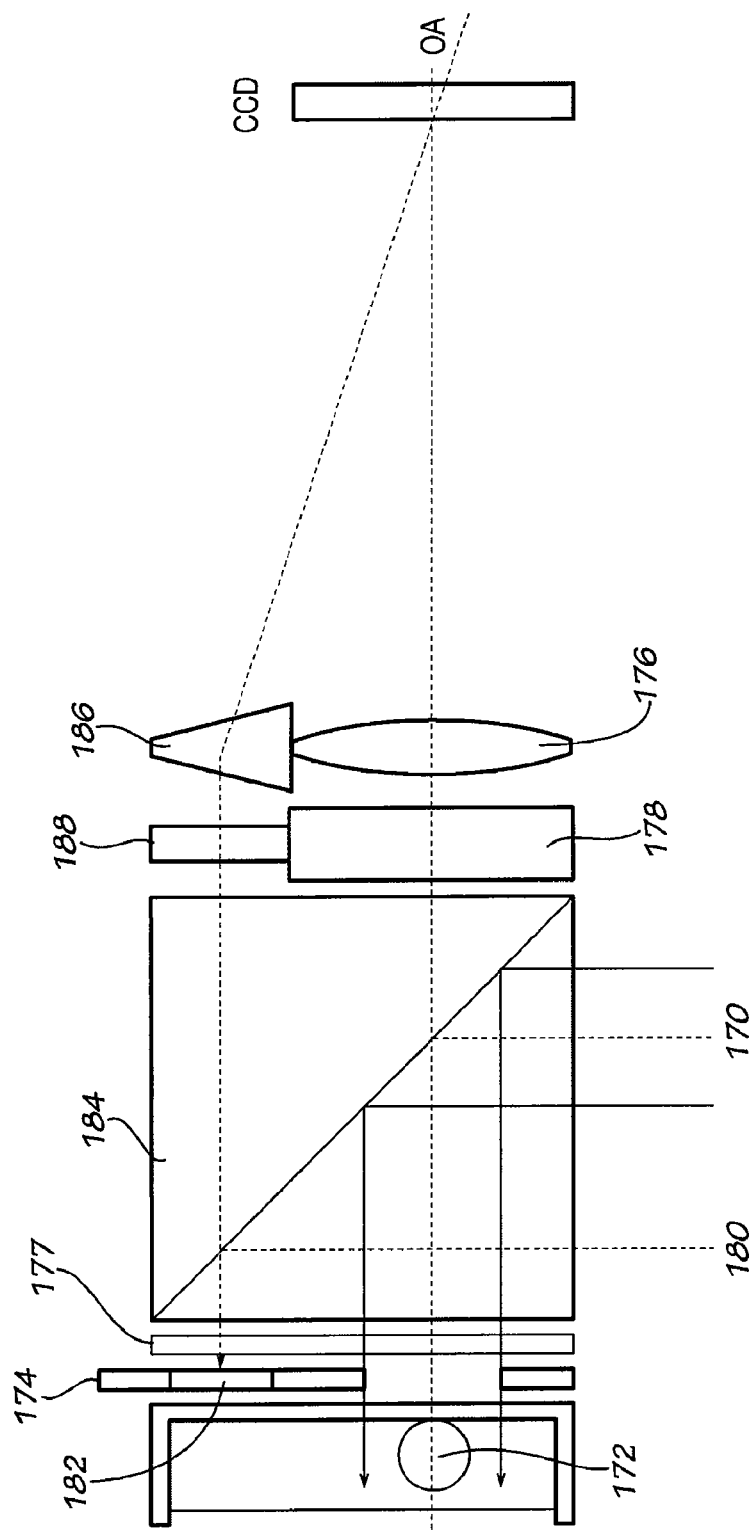
FIG. 17 shows an Upniets-Leith holography system reconfigured to capture backscattered holograms with a coherence gate where the path difference between the reference and the signal arms is compensated by the two dielectric plates of different thicknesses to adjust the depth gate within the 1 mm depth of the target tumor, and the tumor plate is tilted to prevent specular reflections from the plate reaching the CCD chip.
Figure 18:
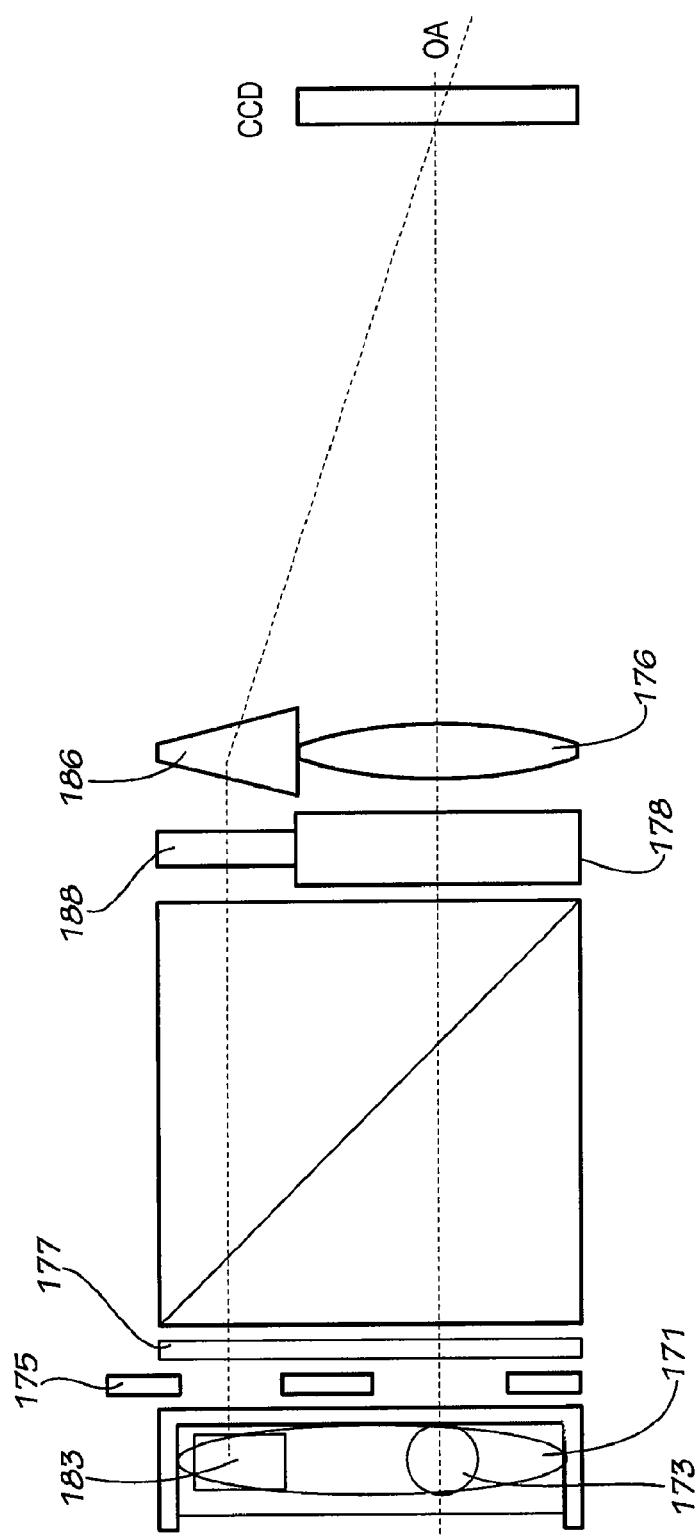
FIG. 18 shows a side-illumination version of the Upniets-Leith holography configuration where the beam is incident on the plane of the drawing extending over the tumor target and the 45-degree reference mirror, the reference wave and the side-scattered light from the target are passed through the opaque aperture mask, and the scattered light is transformed to the CCD plane while the reference wave is deflected by the prism and the slight path mismatch is compensated by the compensation plates.

FIGS. 17-18 show a prism-based holography that is a coherence-gated Upniets-Leith (UL) configuration for stable transmission of holograms. The UL holography system is reconfigured to capture backscattered holograms with a coherence gate. In this configuration, a reference wave is deflected by a prism that is adjacent laterally to a lens. The reference wave remains unfocused and provides the reference at the hologram plane.

To enable the UL holography configuration to perform depth-gated (coherence-gated) holography in reflection, a compensated path length is created between the target path and the reference path. This coherence-gated configuration is shown in FIG. 17. In this configuration, the optic axis OA of the illumination beam 170 is deflected by a polarizing beam splitter 184, passes through a λ/4 plate 177 and an opaque aperture mask 174, and falls upon the target 172. The signal beam scatters from the target 172, passes back through the opaque aperture mask 174 and the λ/4 plate 177, and then through the polarizing beam splitter 184 and a Fourier transform lens 176 along the optic axis OA to the CCD plane. A side-lobe of the illumination beam 180 forms the reference beam which is deflected by a polarizing beam splitter 184, passes through the λ/4 plate 177 and is incident on a mirror 182 that is embedded in the opaque mask 174. The reference beam reflects off the mirror 182, passes through the λ/4 plate 177 and the polarizing beam splitter 184 and is deflected by a prism 186 (adjacent to the lens 176) to intersect the optic axis OA at the CCD plane. Because the reference arm travels a longer path, this path is compensated by two means. First, the mirror 182 is placed advanced relative to the target 172. Second, two dielectric plates 178, 188 are placed in the signal and reference paths, respectively. These plates 178, 188 are anti-reflection-coated optical flats that balance the optical path length between the signal and reference arms to define the depth of the coherence-gated section. In alternative embodiments, a birefringent compensator may be used to help compensate for the path differences. A nominal depth inside the tumor would be 100 to 500 microns deep. This depth can be changed by selecting different path-length plates. The well holding the tumor 172 can be tilted to prevent specular reflections from the well from reaching the CCD chip.

Because of the importance of angular dependence on scattering, a side-scattering configuration of the UL holography system is shown in FIG. 18. The illumination can be either a Gaussian centered on the target with a side-lobe reflected by a 45-degree mirror as the reference, or the incident beam can be a cylindrical beam (shown in figure) to allow stronger reference-arm intensity. The light reaching the Fourier plane at the CCD is scattered at 90-degrees compared with the backscattering configuration of FIG. 17.

FIG. 18 illustrates a side-illumination version of the UL holography configuration. The beam 171 is incident on the plane of the drawing, extending over the tumor target 173 and a 45-degree reference mirror 183. The reference wave and the side-scattered light from the target are passed through the opaque aperture mask 175. The scattered light is transformed by the Fourier transform lens 176 to the CCD plane, while the reference wave is deflected by the prism 186. As in the embodiment of FIG. 17, the slight path mismatch is compensated by the variable compensator 178, 188.

In-Line Holography

Off-axis holography provides many improvements in terms of stability over free-space Mach-Zehnder or Michelson interferometers. However, there are still two separate beams, and even though they pass through the same optical elements, they do not share a common optic axis. Therefore, an in-line configuration may have further advantages for stability because it is a common-path configuration in which the optical beams share a common optic axis and hence will share all phase perturbations in common.

Figure 19A:
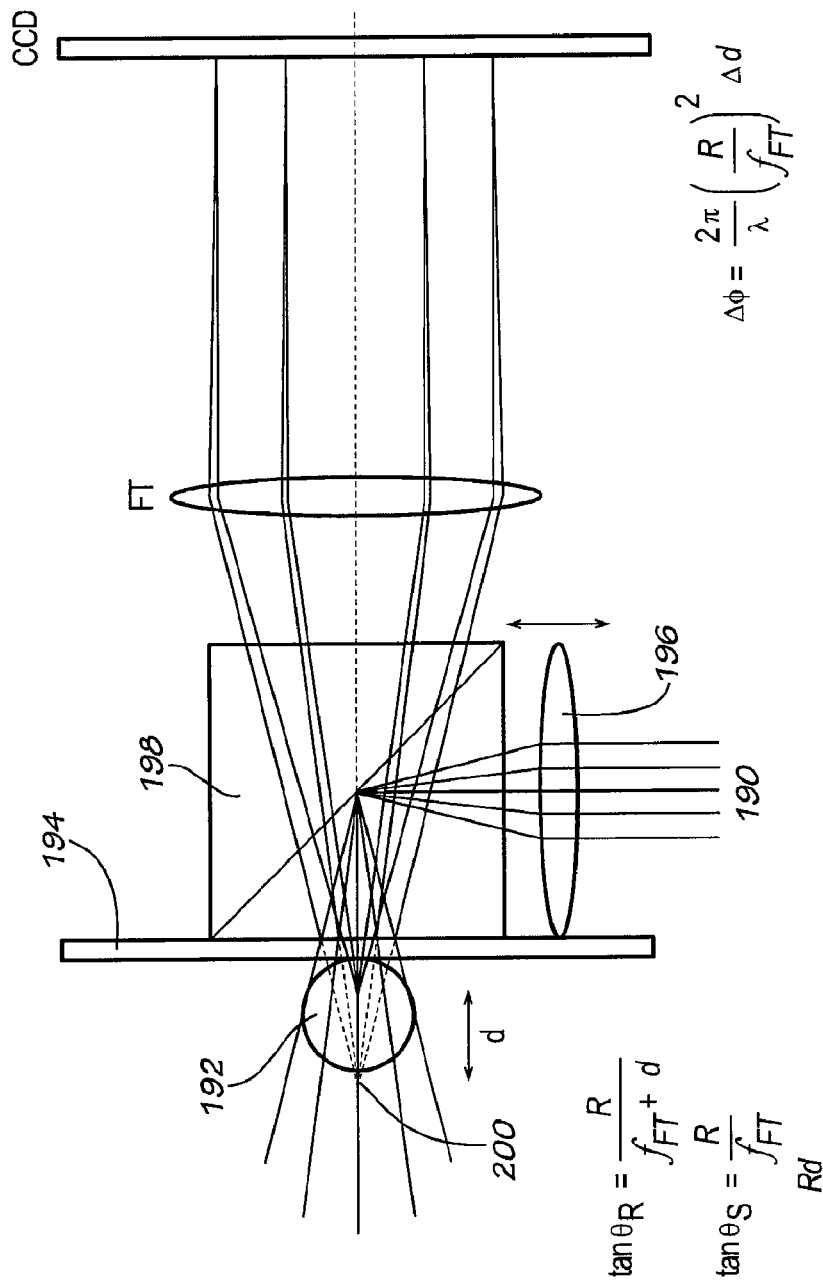
FIG. 19(a) shows an apparatus to write Fourier-domain holograms with a depth gate and speckle modulation where the depth gate is set by the time-delay between a leading and a trailing pulse, the tumor scatter of the leading pulse interfering with the trailing pulse reflected from the glass surface, and the double pulse is generated in a fiber Mach-Zehnder with a variable time delay, and the speckle on the CCD is modulated by moving the lens.
Figure 19B:
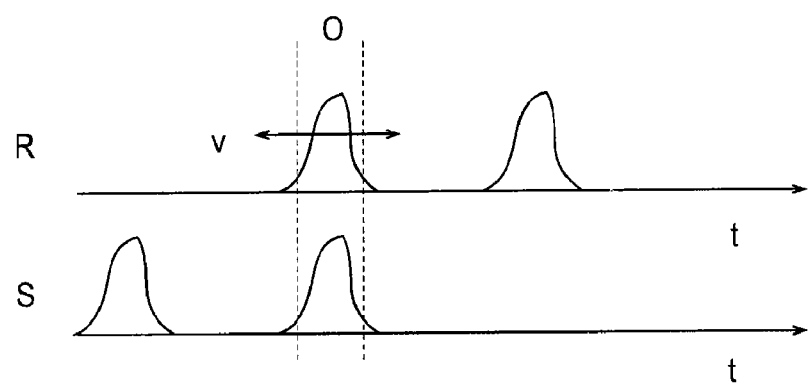
FIG. 19(b) shows a double pulse.

A schematic of an in-line Fourier-transform holographic optical coherence imaging system is shown in FIG. 19(a). The excitation beam 190 uses a pulse pair that is generated in a stable Mach-Zehnder (fiber-optic) with a variable delay. The leading pulse is deflected by a beam splitter 198 and propagates into the target 192 and scatters back. This backscattered signal is time-coincident with a trailing pulse that reflects off the coverslip 194. The depth gate is set by the time-delay between a leading and a trailing pulse. This time coincidence (or path coincidence for a broadband non-pulsed light source) defines the depth (or coherence) gate for the information coming from the target 192. The excitation beam 190 is focused in front of the tumor 192, which, when reflected by the beam splitter 198 and by the coverslip 194, creates a virtual point reference image 200 that lies on the far side of the coherence-gated depth. The return beams from the tumor 192 and the virtual reference image 200 pass through an FT lens and onto a CCD plane. This virtual reference image 200 interferes on the CCD plane with the speckle coming from the target 192. Only signal coming from the gate-selected depth will show interference, while the rest of the scattered light forms an incoherent background. This background can be subtracted by moving the depth gate out of the scattering volume. FIG. 19(*b*) shows a representation of the double pulse excitation where the signal pulse S and the reference pulse R have an overlap region O with variable delay v. The horizontal axis is time t. The speckle on the CCD can be modulated by moving a lens 202.

The speckle diameter on the CCD is $$d_s = \frac{f_{FT}\lambda}{D_{FT}} = \frac{f_{FT}\lambda}{2R_{max}}$$

where $D_{FT}$ is the diameter of the FT lens, which is twice the maximum radius at the CCD. The excitation beam radius before the focus lens to fill the CCD would be $$a = \frac{f_f R_{max}}{(f_{FT} + d)}$$

where a is the radius of the original excitation beam before the focus lens.

If we want fringes within the speckles, there should be at least 3 fringes within a speckle diameter $$d_s > 3\Lambda$$
$$> 3\lambda \frac{f_{FT}^2}{Rd}$$

but this leads to the condition on the detection radius (on the CCD)

$$R > 6 \frac{f_{FT}}{d} R_{max}$$

which is not feasible.

The phase can be modulated by moving the focus lens. The phase modulation is $$\Delta\phi = \frac{2\pi}{\lambda} \frac{R^2}{2(L+d)^2} \Delta d$$

Therefore, there are two ways of gating on the coherence. Moving the mirror causes phase modulation (that depends on the square of the detection radius) that can be captured in successive frames and differenced. As an alternative to modulating the phase by moving the lens, the double pulse delay can be adjusted to move the gated depth out of the scattering volume. Or both approaches can be used to find which speckles are coherent with a selected depth, and removing the incoherent background.

Preliminary Discussion of Using Speckle Fluctuation Spectroscopy

Having generally described various apparatus, we now describe a method of obtaining a "fingerprint" of the impact of a change in environment (including, but not limited to, administering a drug) on cells in tissue using speckle fluctuation spectroscopy of intra-cellular motion in living tissue by coherence-domain digital holography. While the more mechanically stable motility contrasting imaging apparatus described herein is preferred, other less stable apparatus might also be used in the methods of the present invention.

To briefly summarize aspects of one method, dynamic speckle from three-dimensional coherence-gated optical sections provides a sensitive label-free measure of cellular activity up to 1 mm deep in living tissue. However, specificity to cellular functionality has not previously been demonstrated. Described below are the results of fluctuation spectroscopy on dynamic speckle captured using coherence-domain digital holography to obtain the spectral response of tissue that is perturbed by environmental factors such as temperature, osmolarity, and anti-mitotic cytoskeletal drugs. Different perturbations induce specific spectrogram response signatures that can show simultaneous enhancement and suppression in different spectral ranges.

Biological speckle has a dual character. On the one hand, it is a parasitic effect that degrades the contrast of biomedical imaging, and many approaches seek speckle reduction. On the other hand, static speckle provides strong statistical information about scattering media and can be used for interferometric imaging of cells. Dynamic speckle, in particular, has considerable information content. For instance, dynamic speckle can be used to monitor blood flow and can assess the health of living tissue using intracellular motion as a fully endogenous imaging contrast agent. Three-dimensional imaging approaches are particularly important for assessing tissue viability, pharmacological toxicity, and cancer progression, and can be provided by coherence-domain techniques and digital holography. Holography captures high-contrast depth-gated speckle statistics because of broad-field illumination.

Coherence-gated digital holography was used to capture intracellular motion in three-dimensional tissue as an imaging contrast agent based on the statistical fluctuations of dynamic speckle. However, there are many functional causes of subcellular motion, and an overall motility metric does not capture specific functions. Thus, fluctuation spectroscopy can be performed on depth-gated dynamic speckle to generate frequency vs. time spectrograms of tissue responding to various environmental and pharmacological perturbations. The spectral responses depend on the specific type of perturbation, and these spectral responses can serve as functional fingerprints for tissue-based screening.

Figure 20:
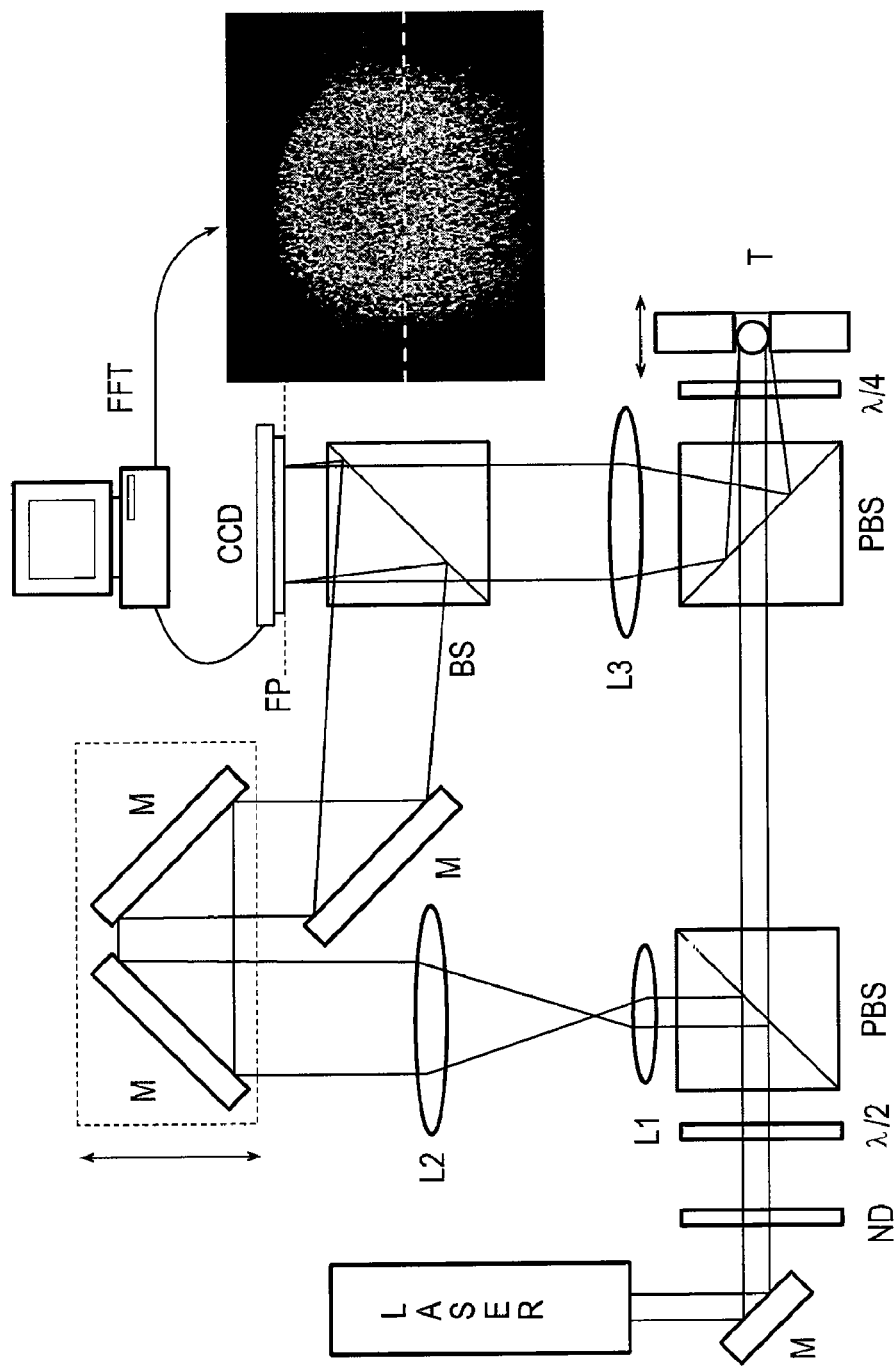
FIG. 20 shows an experimental set-up where M is a mirror, ND is a neutral density filter, PBS is a polarizing beam splitters, BS is a beam splitter, L1-L3 are lenses, λ/2 is a half-wave plate, λ/4 is a quarter-wave plate, FP is the Fourier Plane, and FFT is a fast Fourier transform.

Holograms in short coherence digital holography were recorded and reconstructed from the experimental set-up shown in FIG. 20. The set-up includes several mirrors M; a neutral density filter ND, two polarizing beam splitters PBS, a beam splitter BS, three lenses L1-L3, a half-wave plate λ/2, a quarter-wave plate λ/4, a Fourier plane FP, and a sample or target T. A mode-locked Ti:sapphire laser (100 fs pulse duration, 100 MHz repetition rate) was used with a center wavelength of 840 nm and a bandwidth of 17 nm. The lenses L1 and L2 expanded a reference beam, and the lens L3 performed the Fourier transform of the object beam. The CCD camera was placed at the Fourier plane of the object, where the object beam interfered with the zero-path-matched reference beam that passed through the computer-controlled delay line. The typical object intensity for living tissue at the object plane was 5 mW/mm², and an 8-bit CCD camera with one mega-pixel resolution was used with an exposure time of 10 msec. Digital holograms were reconstructed by Fast Fourier transform (FFT).

Rat osteogenic sarcoma tumor spheroids were used as the target tissue samples. Multicellular tumor spheroids have approximately spherical geometry that facilitates comparison of structure to function. As tumor spheroids are cultured in a rotating bioreactor, they undergo cell apoptosis or necrosis in their center and so consist of an inner necrotic core surrounded by an outer proliferating shell with a 100 to 200 μm thickness. A typical pseudo B-scan image is shown in FIG. 20, which is produced from 3D holographic images of an 800-μm-diameter rat tumor spheroid.

Figure 21A:
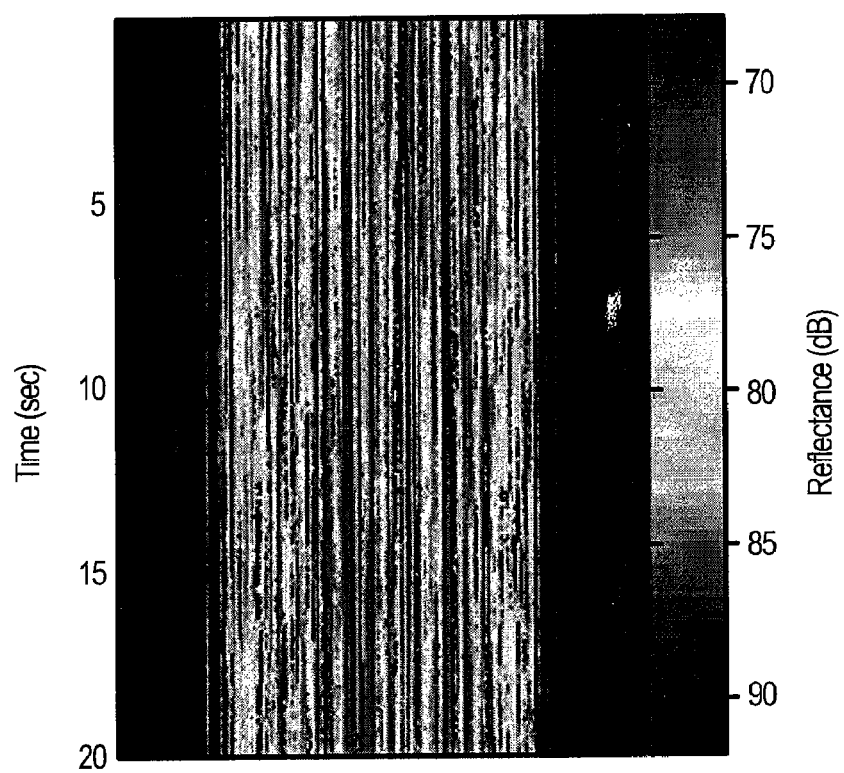
FIG. 21(a) shows a mid cross-section image reconstructed from successive digital holograms of a 600-μm-diameter healthy tumor at a fixed depth of 310 μm.

To capture dynamic speckle, 200 successive digital holograms were acquired at a fixed depth shown as a dashed line in FIG. 20. The time interval between holograms was selected to be 0.1 second. Examples of dynamic speckle are shown in FIG. 21(a) for a healthy rat tumor spheroid with a 600 μm diameter. FIG. 21(a) shows a mid cross-section image reconstructed from successive digital holograms of a 600-μm-diameter healthy tumor at a fixed depth of 310 μm. The horizontal axis is the spatial axis and time is vertical. The holographically reconstructed high-contrast speckle shows dynamic character as individual speckle intensities fluctuate strongly. A "healthy" tumor is one that has been removed from the bioreactor and maintained in growth medium at room temperature for no more than 24 hours.

The two equivalent approaches to time-series analysis of fluctuating speckle are temporal autocorrelation and power spectra. Autocorrelation of holographic speckle yields a first-order heterodyne function because holography uses a reference wave (the coherence gate) that captures the real and imaginary parts of the fluctuating field as the coherence-gated pixel number $i_d^{(1)}(t)$. The autocorrelation function is $$A^{(1)}(\tau) = \langle i_d^{(1)}(0) i_d^{(1)}(\tau) \rangle \propto I_{LO}^2 + 2 I_{LO} Re\{I^{(1)}(\tau)\} \quad (1)$$

where τ is the time delay among an ensemble of images, and $I^{(1)}(\tau)$ is the heterodyne correlation function. Our previous motility metric was defined from the heterodyne correlation function as the normalized standard deviation, or speckle contrast, given by $$NSD = \left( \frac{2Re\{I^{(1)}(\tau_{max}) - I^{(1)}(0)\}}{I_{LO}} \right)^{1/2} \quad (2)$$

Autocorrelation functions and power spectra are related through a Fourier transform. Although the autocorrelation function and the power spectrum contain identical information, the interpretation of that information is qualitatively different. In particular, the spectral information directly displays the presence of characteristic frequencies that can be related to biophysical processes, such as fluctuating membranes or organelle transport.

Figure 21B:
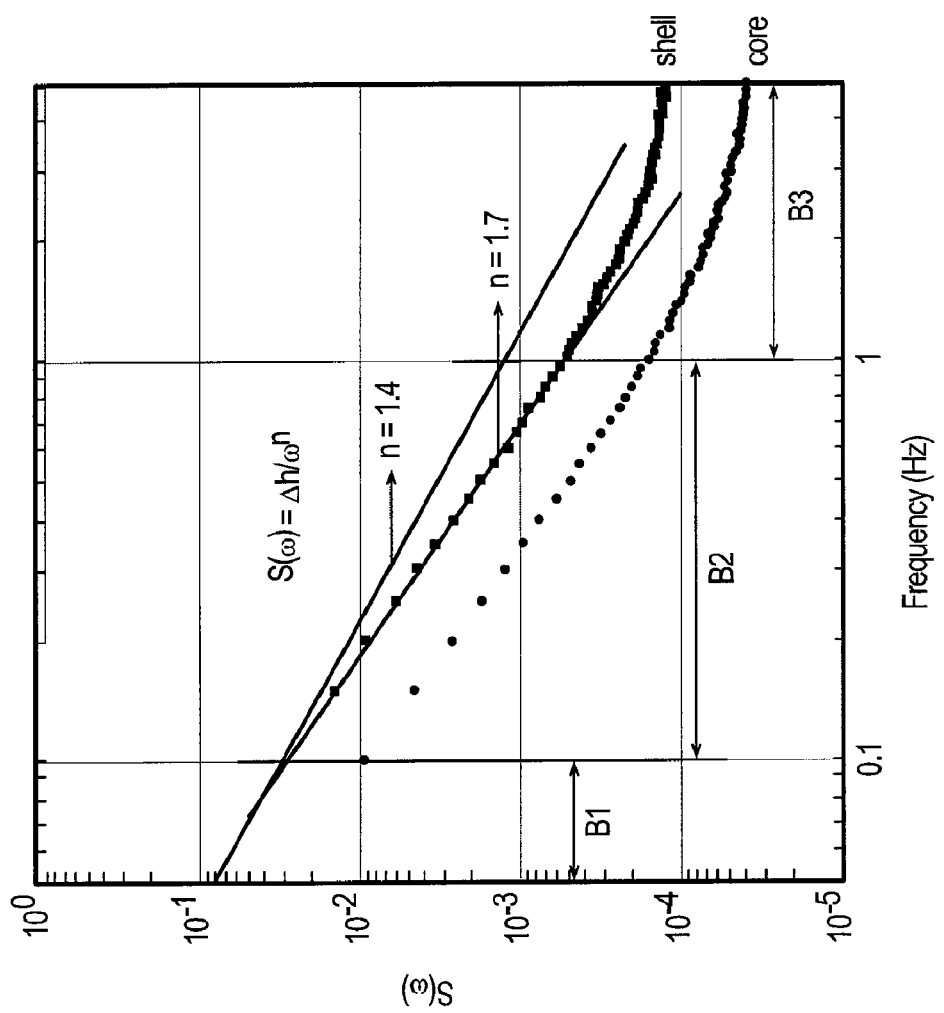
FIG. 21(b) shows the normalized power spectrum as a function of frequency comparing the proliferating shell with the necrotic core of the healthy tumor.

The spectral power density of a 600-μm-diameter tumor is shown in FIG. 21(b) for the proliferating shell and the necrotic core. FIG. 21(b) shows the normalized power spectrum as a function of frequency comparing the proliferating shell with the necrotic core of the healthy tumor. The power spectra exhibit $1/f^n$ behavior from 0.01 Hz to about 1 Hz with an exponent n of 1.7. The shell is significantly more active than the core, but part of the core activity can be ascribed to the shimmering showerglass effect from the dynamic overlying tissue layers. The slopes of the power spectral density show a break above 1 Hz, which is likely due to Nyquist sampling.

Figure 21C:
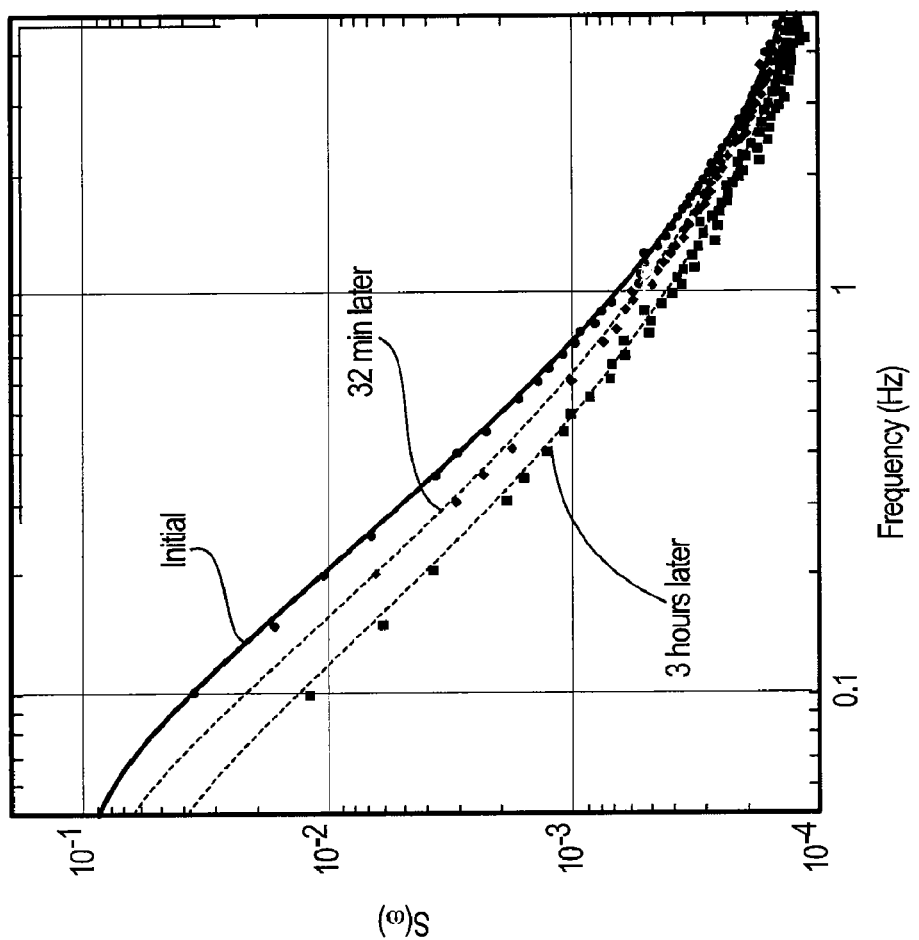
FIG. 21(c) shows the normalized power spectrum as a function of frequency at the selected times, in the proliferating shell after treatment with 1 μg/ml nocodazole.
Figure 21D:
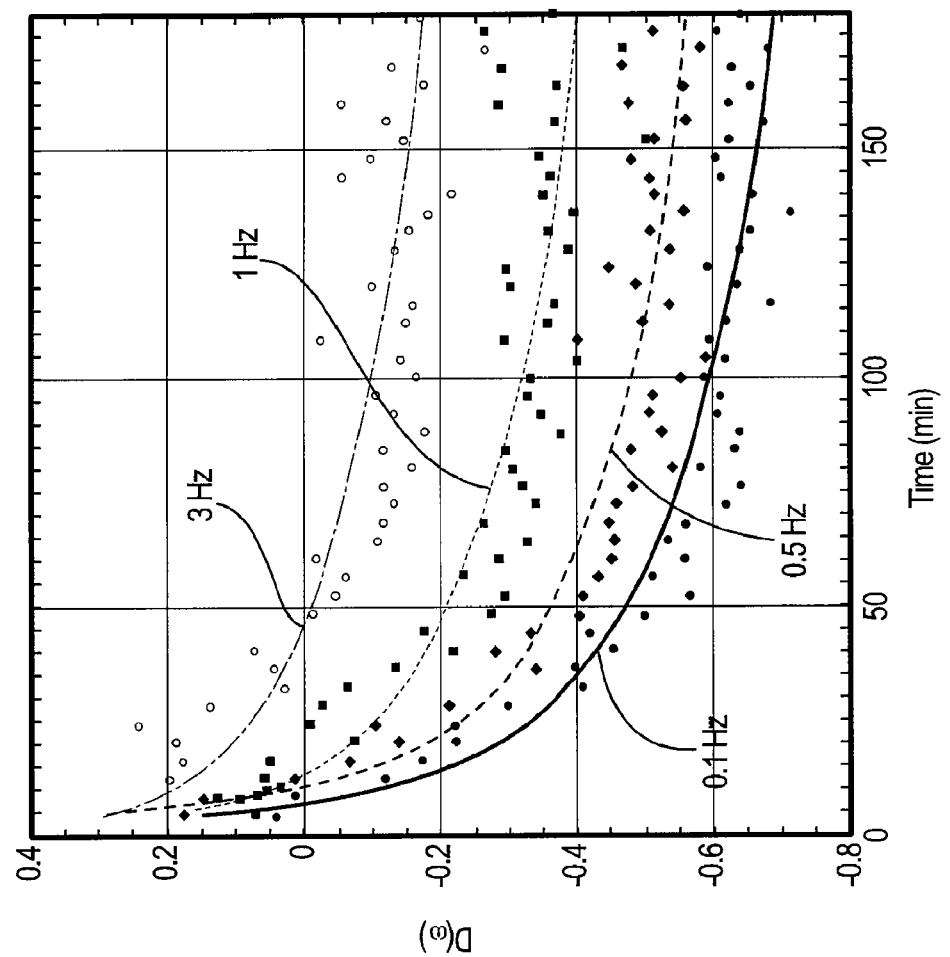
FIG. 21(d) shows the associated normalized spectral difference as a function of time at the selected frequencies.

For tissue responding to stimuli, such as temperature and osmolarity changes or response to drugs, the key property of the spectral power density is its relative change in response to the stimulus. The normalized spectral difference for a time series is given by $$D(\omega, t) = \frac{S(\omega, t) - S_0(\omega, t_0)}{S_0(\omega, t_0)} \quad (3)$$

where $S_0(\omega, t_0)$ is the starting spectral power density at the beginning time $t_0$ of the experiment, and $S(\omega, t)$ is the time development of the spectral power density. The normalized power spectrum as a function of frequency of a 450-μm-diameter tumor responding to a dose of 1 μg/ml of nocodazole, an anti-tubulin cytoskeletal drug, is shown in FIG. 21(c) at selected times after the application of the drug. The associated normalized differential relative spectral change is shown in FIG. 21(d) as a function of time for the selected frequencies. The higher frequencies change relatively less than the lower frequencies in response to nocodazole.

Figure 22A:
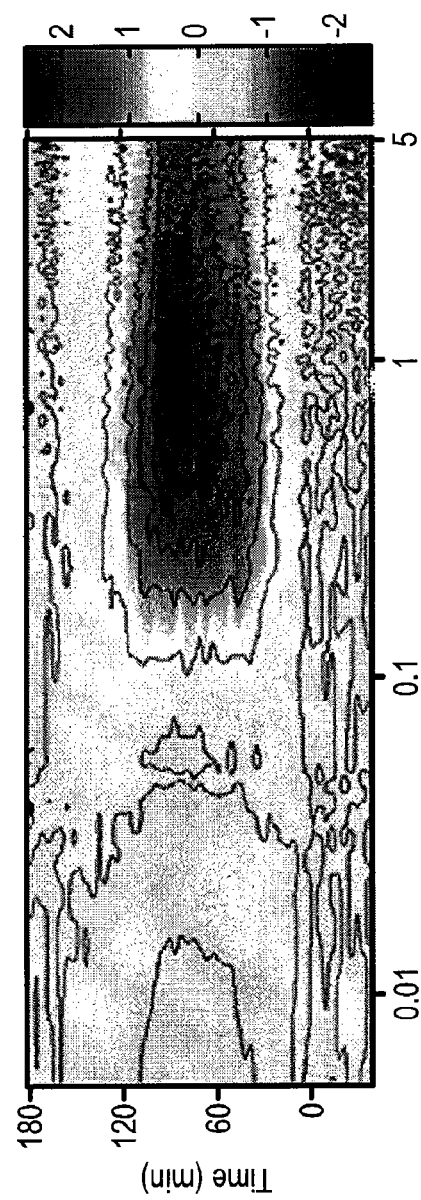
FIG. 22 shows maps of the normalized spectral difference as a function of time and frequency for thermal change in FIG. 22(a), hypotonic change of osmolarity in FIG. 22(b), hypertonic change of osmolarity in FIG. 22(c), and 1 μg/ml nocodazole in FIG. 22(d), and the differential relative spectral change as a function of time is shown at the frequency of 0.1 Hz in FIG. 22(e) and are the frequency of 1 Hz in FIG. 22(f)

The tissue response contained in $D(\omega, t)$ can be represented as a spectrogram, showing the relative change in the spectrum as a function of time. Examples of several spectrograms are shown in FIG. 22. These spectrograms track the changes of the intra-cellular motion in living tumors responding to temperature changes, osmolarity changes, and to nocodazole. The spectral difference in response to changes in temperature is shown in FIG. 22(a) as the temperature increased from 24° C. to 37° C. and then decreased to 24° C. The lower frequencies show weak suppression with increasing temperature, while the upper frequencies show significant enhancement at the highest temperature.

Figure 22B:
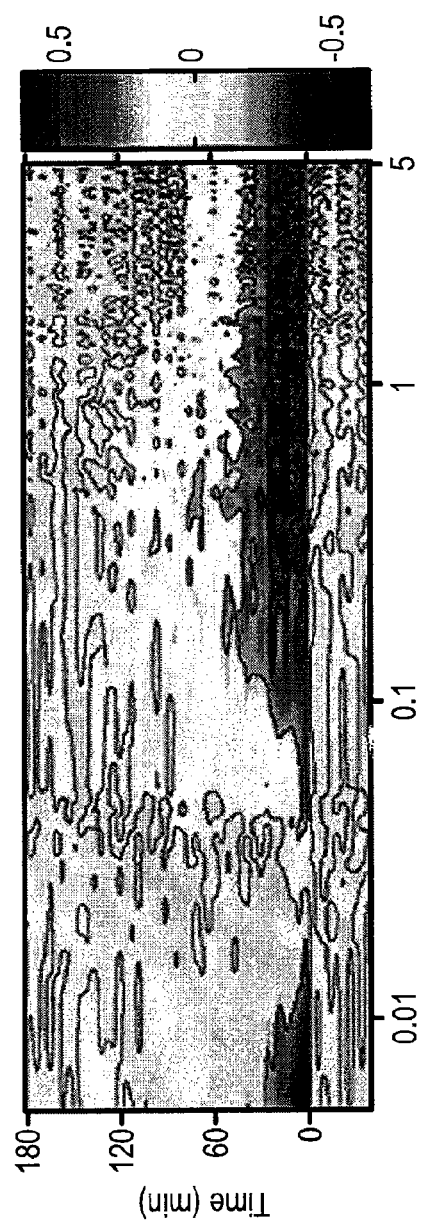
Figure 22C:
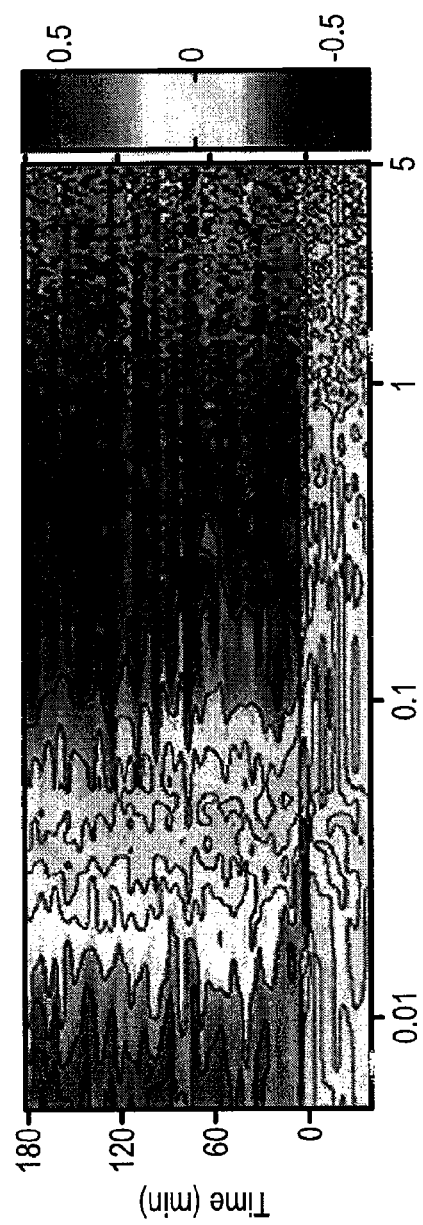
Figure 22D:
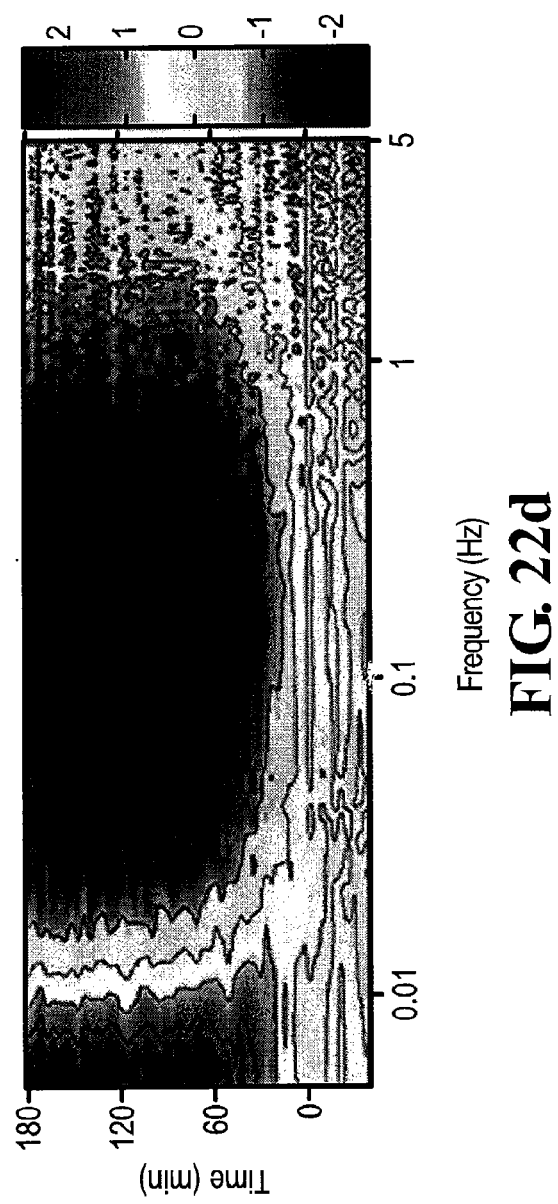
Figure 22E:
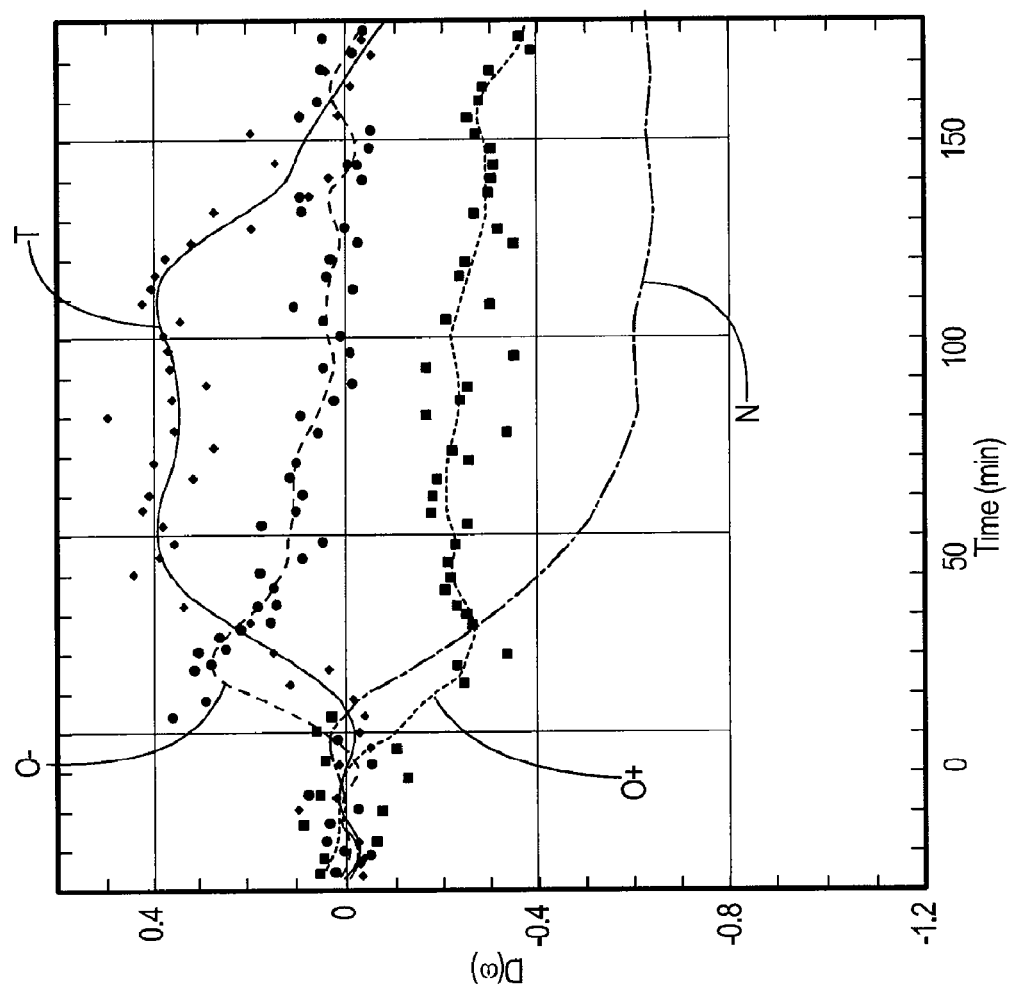
Figure 22F:
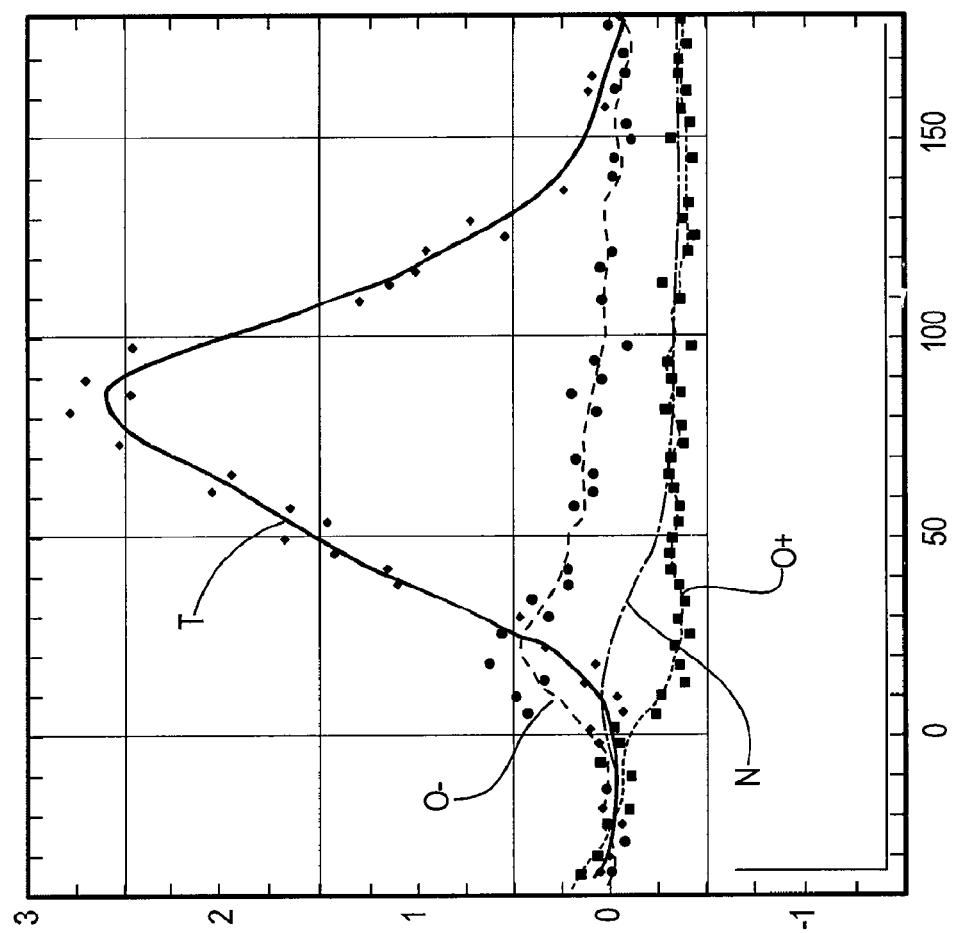

Osmolarity has a strong effect on the exchange of water into cells and tissue. Hypotonic conditions lead to strong cellular swelling, or edema, and possibly cell lysis, while hypertonic conditions desiccate the cells and cause them to contract. The change in the relative spectral density was monitored as the osmolarity of the growth medium around the tumors was changed. Isotonic conditions are 310 mOsm. The results of hypotonic conditions (200 mOsm) are shown in FIG. 22(b). The lower frequencies show weak suppression, while the upper frequencies show initial enhanced motion that slowly relaxes over 180 minutes. The hypertonic condition (400 mOsm) is shown in FIG. 22(c). The hypertonic effects on the spectrogram are opposite to the hypotonic, are stronger, and last longer. Cellular swelling increases the cell volume, decreases the density of intracellular constituents and facilitates intra-cytosol motion. This leads to increases in motion in the higher frequencies of FIG. 22(b). On the other hand, desiccation of the cytosol under hypertonic conditions shrinks the cell volume and increases the density of intracellular constituents, significantly impeding motion. However, membrane vesicles may still be active to reestablish stasis.

FIG. 21(d) shows the normalized spectral difference as a function of time and frequency for the changes caused by 1 μg/ml nocodazole. The tissue response to the anti-tubulin drug nocodazole shows very strong suppression in motion in the middle frequency range between 0.02 Hz to 1 Hz, but with enhancement at ultra-low frequency below 0.01 Hz. The strongest effect of nocodazole on intra-cellular motion is the reduction of microtubules in the cytosol that provide fewer pathways for organelle transport. Therefore, the strong suppression of frequencies in the range between 0.02 Hz to 1 Hz may be identified with intracellular organelle transport. This same frequency range showed enhanced motion at physiological temperatures relative to room temperature. Low cellular metabolism at room temperature would have slower organelle transport, again pointing to the frequency band between 0.1 Hz to 1 Hz as organelle-transport-related.

FIG. 21(e) shows the differential relative spectral change as a function of time at the frequency of 0.1 Hz for these four factors of thermal change (T), hypotonic change of osmolarity (O−), hypertonic change of osmolarity (O+), and nocodazole (N). FIG. 21(f) shows the differential relative spectral change as a function of time at the frequency of 1 Hz for these same four factors.

These differences in the tissue response reflect the specific actions of the perturbations on the tissue. Increasing temperature increases metabolic activity and increases membrane fluidity reflected in the preferential enhancement of frequencies around 1 Hz at physiological temperatures relative to room temperature. Conversely, osmotic hypotonicity induces tension on the cell membrane, increasing the effective undulation frequency while reducing damping, reflected in the enhanced fluctuations across the spectral range of FIG. 22(b), with opposite effects for hypertonicity in FIG. 22(c). In contrast, the anti-tubulin action of nocodazole decreases the number of microtubules in the cells and therefore specifically inhibits organelle motion, reflected in the strong suppression of the mid-frequency fluctuations. These spectral cues allow a tentative identification of the lowest frequencies (below 0.1 Hz) as part of the 1/f spectrum of slow membrane shape changes; mid frequencies as part of undulations (between 0.1 and 1 Hz), while the higher frequencies (1 Hz and above) originate with organelle motion.

The above preliminary discusses applying speckle fluctuation spectroscopy to dynamic speckle obtained using coherence-gated digital holography on living tumor spheroids. By defining a relative spectral response to perturbations, spectrograms of the tissue were generated responding to temperature changes, osmolarity changes and to the anti-tubulin drug nocodazole. Different spectral ranges increase or decrease, depending on the perturbation, providing insight into the different cellular functions that contribute to different spectral ranges. The striking changes in the responses to various perturbations provide a means to develop spectrogram fingerprints that can be used to identify the effects of drugs on cellular activity. Therefore, the spectrograms define the specificity of motility-contrast imaging to different perturbations and to different functional responses. These signatures and their specificity may open the door to broad compound screening applications. More specific discussion of the method(s) of such compound screening applications follows immediately below.

Drug Screening Using Fluctuation Spectroscopy of Living Tissue

The application of low-coherence digital holography to measure the fluctuation spectra of dynamic speckle arising from cellular and subcellular motions in living tissue is now further discussed. The resulting fluctuation spectrograms act as fingerprints for specific drug action and toxicity. The speckle is sectioned from a fixed depth as deep as 1 mm inside tissue using short-coherence light and coherence gating through digital holography. The cells inside tissue are in their natural environment and far from surfaces allowing them to have a natural response to perturbations. The differential spectrograms capture the response as a function of time as drugs affect the internal functions of the cellular processes. Different perturbations produce time-frequency differential spectrograms that act as specific fingerprints for the mechanism of action. By creating a library of drug response spectrograms for known drugs, the spectrograms from unknown drug candidates can be matched to known drugs through fingerprint similarity analysis. In addition to elucidating mechanisms of action, the state of health of the tissue can be monitored for general toxicity to drug candidates, providing an approach to early toxicity testing in drug discovery.

Motion as a Functional Endogenous Imaging Contrast

Living tissue prominently displays two types of dynamic processes: metabolism and motion. Both of these processes are intimately connected to biological function. Significant effort in molecular imaging has focused on metabolism as the origin of cellular function, including nucleotide and protein metabolism. However, the ultimate measure of cellular function is cellular dynamics: how the internal constituents of cells move. Almost no attention has been paid to cellular motility as a form of functional imaging of tissue. Dynamic light scattering in living tissue has been used for blood flow monitoring, and for trauma assessment, but direct functional imaging of subcellular motion has been developed only recently by the work of Nolte et al. through motility contrast imaging (MCI).

Motility contrast imaging uses short-coherence holography to detect subcellular motion of membranes and organelles inside of cells inside of tissue. The primary data acquired after shining partially coherent light on tissue are fully-developed speckle fields. This is in sharp contrast to OCT (Optical Coherence Tomography) that seeks to eliminate speckle to achieve the highest possible spatial resolution. The speckle-fields of MCI arise from the interference of multiple scatterers with random phases within a coherence volume inside the tissue. The holographic coherence gate localizes the detected motion to within a thin slab inside the tissue with a thickness determined by the coherence length of the laser. Using this approach, permits nanoscale motion to be sensed as deep as 1 mm inside tissue localized to within 30 micron volumes (voxel size corresponding to our spatial resolution) across a field of view of 1 mm. MCI presents us with an unexpected imaging approach based on motility as the contrast agent. The dynamic behavior of the tissue is captured in so-called motility metrics that represent the degree of fluctuations of dynamic speckle, either through speckle decorrelation times or through normalized standard deviations. The motility contrast shows clear differentiation of metabolically active proliferating tissue relative to necrotic tissue in multicellular tumor spheroids. However, considerably more information is present that can be extracted by studying the fluctuating signal and its characteristic fluctuation frequencies.

Useful data results from an analysis of the fluctuation spectra of coherence-gated dynamic speckle. The differential response of the fluctuation spectrum shows specific responses to changes in temperature and osmolarity, as well as differentiated responses to metabolic drugs that separately affect oxydative phosphorylation or anaerobic glycolysis, and to cytoskeletal anti-mitotic drugs separately affecting microtubules or actin filaments. In particular, the spectral response to cytochalasin exhibits simultaneous positive and negative responses in separate spectral bands that explain the weak motility metric response observed previously. This new fluctuation spectroscopy has utility for high-content screening (HCS) and high throughput screening (HTS).

High content screening (HCS) is an imaging approach to cell-based assays for in vitro toxicology screening and the transition of test targets from biochemical to cell-based assays. The measured properties of a target compound include its cellular availability, potency, specificity and toxicity. The power of high-content screening has been derived from molecular labeling of proteomic and genomic pathways combined with the high spatial resolution of microscopy to image organelles and cell morphology changes. Molecular labeling requires the introduction of exogenous agents into the cells, which may be problematic for high molecular weight moieties and for non-membrane-permeable drugs that would then also require tissue fixing and membrane proration for labeling. The measured endpoints for HCS tend to be molecular (gene expression or translation) rather than functional behaviors that include cell size changes, organelle activity, endo and exocytosis, cytoskeletal integrity, membrane stiffness, cytosol elasto-viscous properties, etc., that can be probed by motility contrast imaging in full 3D environments.

The chief advantage of HCS (high spatial resolution) is also its chief weakness. To scan many cells across many samples is time-consuming and generates very large datasets that need to be captured and stored digitally, causing data-storage challenges as well as time-consuming data processing. The small field of view furthermore requires high-precision automation of the sample bed and of the optical train. The tolerance on optical performance for image-based acquisition must be tight with autofocus capabilities. In contrast, motility contrast imaging has very broad tolerance to defocus because speckle fields (which contain the statistical information upon which we base image contrast) are immune to even relatively severe defocus. A more serious limitation of microscopy-based HCS is the limited tissue penetration up to only 100 microns using confocal microscopes, as opposed to motility contrast imaging that can penetrate as deep as 1 mm into living tissue using coherence-gated holography, probing cells far from surface gradients that can affect cell phenotypes.

There are challenges associated with using labels when compared with label-free MCI. The chief limitation that restricts high-content screening to small numbers of only 8 to 10 physiological measurements per day per sample is the need for exogenous labels. Labels present many difficulties that adversely affect speed of screening and multiplicity of physiological endpoints. In tissue-based screens, the perfusion of the exogenous label suffers transport limitations, possibly with low diffusion coefficients for large molecular weights. In addition, many labels may be non-membrane permeable, such as large molecular weight molecules, nanostructures or quantum dots. These require the tissue to be fixed and the membranes perforated to introduce them into the cells, seriously altering cell morphology and preventing any longitudinal time-response studies. A much broader adverse effect is the cytotoxicity of many of the fluorophores and chromophores used as labels, again preventing time-course measurements that need to isolate the effect of the target compound uncontaminated by the cellular response to the label. Once the exogenous label is in place, the labels may bleach or may blink, making it difficult to quantify concentrations. Ultimately, it is the difficulty of introducing multiple labels simultaneously that do not interact that seriously limits the multiplexing ability of high-content screening A further limitation to only a dozen physiological measurements per day is because of cross-reactivity or nonspecific binding. In label-free detection, provided by motility contrast imaging, many of these road-blocks are removed.

High-content screening is based on the long-standing industry standard of the two-dimensional cell culture. However, the validity of two-dimensional cultures for cytotoxicity screening is being seriously questioned, with a major move to develop more three-dimensional environments for the cells. Two dimensional cell cultures fail because the cells have the wrong morphology relative to their natural state in a three-dimensional topology that includes extracellular matrix and three-dimensional cell-cell contacts. The intracellular and inter-cellular signaling pathways are altered by the altered morphology and local topology. Such cells responding to a drug candidate exhibit an altered response that may not be indicative of the natural physiological state, leading to false leads as well as missed candidates.

What is needed is a tissue-based screen that is three-dimensional. Cells deep within tissue may not be accessible to standard probes, such as confocal microscopy or two-photon microscopy, but they are accessible using MCI. This disclosure describes three-dimensional motility assays using MCI applied to three-dimensional tissues that retain the relevant molecular signaling of in vivo tissue but with the advantages of working in vitro.

To test target compounds, we use multicellular tumor spheroids within which the tumor cells have a full three-dimensional environment, which is becoming recognized as an important factor in intercellular signaling. Multicellular spheroids of normal cells or neoplastic cells (tumor spheroids) are balls of cells that may be easily cultured up to 1 mm in size in vitro. The spheroids can be used to simulate the optical properties of a variety of tissues such as the epidermis and various epithelial tissues, and may be used to simulate the histological and metabolic features of small nodular tumors in the early avascular stages of growth. Three-dimensional aggregates of permanent cell lines offer a reliable model for systematic study of tumor response to therapy. In vitro monitoring of tissue response to drugs is an area of strong interest to pharmaceutical companies. Although the in vitro environment is artificial, the biochemistry, metabolism and cell signaling response of cells grown as 3D constructs closely simulates in vivo tissue. Therefore, in vitro experiments are a validated (and inexpensive) surrogate for in vivo response.

Beyond a critical size (about 100 microns) most spheroids develop a necrotic core surrounded by a shell of viable, proliferating cells, with a thickness varying from 100 to 300 mm. The development of necrosis has been linked to deficiencies in the metabolites related to energy generation and transfer. The limiting factor for necrosis development is oxygen—the oxygen consumption and oxygen transport reflecting the status of the spheroid. Early work on spheroids launched the study of therapeutic strategies for cancer, especially the spheroid response to different drugs. The response to drug therapy was quantified from an analysis of spheroid volume growth delay, increase in the necrotic area, and change in survival capacity, but these are all gross and indirect measures. This work focused on hypoxia and its induction by chemical agents. None of these studies considered cellular and sub-cellular motility as a diagnostic of cellular vitality, despite the obvious utility of this diagnostic, because there was no means of detecting motility nondestructively throughout a volume. Motility contrast imaging provides this capability for the first time, and we obtain motility information up to a millimeter deep in tumor spheroids.

Optical Coherence Imaging and Motility Contrast

Optical coherence imaging uses coherence-gated holography to optically section tissue up to 1 mm deep. It is a full-frame imaging approach, closely related to en face optical coherence tomography, with high-contrast speckle because of the simultaneous illumination of a broad area. The basic system is shown in FIG. 20. A mode-locked Ti:sapphire laser (100 fs pulse duration, 100 MHz repetition rate) is used with a center wavelength of 840 nm and a bandwidth of 17 nm. The lenses L1 and L2 expanded a reference beam, and the lens L3 performed the Fourier transform of the object beam. The CCD camera was placed at the Fourier plane of the object, where the object beam interfered with the zero-path-matched reference beam that passed through the computer-controlled delay line. The typical object intensity for living tissue at the object plane was 5 mW/mm$^2$, and an 8-bit CCD camera with one mega-pixel resolution was used with an exposure time of 10 msec. Digital holograms were reconstructed by Fast Fourier transform (FFT).

In the embodiment of FIG. 20, MCI is based on off-axis digital holography using a CCD camera with a 7.4 micron pixel pitch. The nominal speckle size on the CCD chip is approximately 6 pixels with approximately 3 optical fringes per speckle using a reference beam crossing angle of 3 degrees at a wavelength of 840 nm.

The biological targets might preferably be multicellular tumor spheroids. These are avascular tumors grown in a circulating bioreactor from proliferating cell lines. They grow to a diameter up to 1 mm. Multicellular tumor spheroids have approximately spherical geometry that facilitates comparison of structure to function. As tumor spheroids are cultured in a rotating bioreactor, they undergo cell apoptosis or necrosis in their center and so consist of an inner necrotic core surrounded by an outer proliferating shell with a 100- to 200-mm thickness. The scattering anisotropy factor for tumors up to 500 microns thick is approximately g=0.9 with a reduced extinction coefficient of m'=10 mm$^{-1}$ at a wavelength of 840 nm.

In living tissue, the speckle is dynamic, caused by motion of cellular membranes and by intracellular organelles, coupled with the optical channel cross-talk caused by multiple scattering. The membrane and organelle motions are intimately connected to and directed by the cytoskeleton, and hence cytoskeletal drugs have pronounced effects on the dynamic speckle. We previously studied the effects of antimitotic drugs on tumor spheroids using optical coherence imaging, and defined motility metrics from the autocorrelation functions of the depth-gated pixel fluctuations. The resulting motility contrast imaging (MCI) is fully endogenous, responding to the dynamic functions of cellular processes. The autocorrelation function is a first-order heterodyne function because the holography uses a reference wave (the coherence gate) that captures the real and imaginary part of the fluctuating field as the coherence-gated pixel number $i^{(1)}_d(t)$ to yield the autocorrelation function $$A^{(1)}(\tau) = \langle i_d^{(1)}(0) i^{(1)}_d(\tau) \rangle \propto I_{LO}^2 + 2I_{LO} Re\{I^{(1)}(\tau)\}$$

where $\tau$ is the time delay among an ensemble of images, and $I^{(1)}(\tau)$ is the heterodyne correlation function. Two motility metrics can be defined from the heterodyne correlation function. They are the decay time, and the normalized standard deviation, given by $$NSD = \left( \frac{2Re\{I^{(1)}(\tau_{max}) - I^{(1)}(0)\}}{I_{LO}} \right)^{1/2}$$

Figure 23:
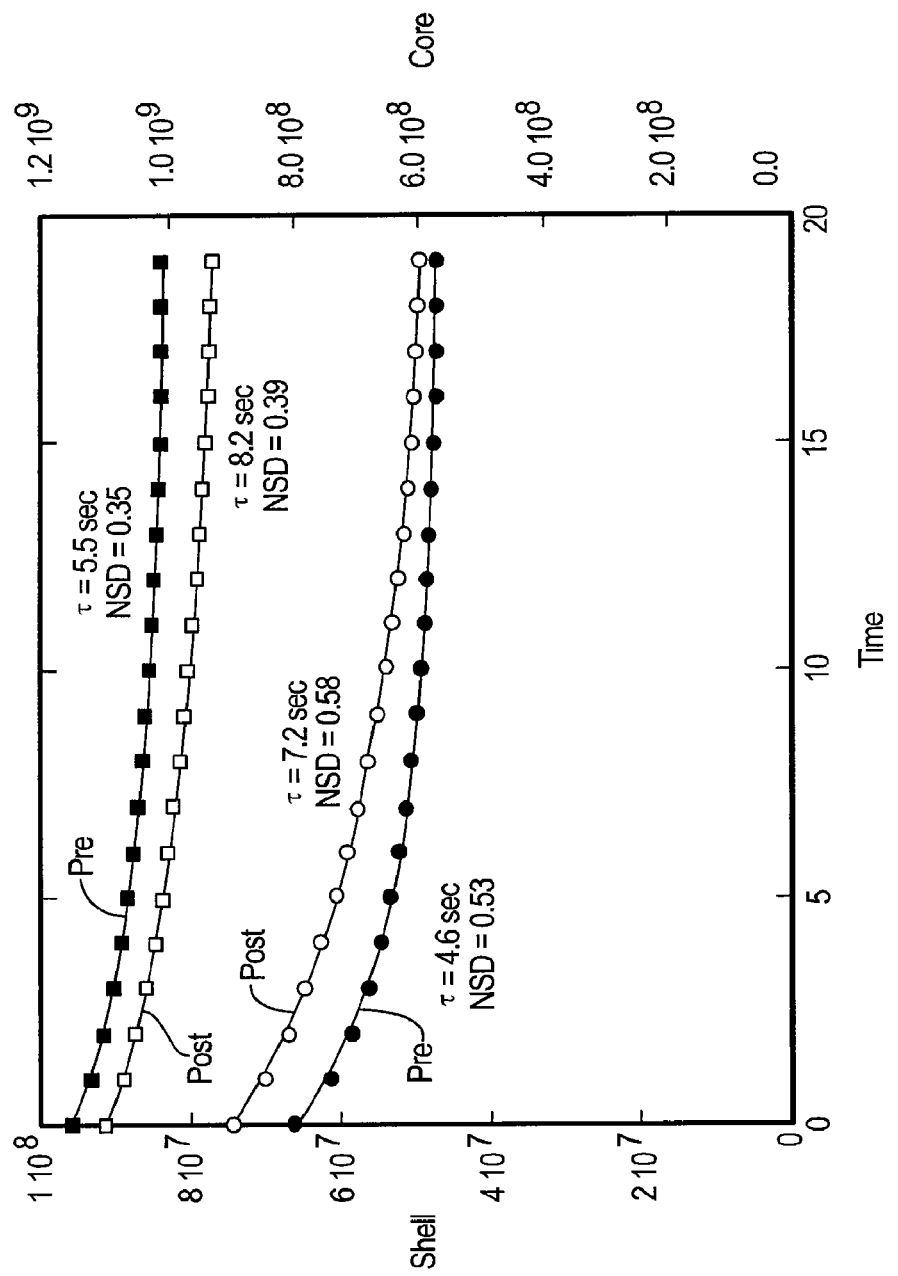
FIG. 23 shows the heterodyne autocorrelation function for the proliferating shell and the necrotic core before (pre) and 10 minutes after (post) a dose of 10 μg/mL of cytochalasin D was applied to the tumor, where the correlation time and NSD metric values are shown for each.

The heterodyne autocorrelation function from a fresh tumor spheroid is shown in FIG. 23. An ensemble consists of 40 images taken with a frame rate of 1 per second. The figure shows the autocorrelation function for the healthy shell and for the necrotic core before a dose of 10 μg/ml of cytochalasin D was applied, and 10 minutes after the dose was applied. The healthy shell becomes 6% brighter after the dose, the correlation time increases from 4.6 sec to 7.2 sec, and the NSD has a slight increase from 0.53 to 0.58. The necrotic core shows similar trends in the correlation time and NSD changes, but with significantly smaller NSD values, and the core becomes dimmer after the dose, possibly because the effective extinction of the shell had increased.

Fluctuation Spectroscopy and Response to Environmental Perturbation

Autocorrelation functions and power spectra are related through a Fourier transform $$I_1(\omega) = \frac{1}{2\pi} \int_{-\infty}^{\infty} e^{-i\omega\tau} Re\{I_1(\tau)\} dt \propto \left| \frac{1}{2\pi} \int_{-\infty}^{\infty} e^{-i\omega t} i_d^1(t) dt \right|^2$$

Although the autocorrelation function and the power spectrum contain identical information, the interpretation of that information is qualitatively different. In particular, the spectral information directly displays the presence of characteristic frequencies that can be related to biophysical processes, such as fluctuating membranes or organelle transport.

This disclosure makes extensions that improve the sensitivity and specificity of MCI while shifting the emphasis of the measurement to functional biomarkers that are monitored in real-time. One extension is the analysis of the dynamic speckle in terms of fluctuation spectral bands and drug-response fluctuation spectrograms that replace the motility metric that our prior work has employed as the source of endogenous imaging contrast. By capturing the differential fluctuation spectrograms of living tissue responding to drugs, much more information is captured. Differential spectrograms become analogous to unique fingerprints that will be much more specific to mechanism of action at a functional level of the effects on intracellular motion.

The spectral density from n distinct processes in the cell is given by $$S(\omega) = \frac{1}{\pi} \sum_n \frac{A_n}{1 + (\omega/\omega_n)^2}$$

$$\omega_n = \begin{cases} q^2 D & \text{Diffusive Transport} \\ qv & \text{Active Transport} \end{cases}$$

where the magnitude $A_n$ is determined by the number density of the population of scatterers that contribute to the n-th process, and $w_a$ is a characteristic frequency from diffusive or active transport. The scattering wavenumber q=4p/1 in the backscattering geometry, D is the effective diffusion coefficient and v is the transport velocity. Membrane undulations have a diffusive character with small values of D that give $w_n$ in the range 0.1-1 Hz, while organelle transport is active transport with velocities in the range of 0.1 to 1 micron/second with $w_n$ in the range 20 to 100 Hz. At ultra-low frequencies below 0.1 Hz the motions are likely on the scale of the cell size and would include gross changes in cell shape or movement of the cell, which are motions that could be related to necrosis and apoptosis and the formation of membrane blebs.

The drug-response spectrograms are defined by the differential relative spectral density as $$D(\omega,t)=[S(\omega,t)-S(\omega,t_0)]/S(\omega,t_0)$$

where the spectrum at time t is related to and normalized by the spectrum at time $t_0$ before the application of the perturbation or dose. The normalization is essential, because the spectral power density has general 1/f behavior, and the high frequency amplitudes are much smaller than the low frequency amplitudes. The differential spectrogram is sensitive to shifts in the magnitudes $A_n$ (dependent on the number of moving constituents) and in the characteristic frequencies $w_n$ (the speed of the moving constituents).

Figure 24:
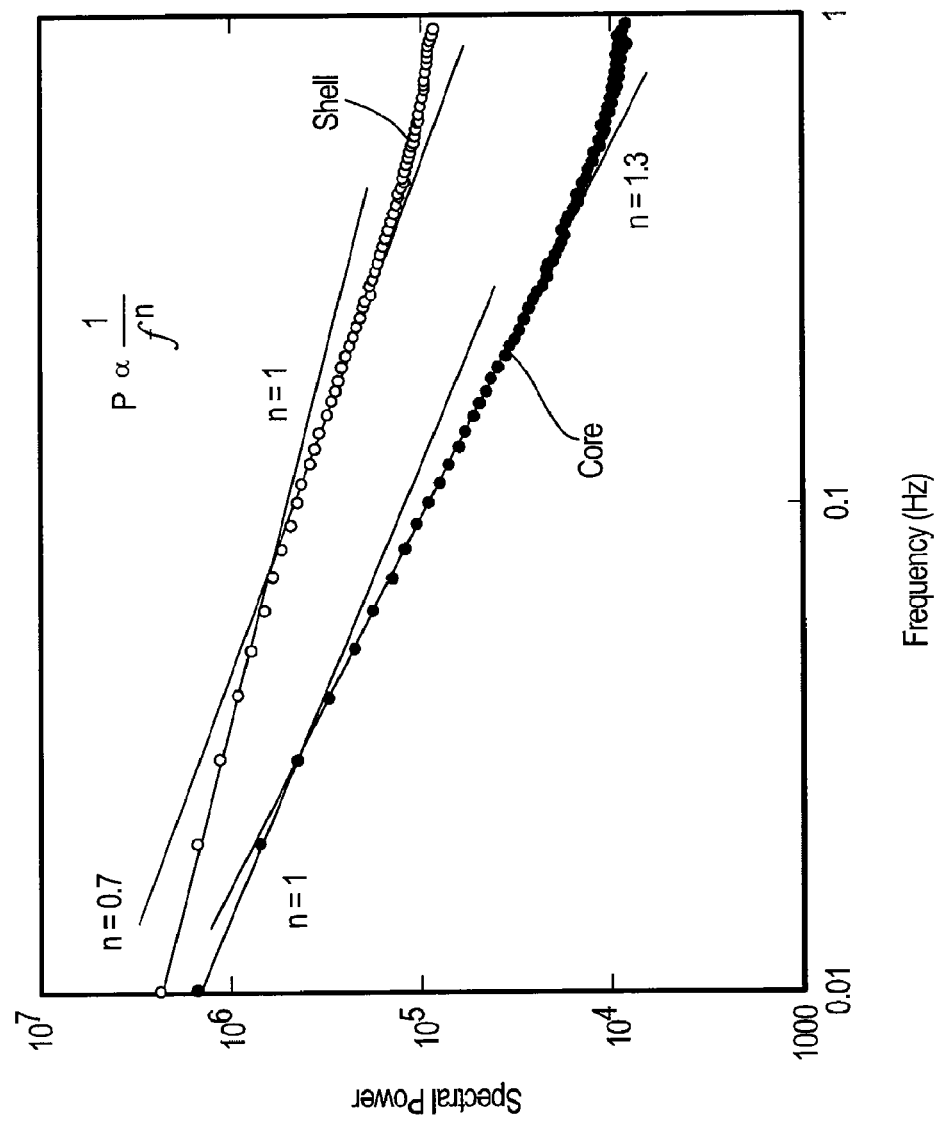
FIG. 24 shows the spectral power density for the proliferating shell and the necrotic core of a tumor spheroid showing the shell is significantly more active than the core, where the power spectra show $1/f^p$ behavior with slight breaks in slope around 0.1 Hz and around 0.5 Hz.
Figure 25A:
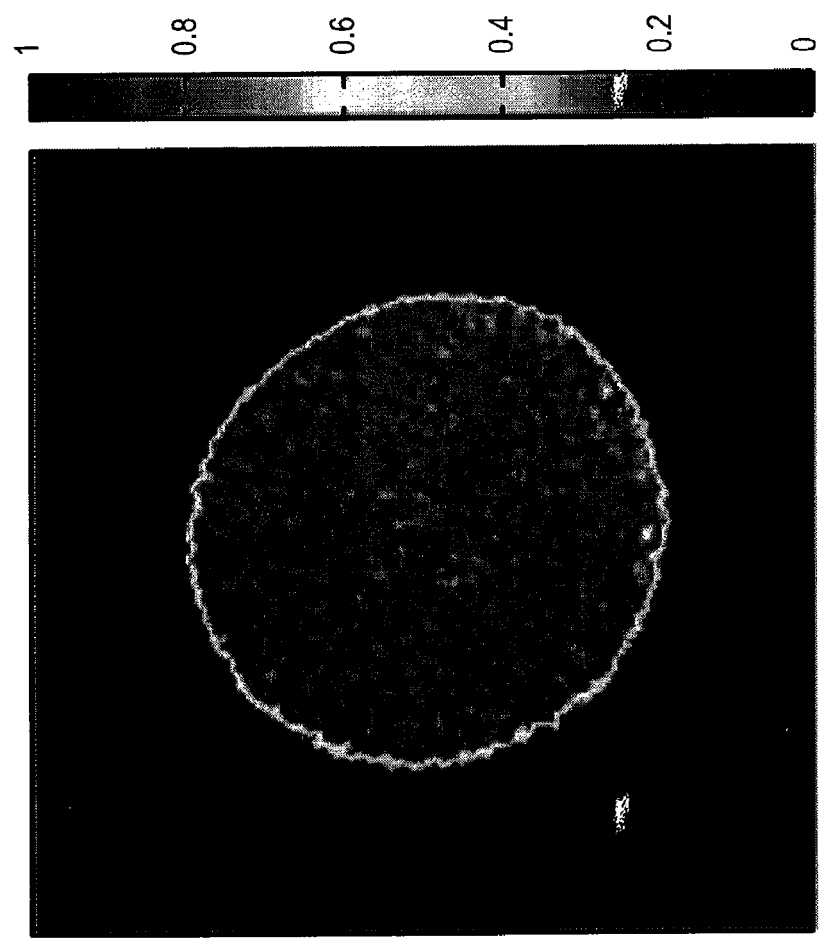
FIG. 25 shows differential spectrogram of a negative control experiment of tumor responding only to normal growth medium where the NSD density and the spectrograms are both flat over 6 hours.
Figure 25B:
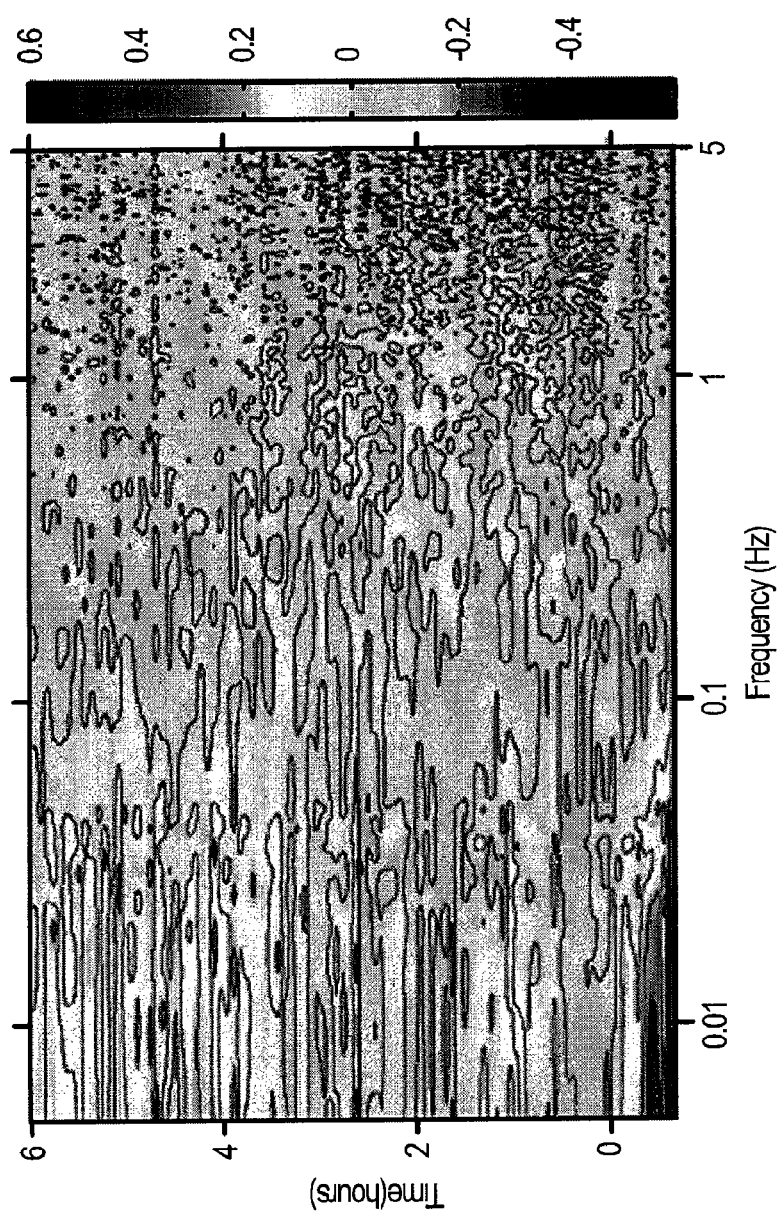
Figure 25C:
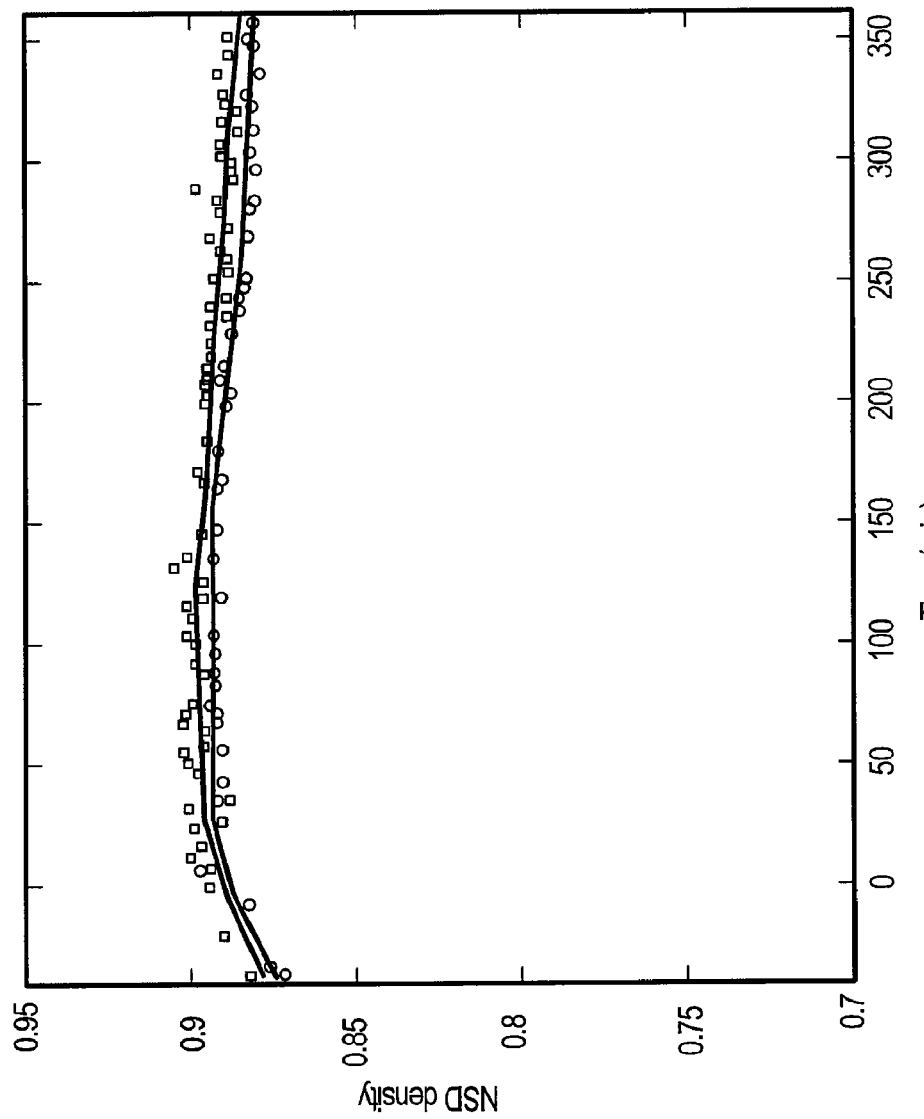
Figure 25D:
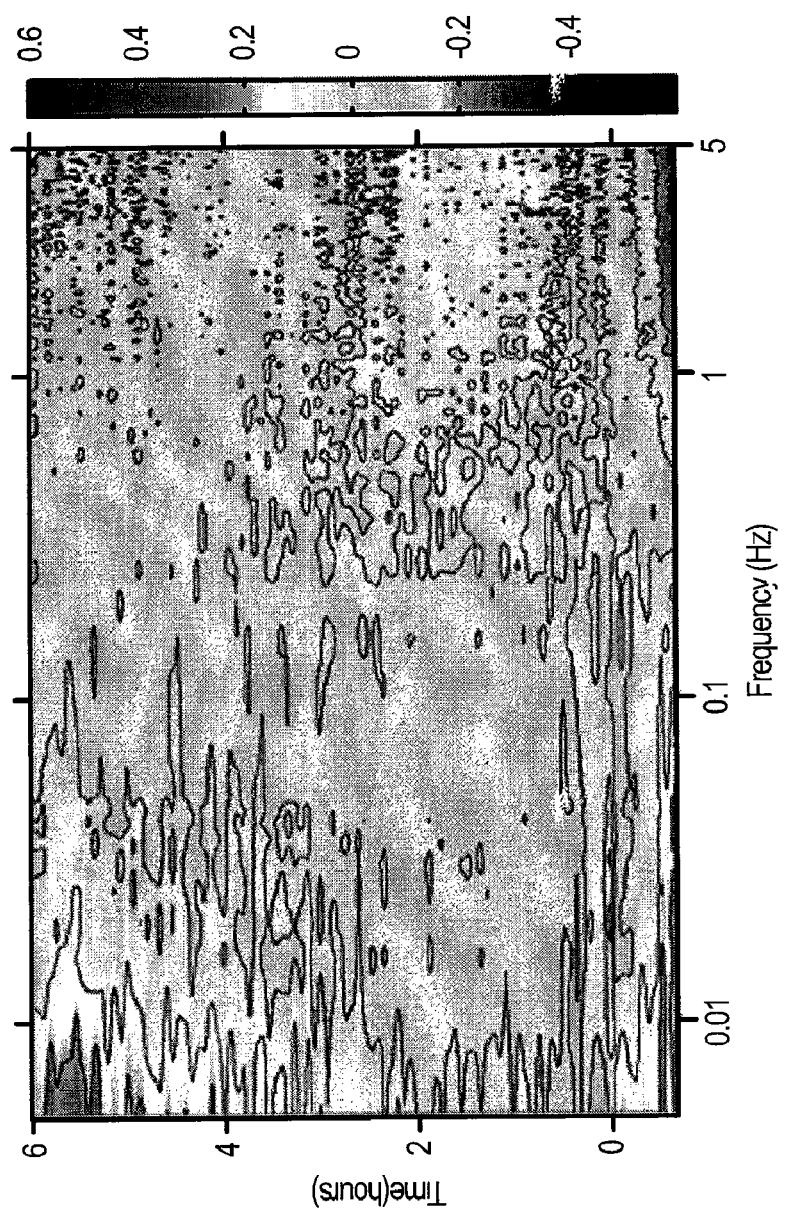
Figure 27A:
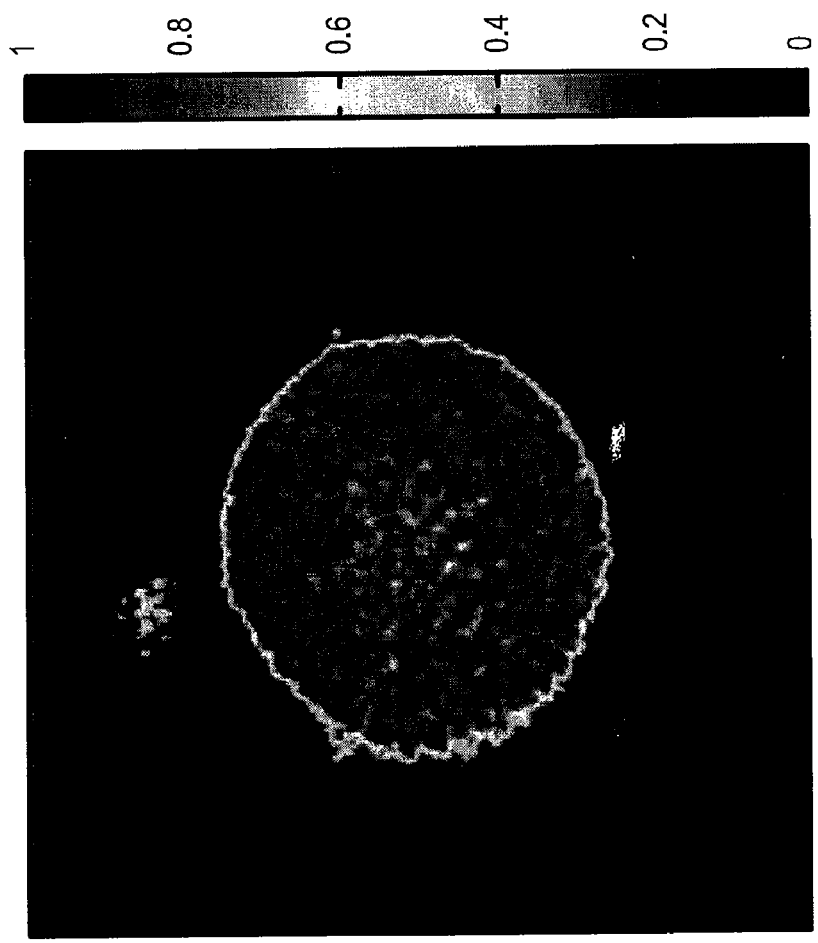
FIG. 27 shows a motility contrast image of a 400 micron diameter tumor, the motility metric for the shell as a function of time for an increase in temperature from 24° C. to 37° C. and then to 43° C., the motility metric for the core as a function of time for the same temperature variations, and the differential spectral power densities for the shell and core.
Figure 27B:
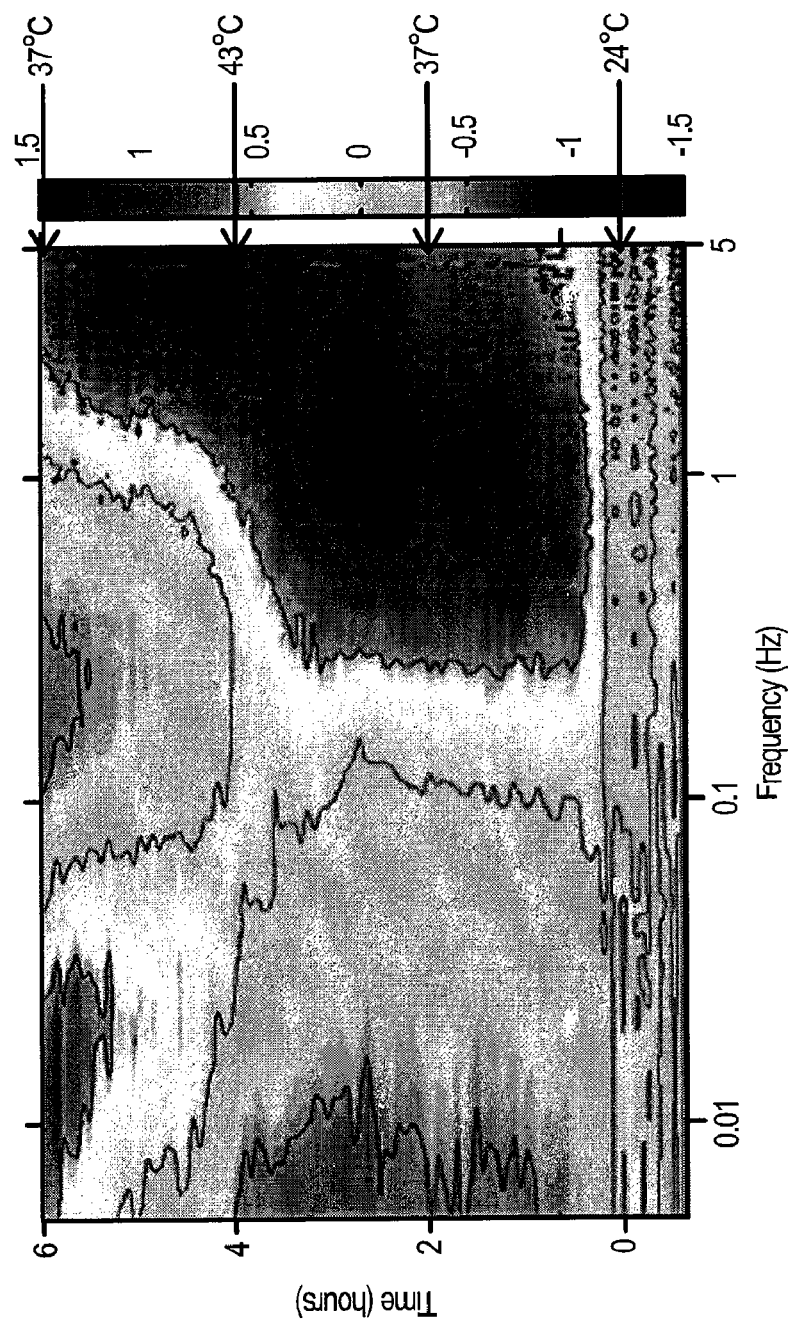
Figure 27C:
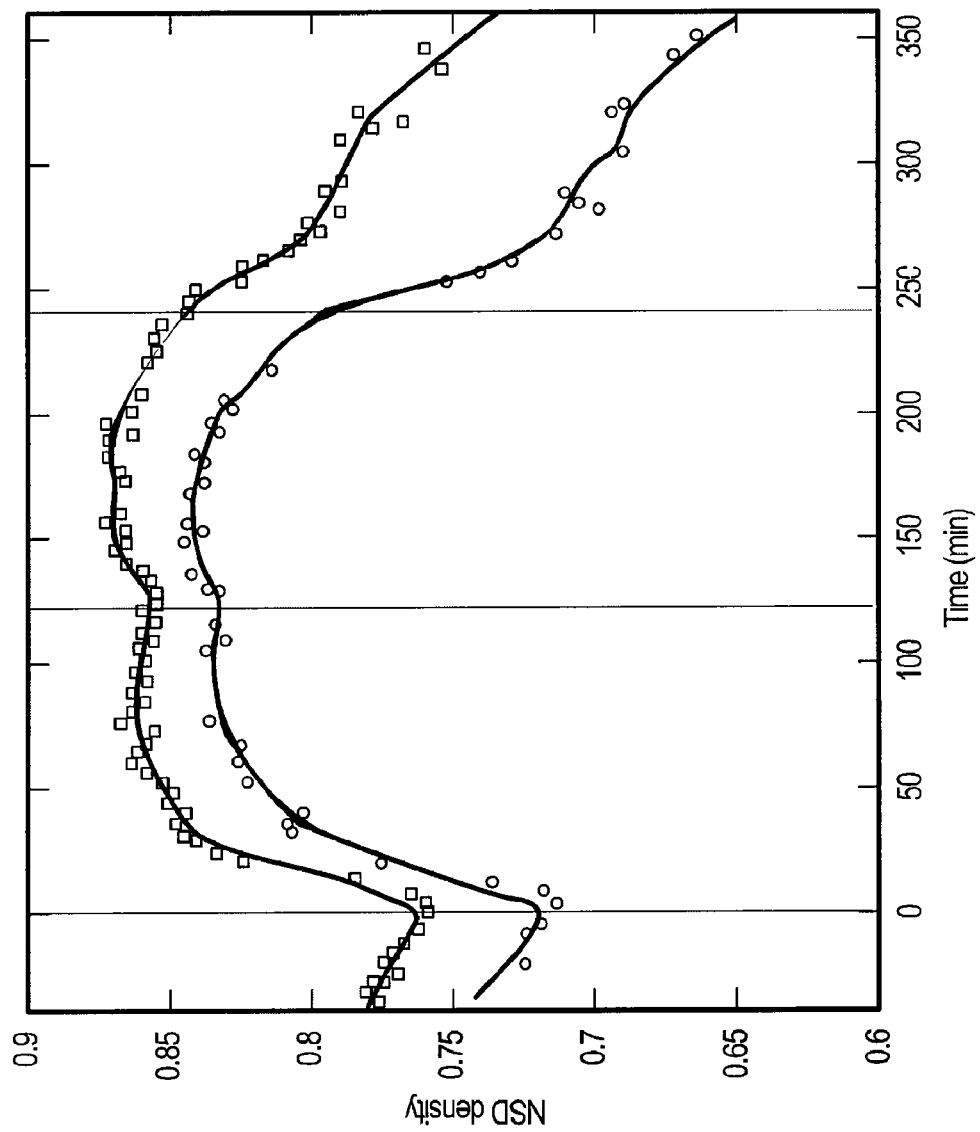
Figure 27D:
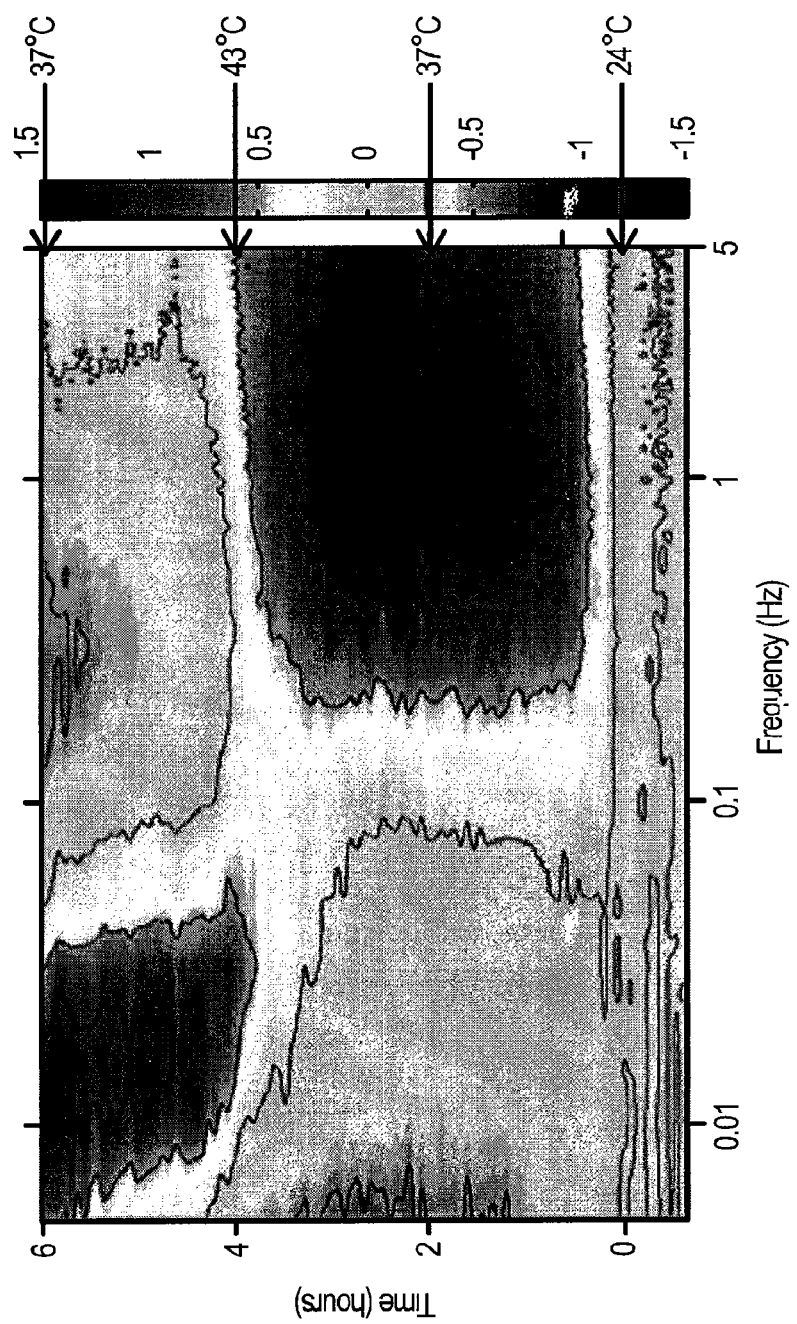
Figure 28A:
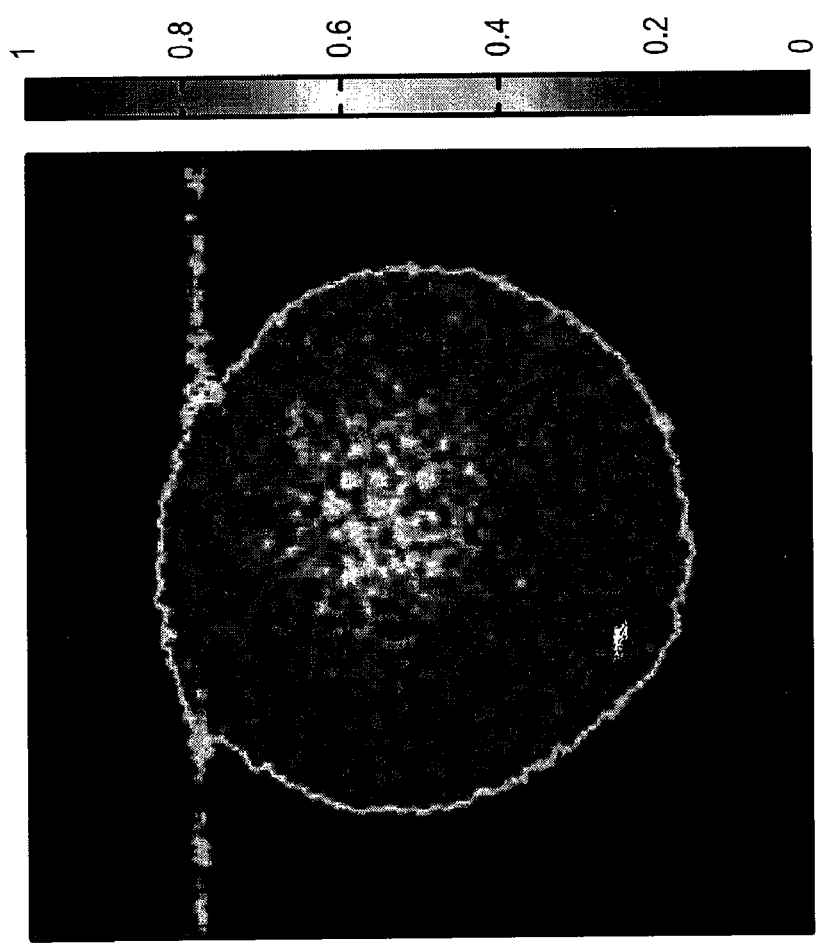
FIG. 28 shows a spectrogram of a tumor beginning at physiological temperature of 37° C. and heated to 43° C. for only 10 minutes before returning to physiological temperature, where the thermal increase is most apparent in the shell in the high frequency band, and returns to normal after the temperature is decreased.
Figure 28B:
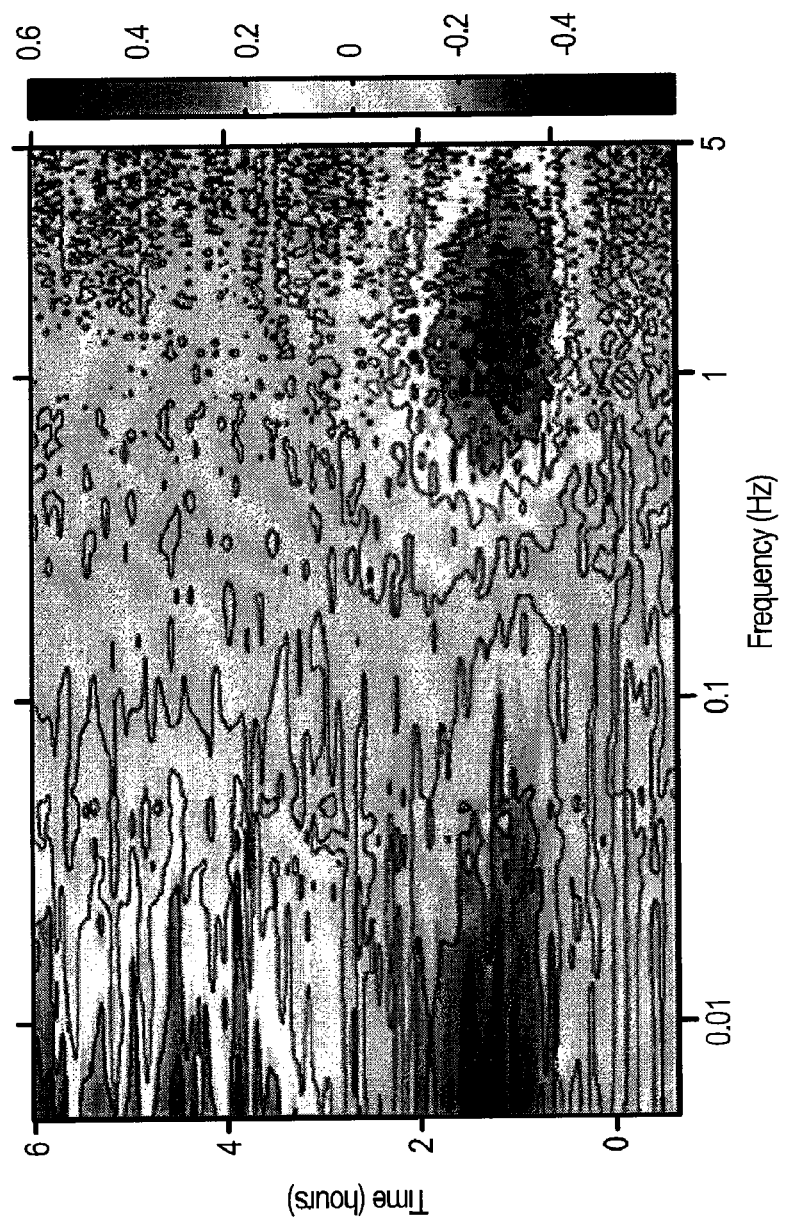
Figure 28C:
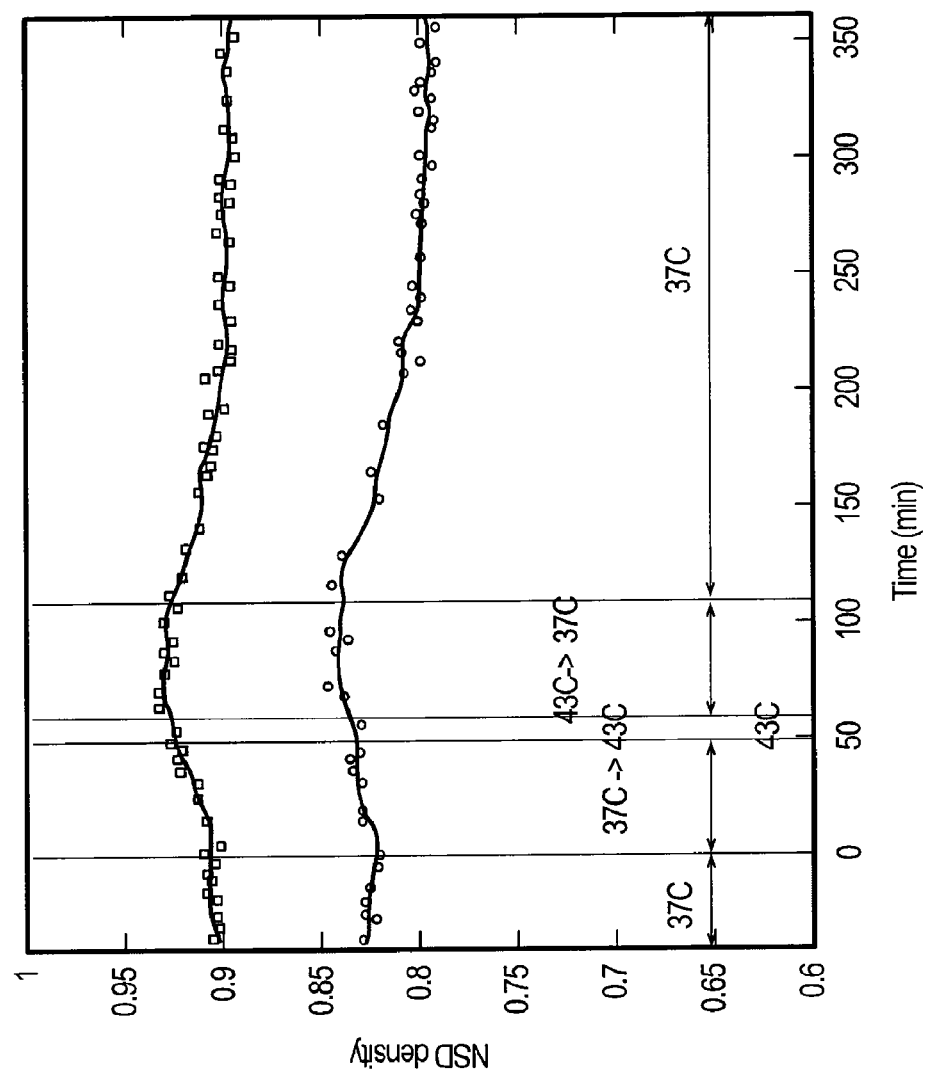
Figure 28D:
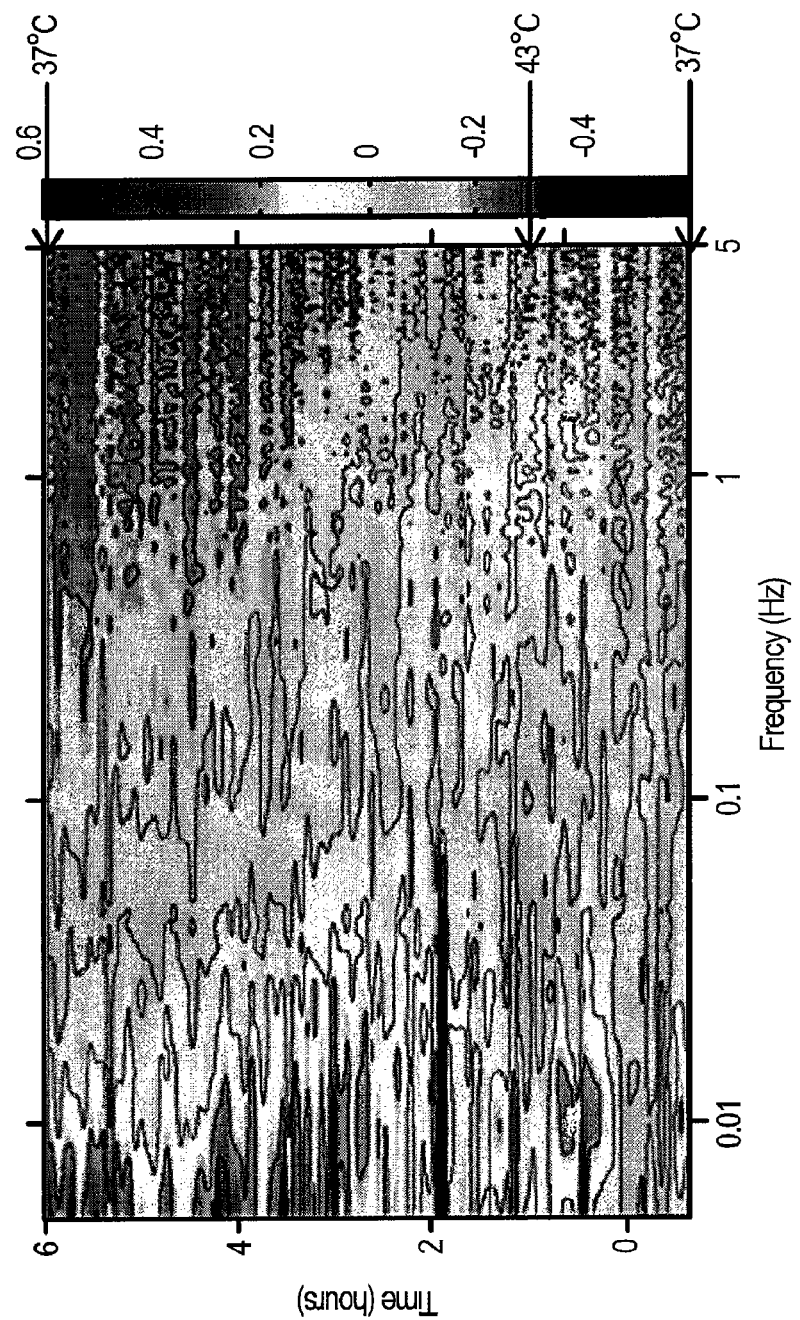
Figure 29A:
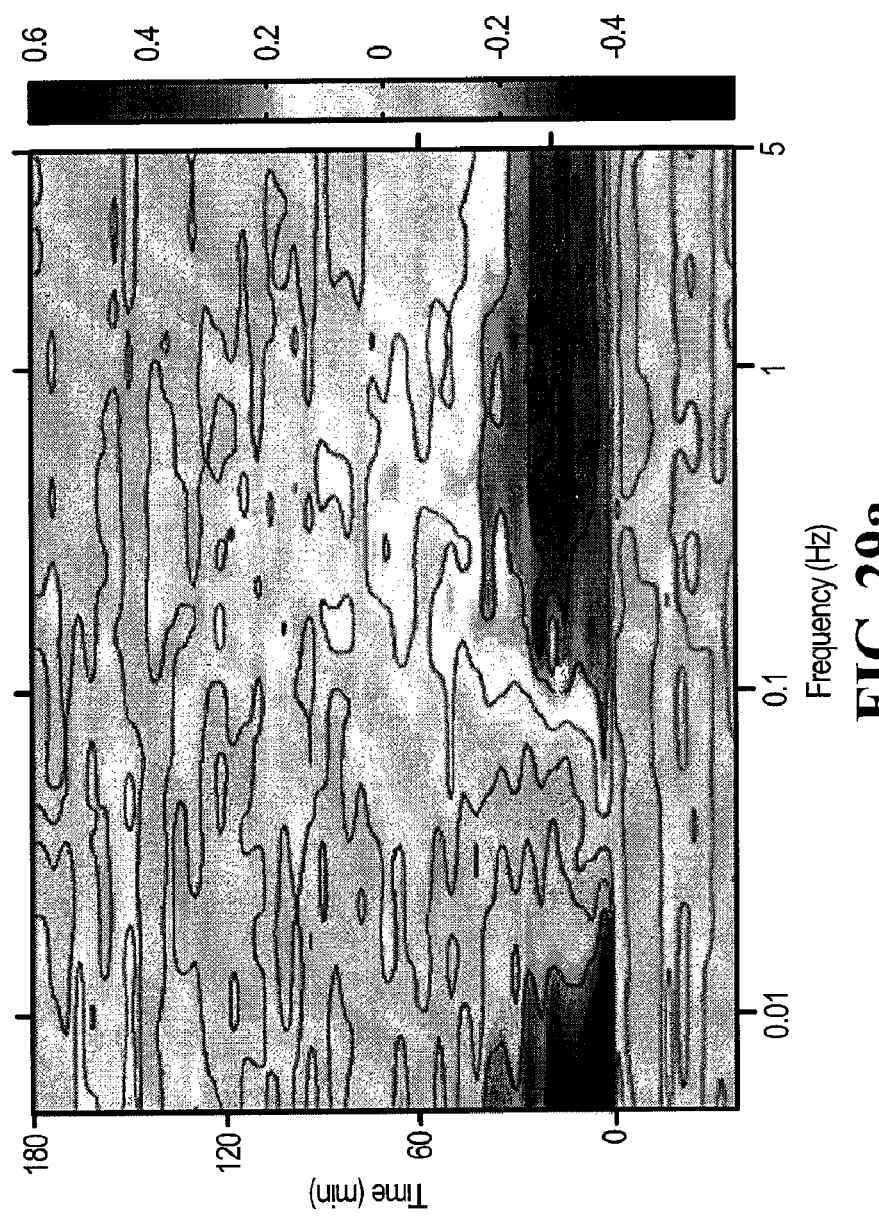
FIG. 29 shows the response of the relative spectral power to changes in osmolarity at 25° C. as the osmolarity is changed from isotonic (300 Osm) at 0 minutes, where the hypotonic osmolarity of 200 mOsm induces swelling of the tumors and the hypertonic solutions of 400 mOsm causes tumor desiccation and shrinkage.
Figure 29B:
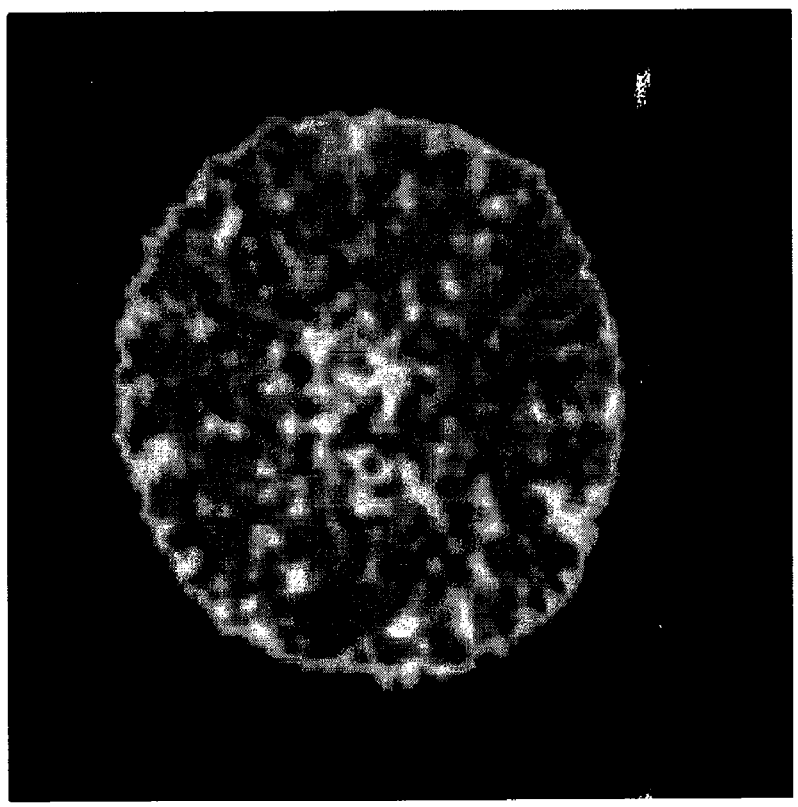
Figure 29C:
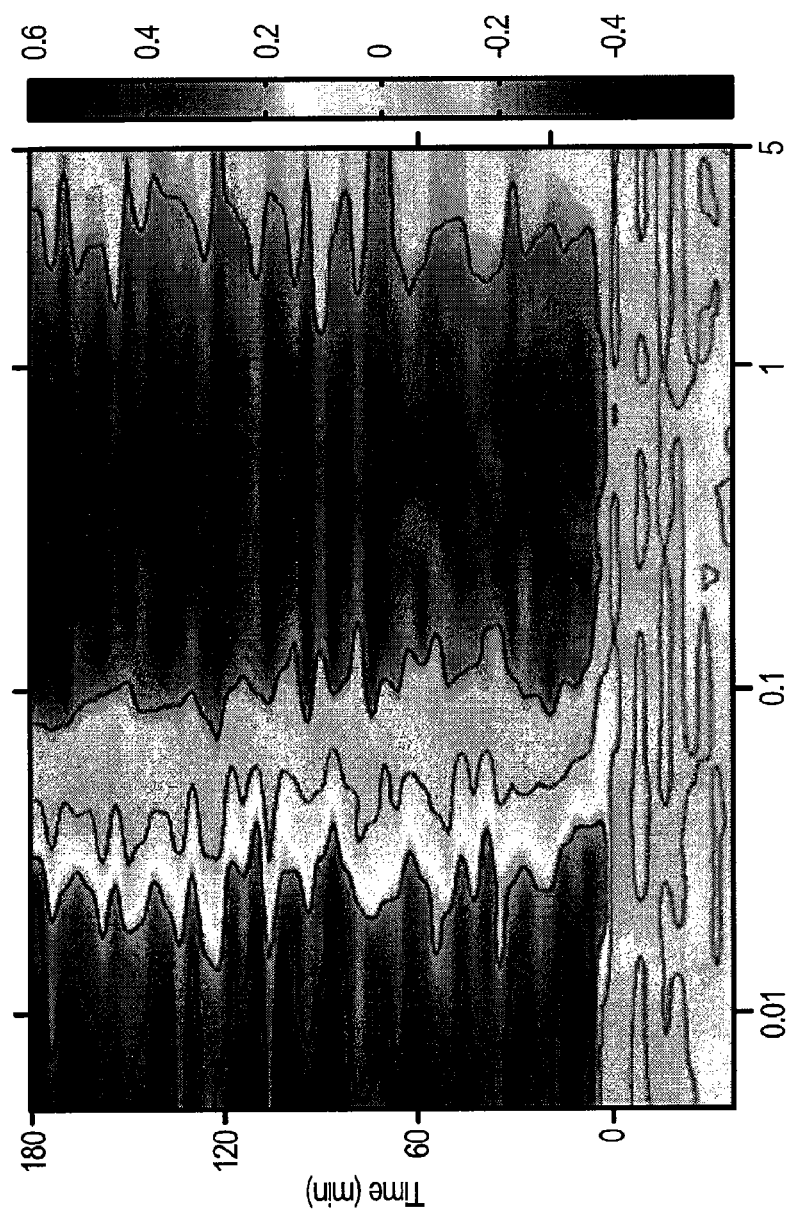
Figure 29D:
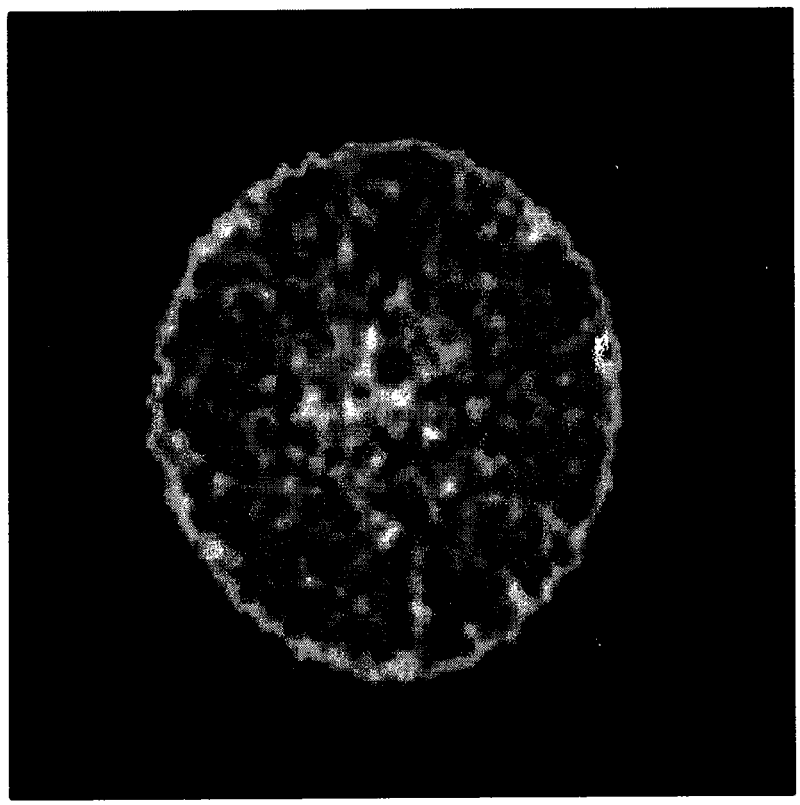
Figure 30A:
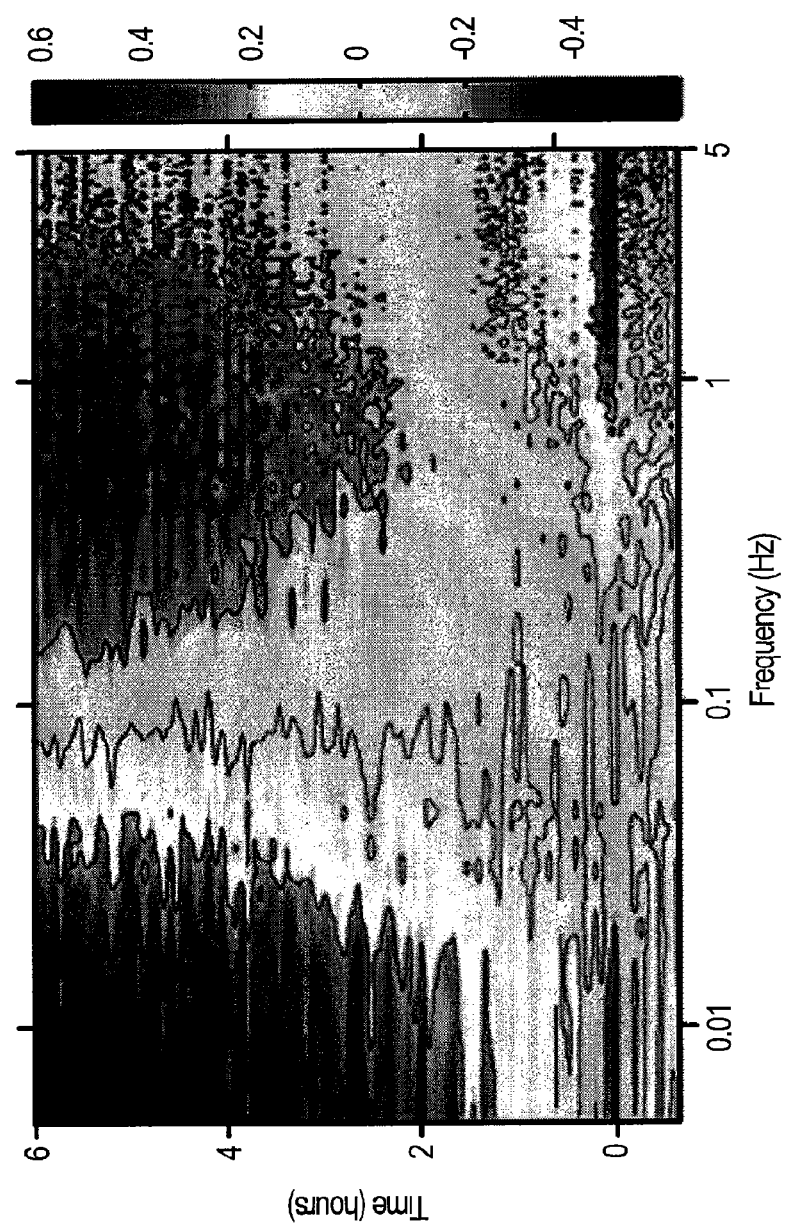
FIG. 30 shows the response of the relative spectral power to changes in osmolarity at physiological temperature 37° C., where the hypotonic osmolarity is 150 mOsm, and the hypertonic osmolarity is 500 mOsm.
Figure 30B:
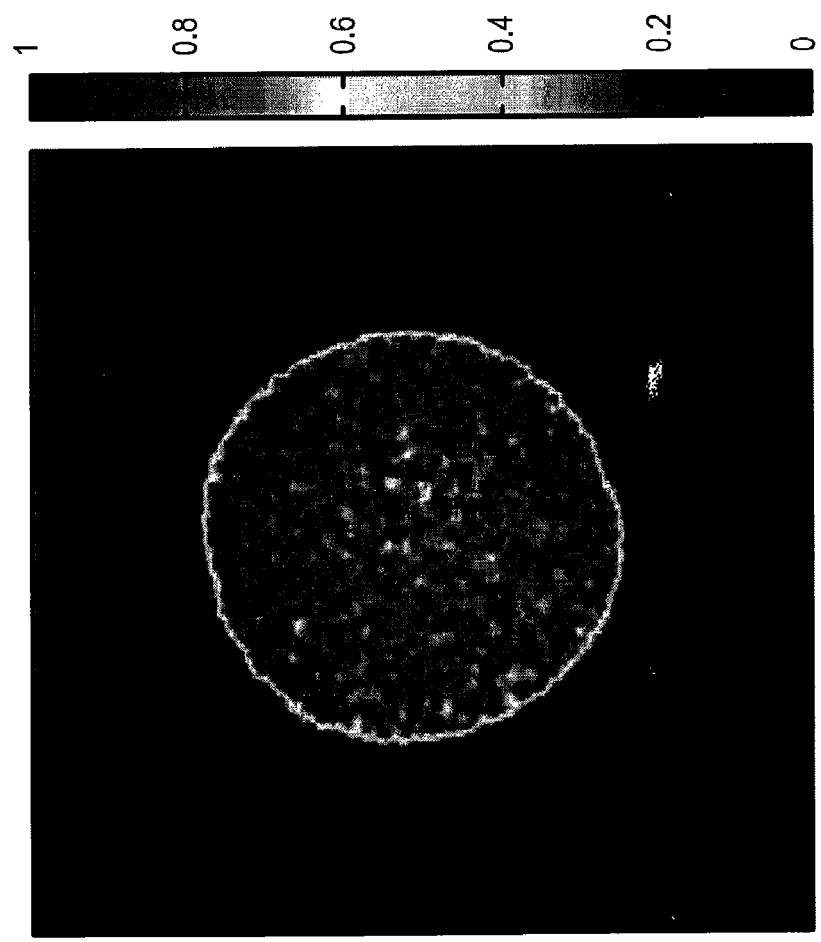
Figure 30C:
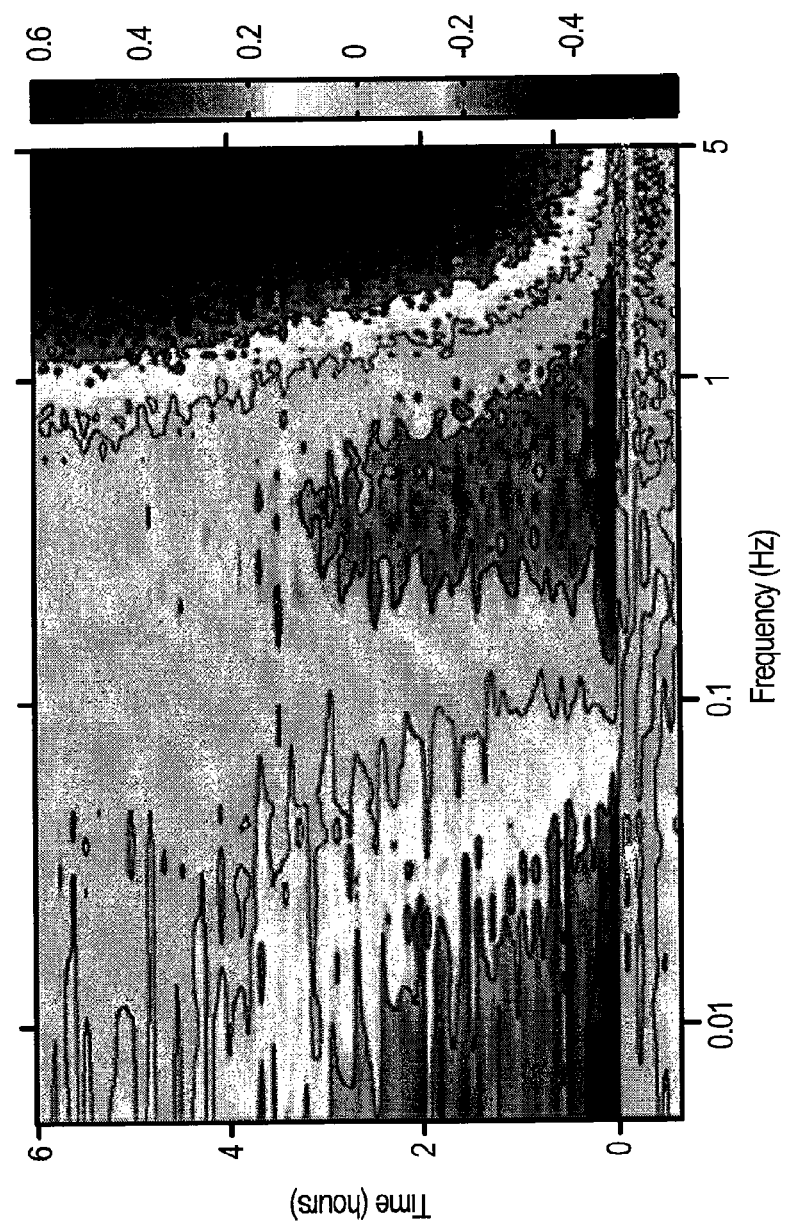
Figure 30D:
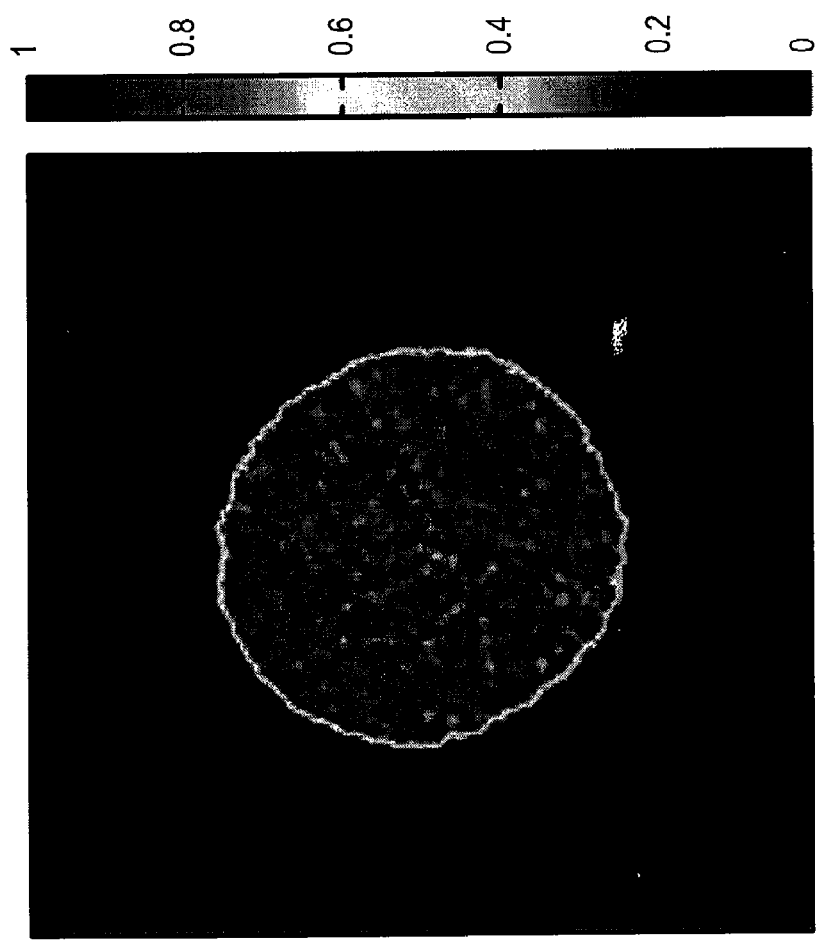
Figure 31A:
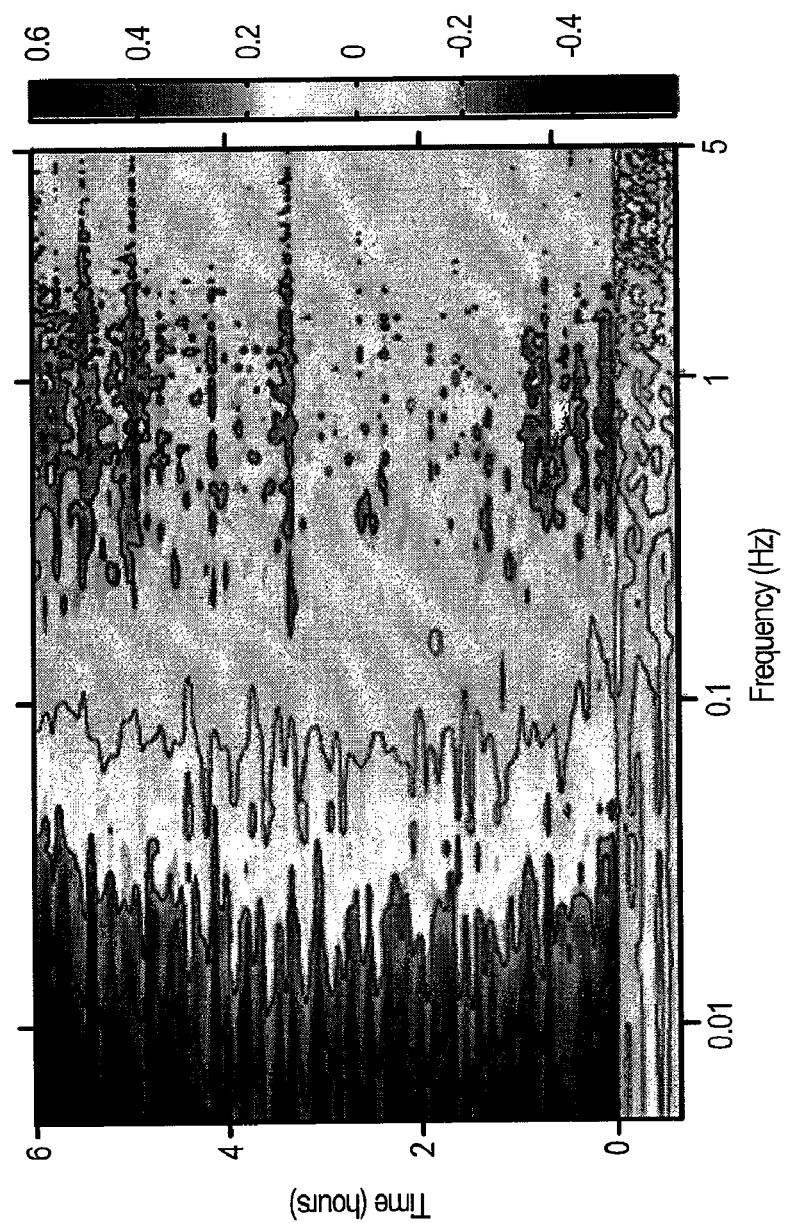
FIG. 31 shows spectrogram fingerprints for response to acidic (pH=6) and basic (pH=8) conditions.
Figure 31B:
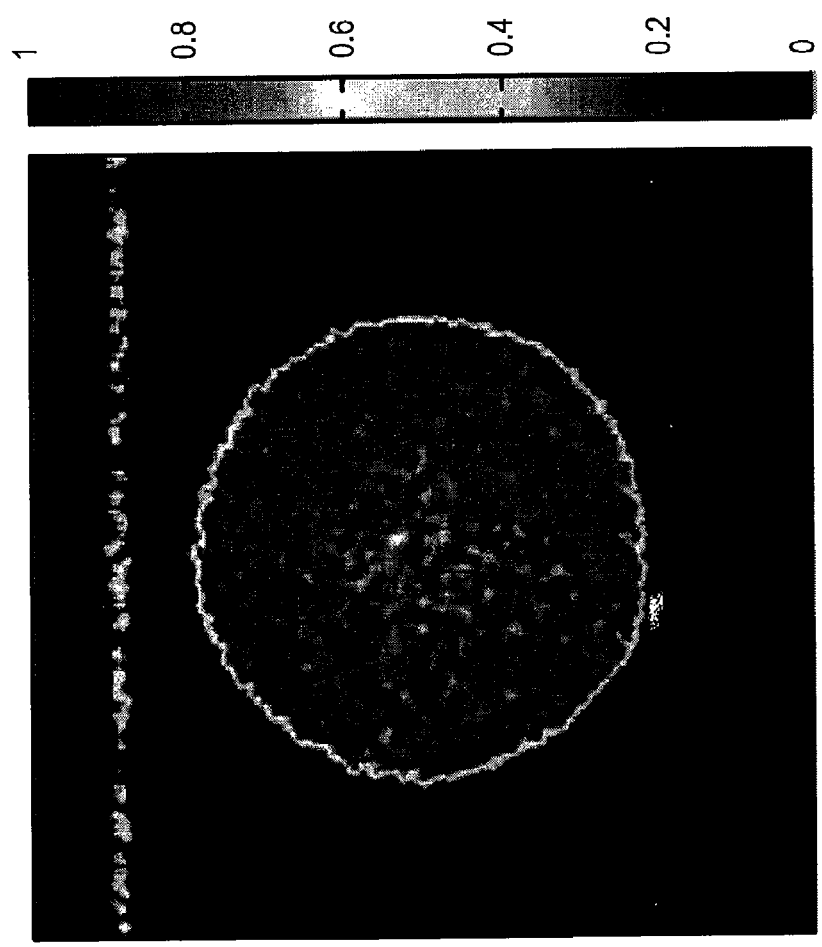
Figure 31C:
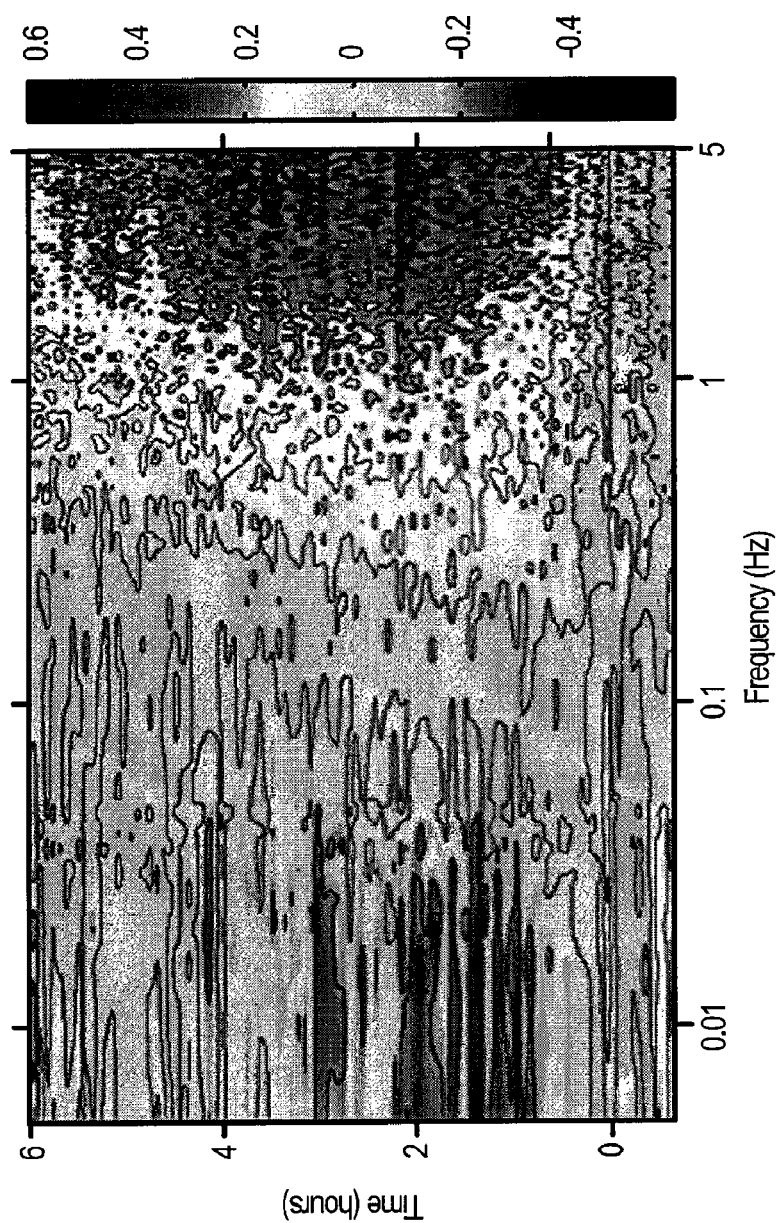
Figure 31D:
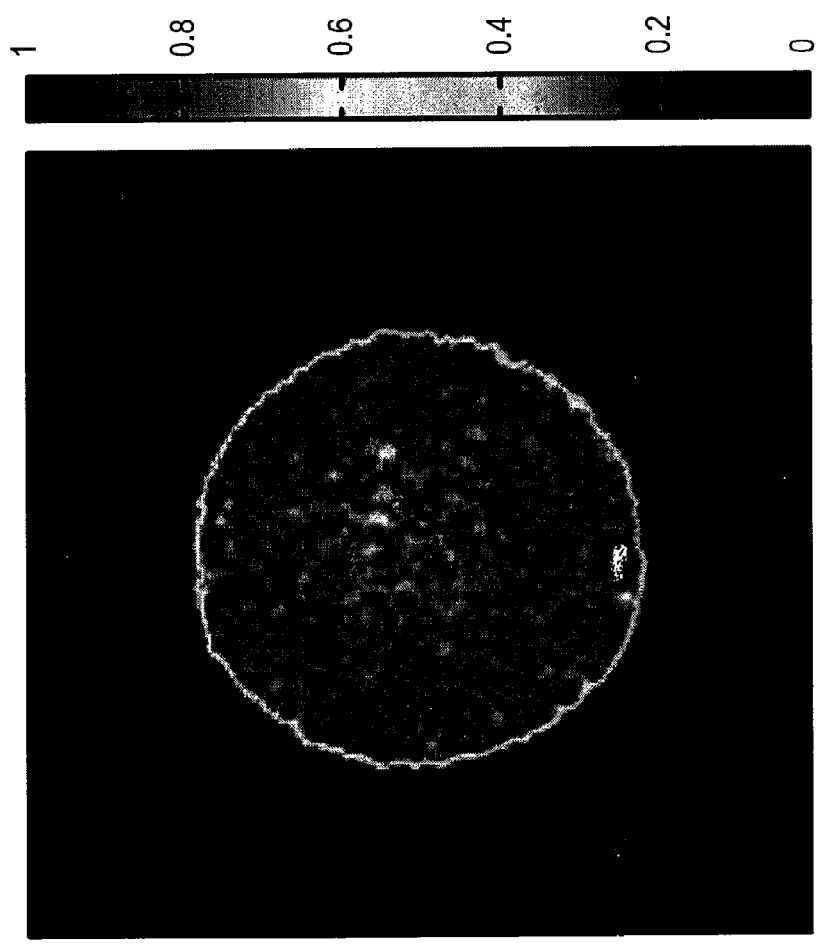
Figure 32A:
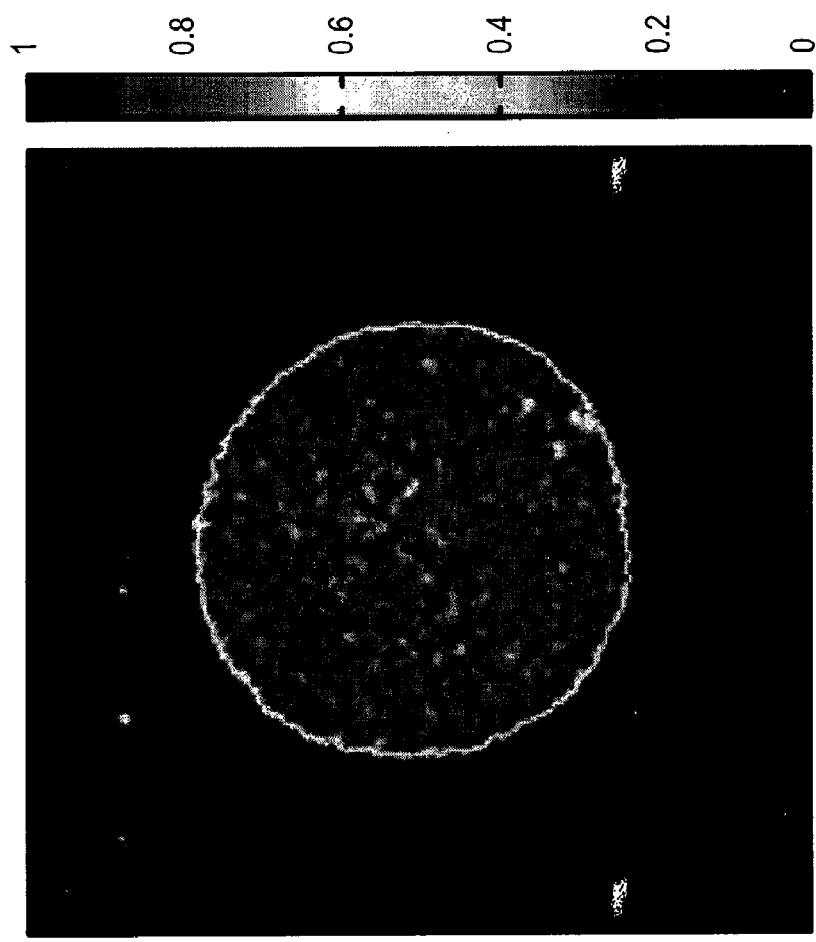
FIG. 32 shows a tumor responding to growth medium with no glucose.
Figure 32B:
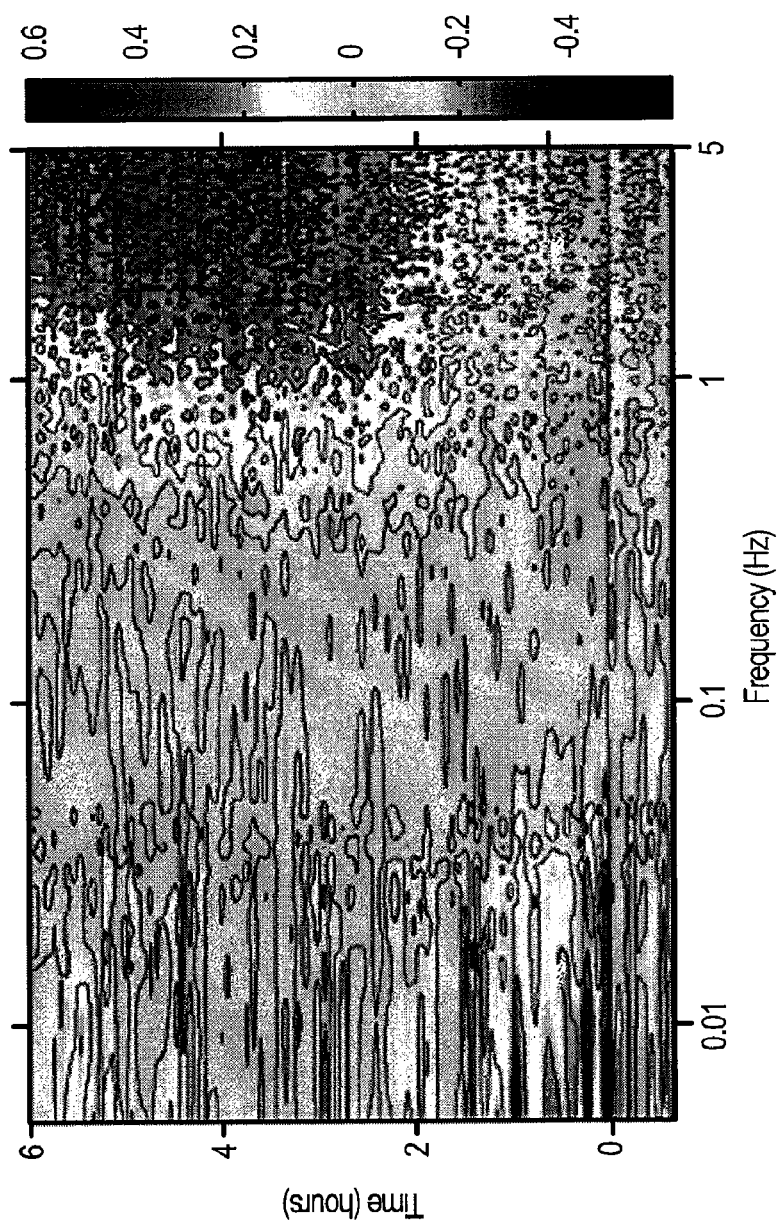
Figure 32C:
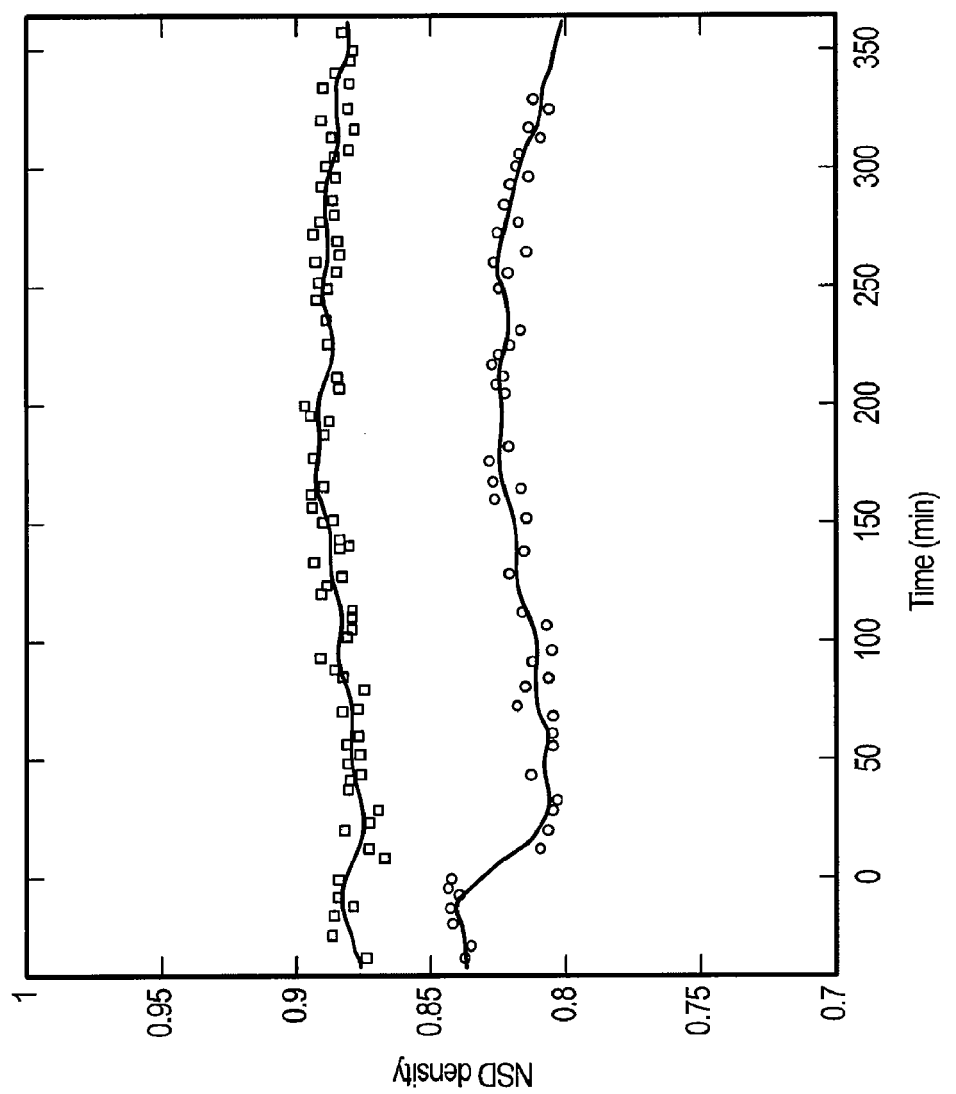
Figure 32D:
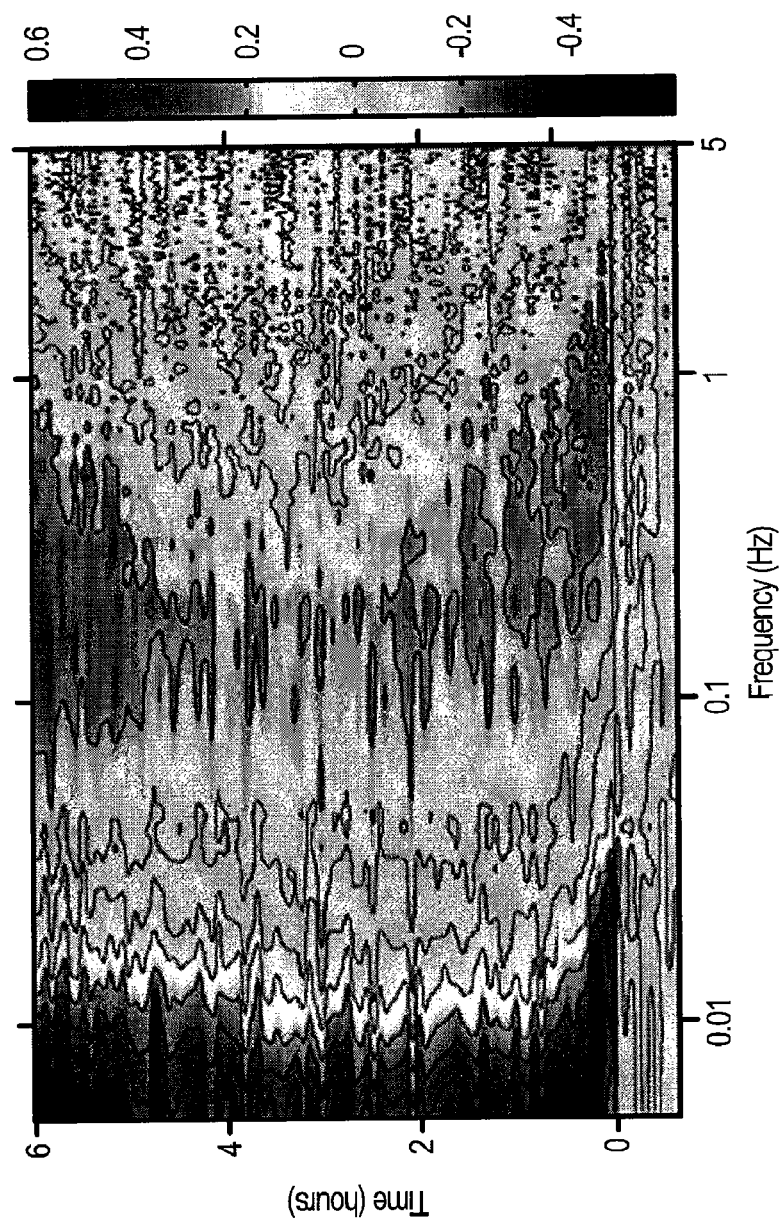
Figure 33A:
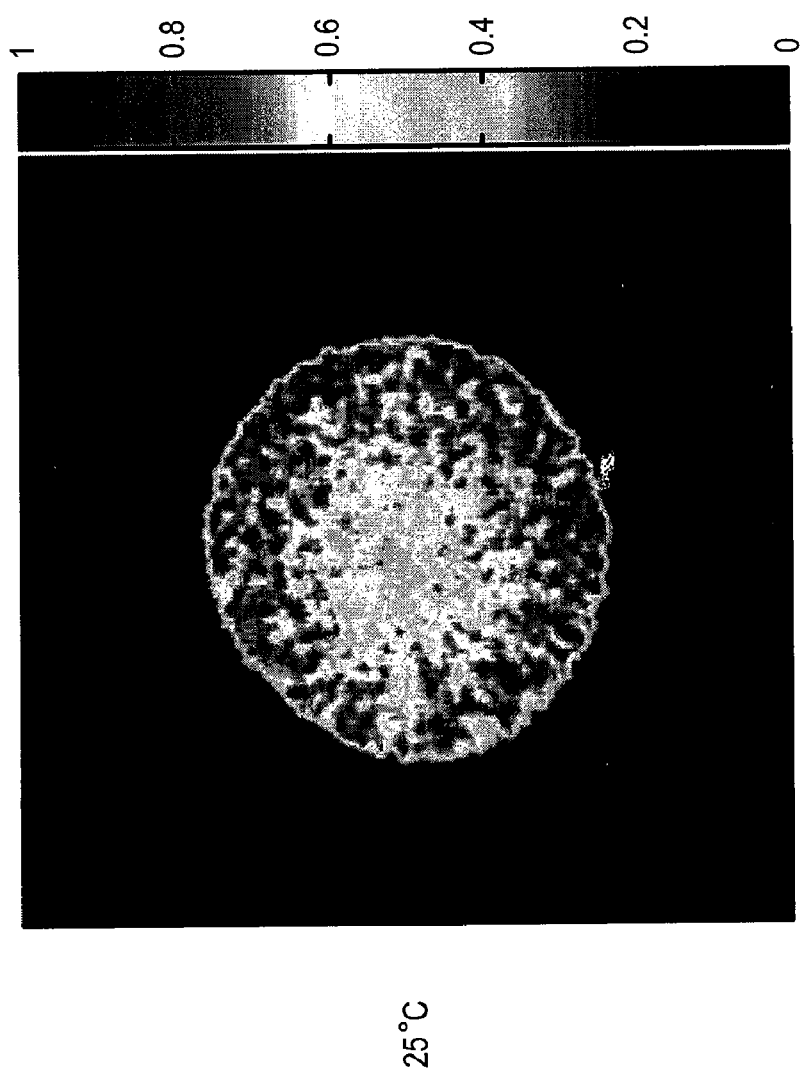
FIG. 33 shows the relative power spectral density for the application of cytochalasin D, where the mid-frequency band is enhanced which may represent enhanced membrane undulations;\
Figure 33B:
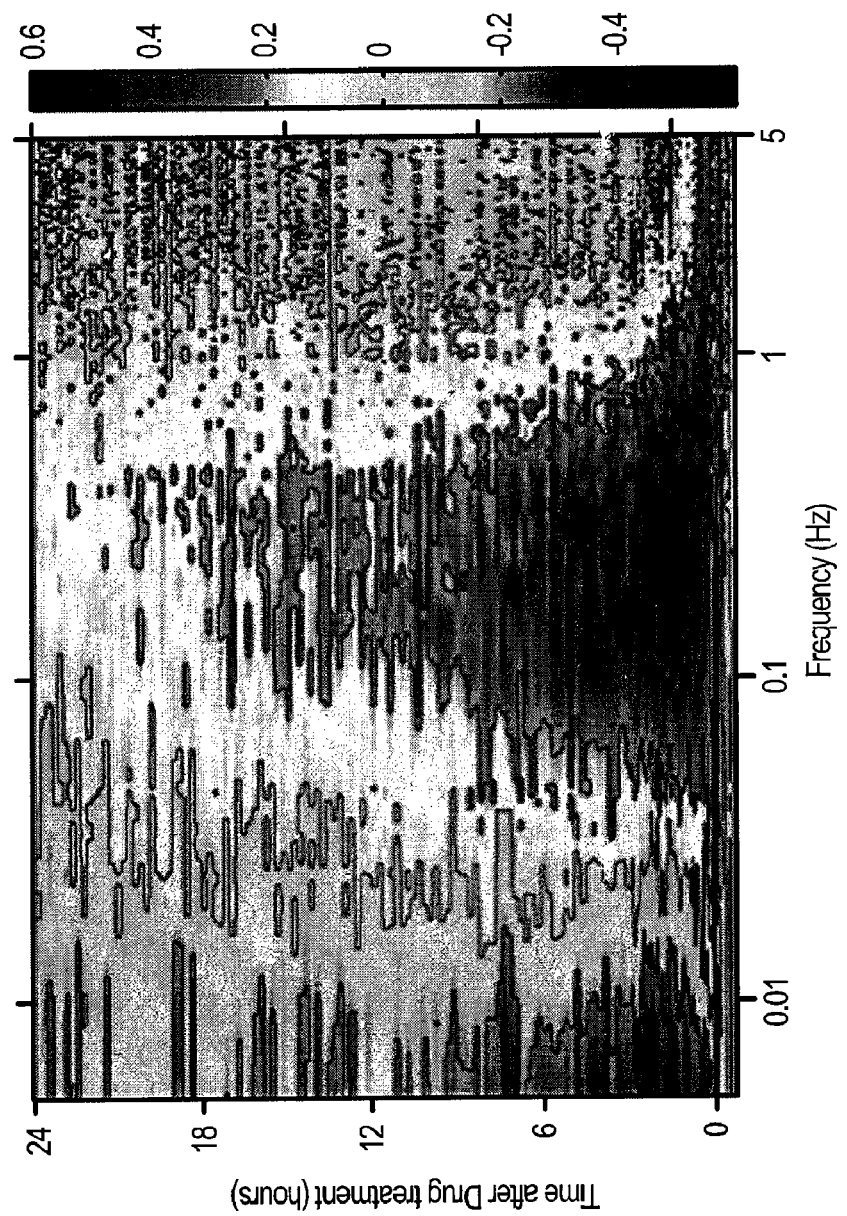
Figure 33C:
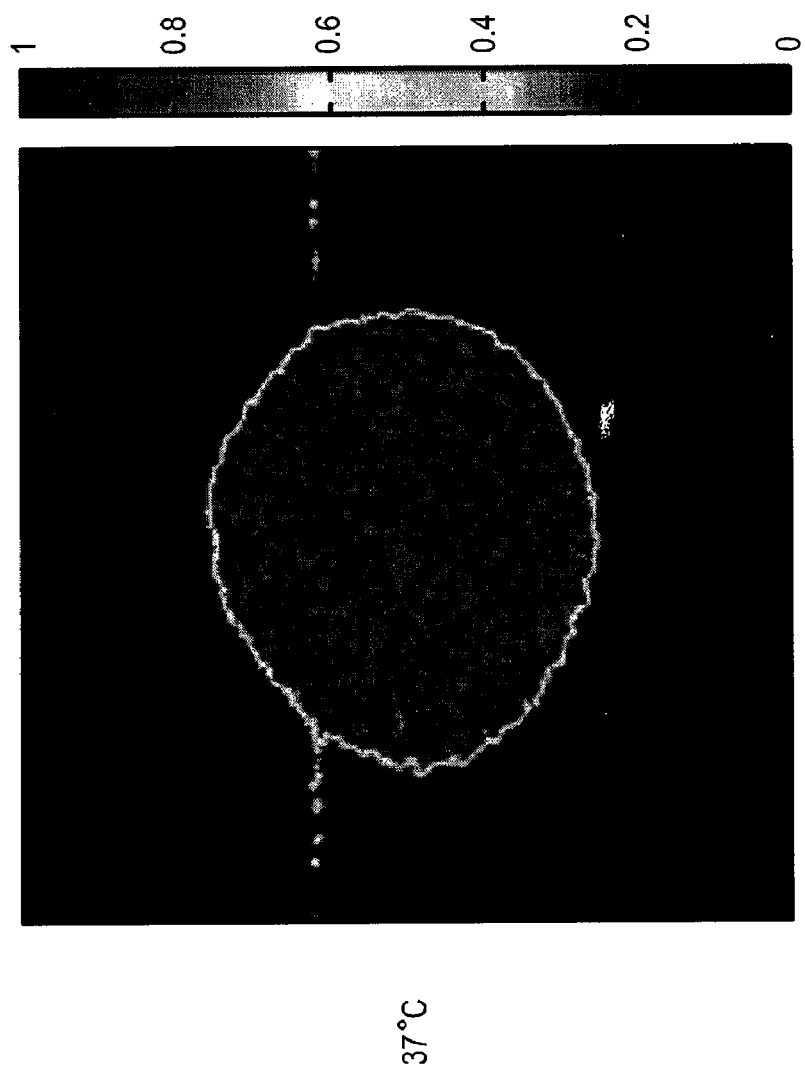
Figure 33D:
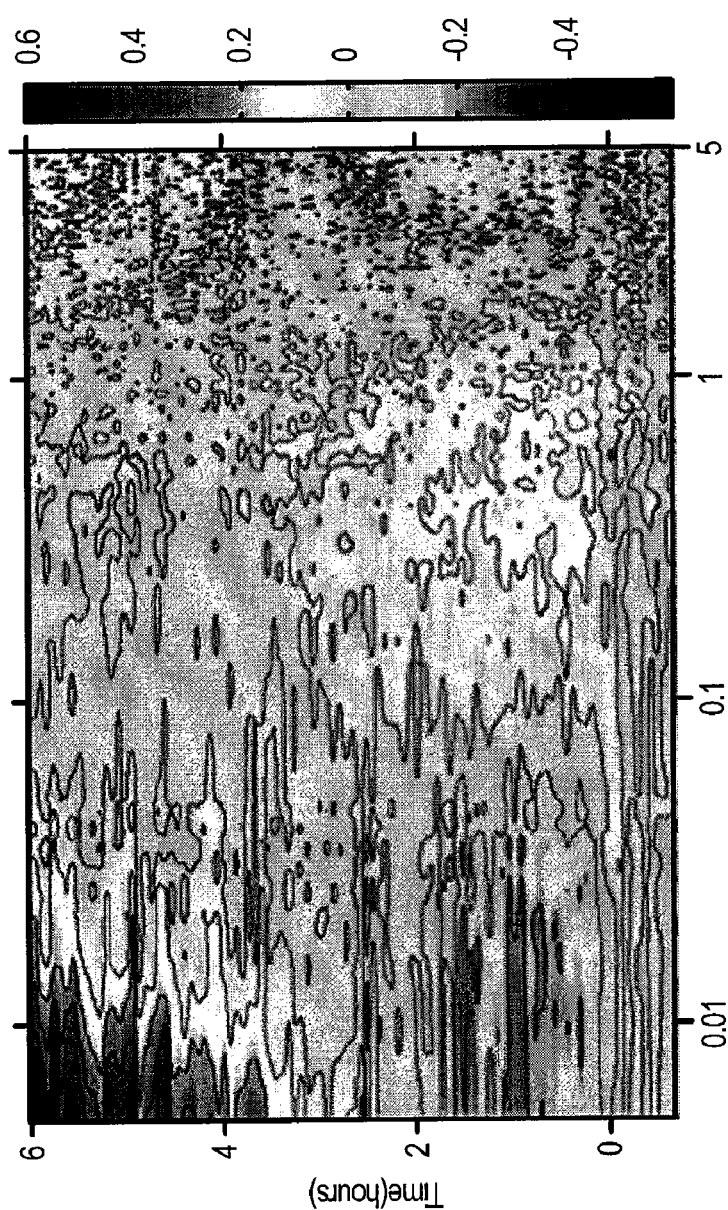
Figure 34A:
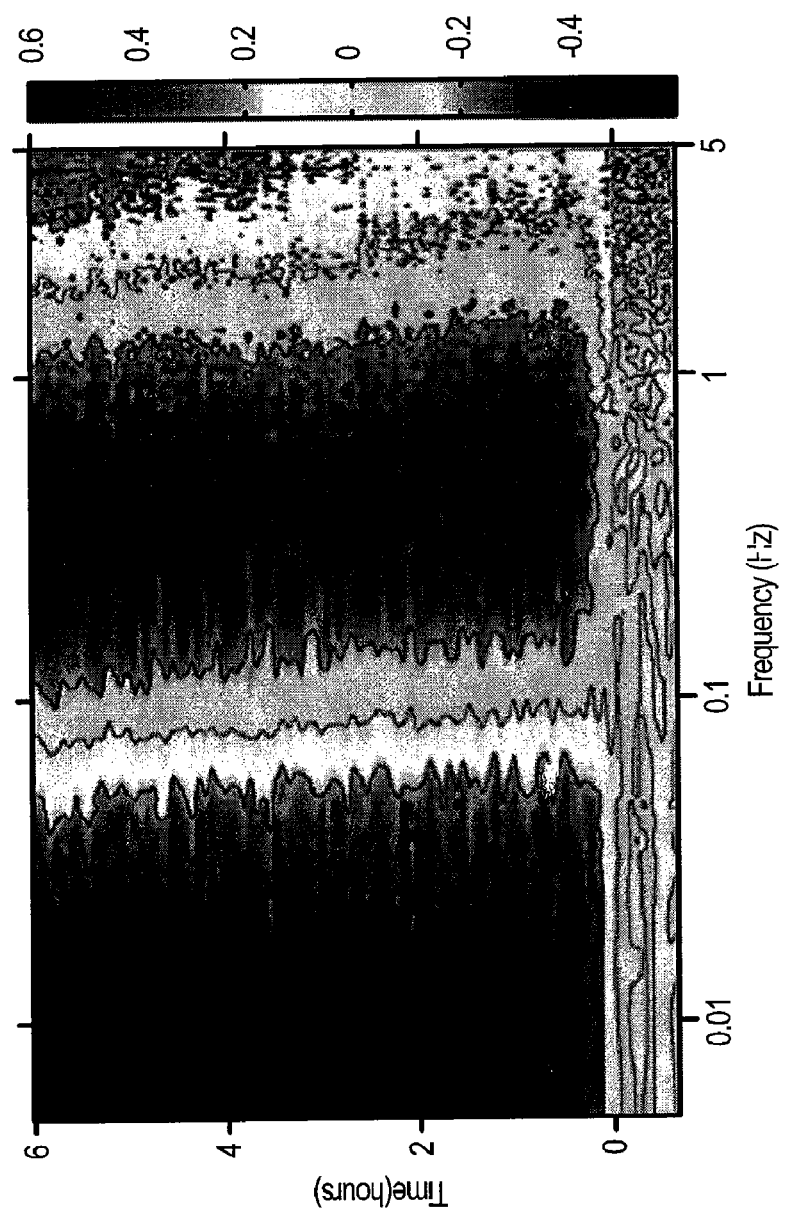
FIG. 34 shows spectrograms at a dose of 1 μg/ml for nocodazole in FIG. 34(a), colchicine in FIG. 34(b), paclitaxel in FIG. 34(c), and cytochalasin D in FIG. 34(d)
Figure 34B:
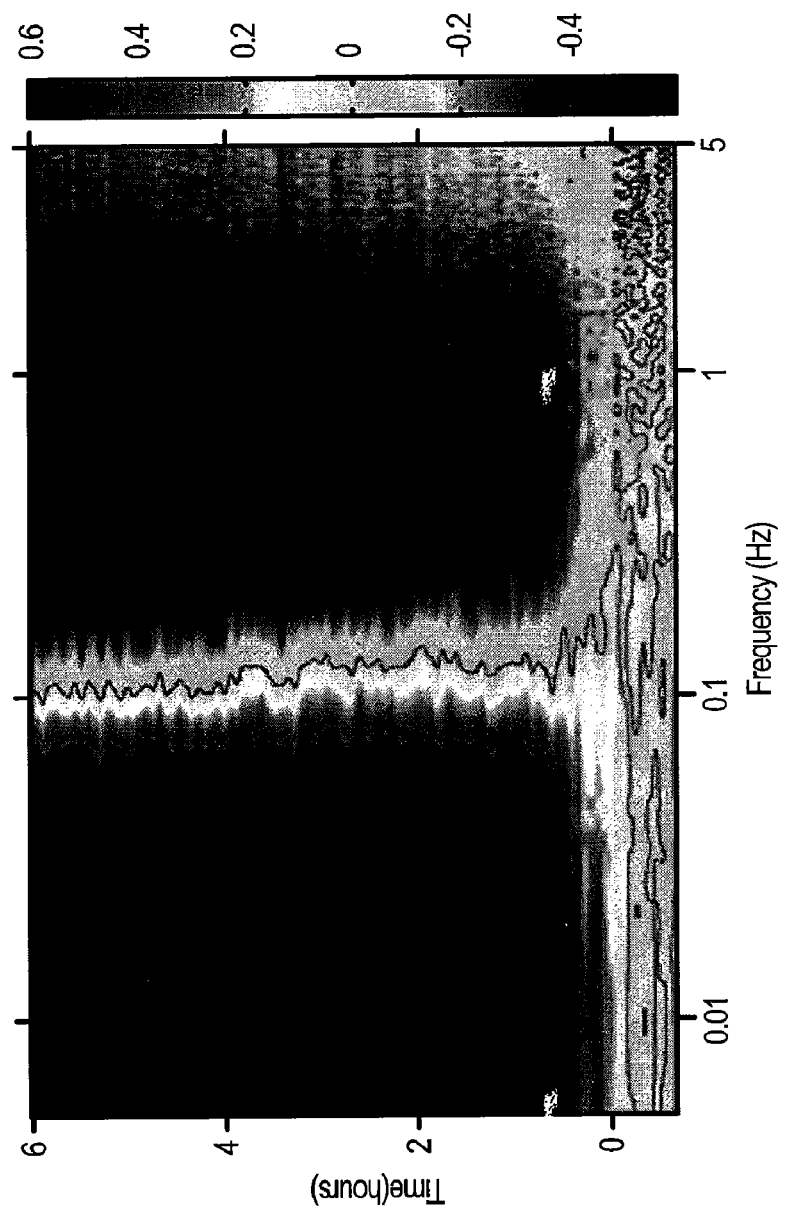
Figure 34C:
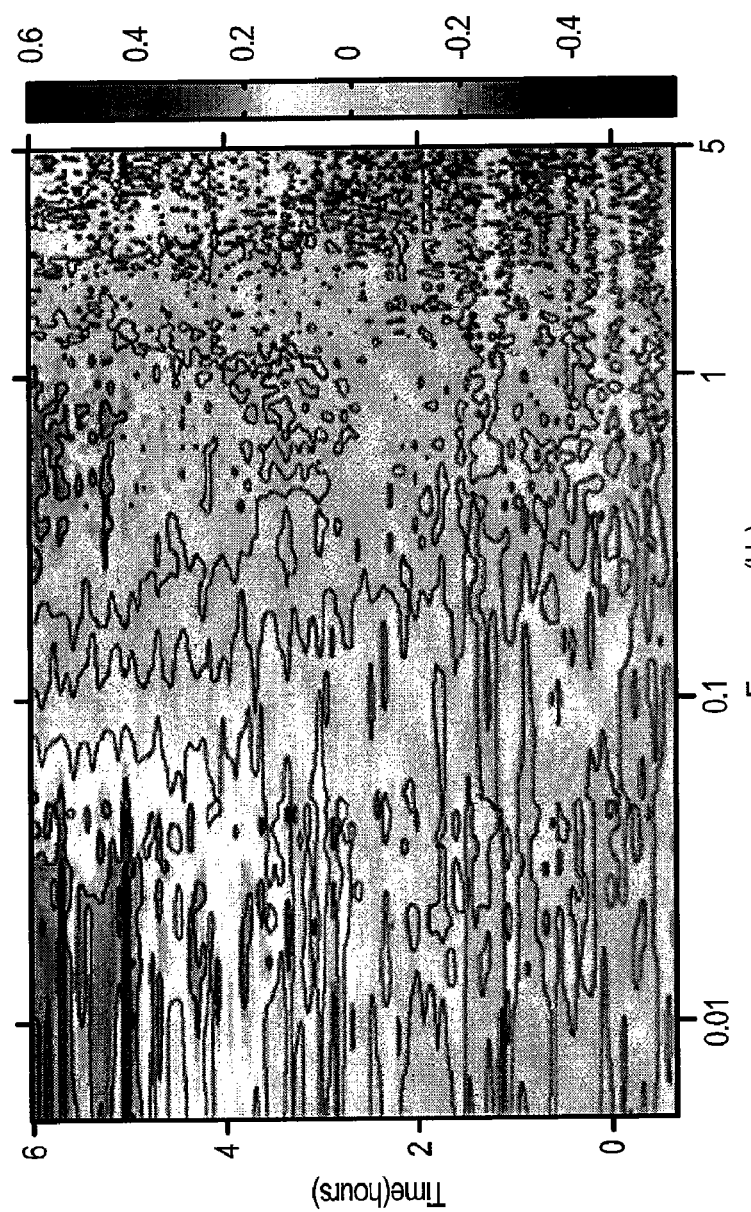
Figure 34D:
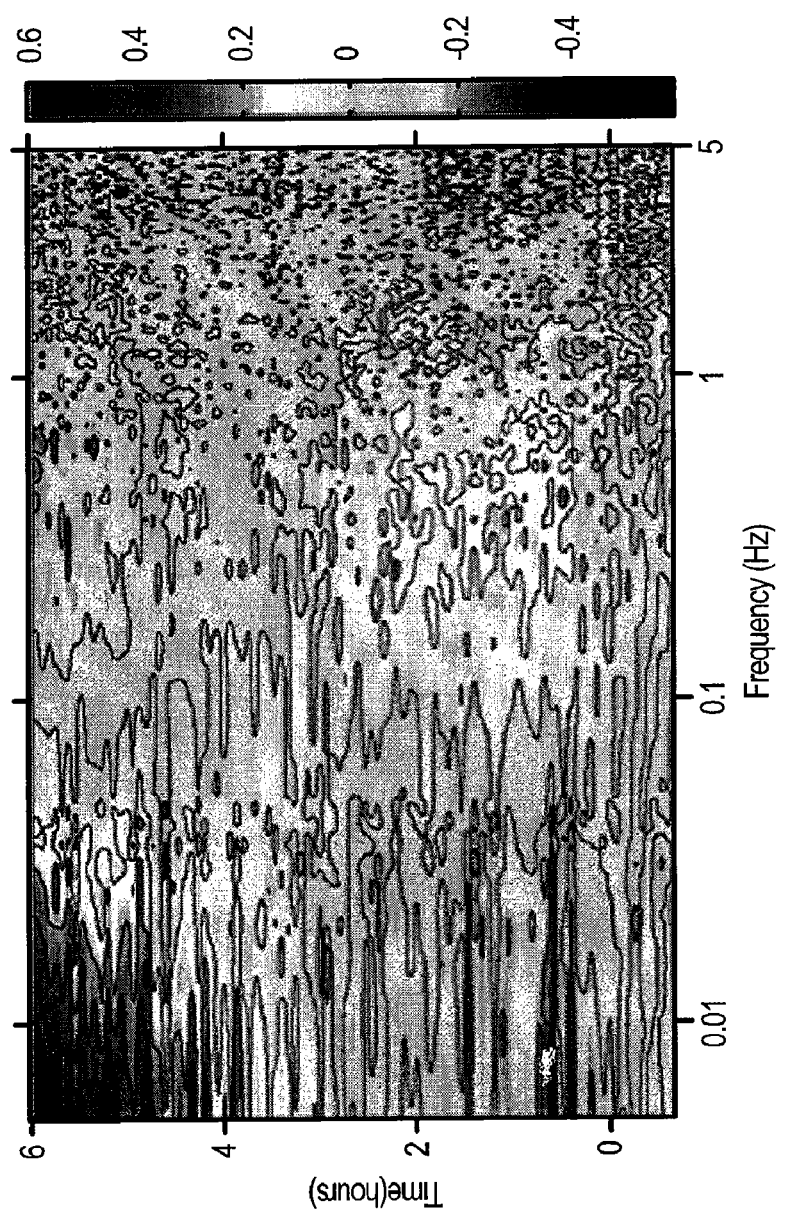

The spectral power density of a healthy tumor is shown in FIG. 24 for the proliferating shell and the necrotic core. The power spectra exhibit $1/f^n$ behavior from 0.01 Hz to about 0.5 Hz with n near unity. The shell is significantly more active than the core, but part of the core activity can be ascribed to the shimmering showerglass effect from the dynamic overlying tissue layers. The slopes of the power spectral density show slight breaks around 0.1 Hz and 0.5 Hz. The break near 0.5 Hz is likely due to Nyquist sampling, but the break near 0.1 Hz may have physical origins.

FIG. 25 shows a differential spectrogram of a negative control experiment of tumor responding only to normal growth medium with no drug treatment. The upper left image is a motility contrast image of the tumor. The differential spectrogram for the shell (upper right) and core (lower right), and the NSD density for the shell (upper curve) and the core (lower curve) are generally flat over 6 hours.

FIG. 26 shows the long-term effects of changing growth medium. The data in FIG. 26(a) are for 2 days without changing the growth medium. The data in FIG. 26(b) are for 2 days while changing the growth medium every 8 hours. In each figure, upper left image is a motility contrast image of the tumor; the differential spectrogram for the shell is shown on the upper right, the differential spectrogram for the core is shown in the lower right, and in the NSD density graph, the shell is the upper curve and the core is the lower curve. Without new growth medium, the tissue degrades significantly after 12 hours. Even with replenished growth medium, the healthy shell shows a strong shift to lower frequencies after about 8 hours. However, the core is significantly stabilized by the replenishment of the growth medium.

Temperature and Heat Shock

The spectral difference in response to changes in temperature is shown in FIG. 27 for a 400 mm diameter tumor as the temperature is increased from 24° C. to 37° C., then up to 43° C. (which is lethal for long exposure times to cells) and returned to physiological 37° C. The upper left image is a motility contrast image of the tumor. The frequency range spans from 0.003 Hz to 5 Hz. The baseline at 24° C. is flat, then there is significant increase in the higher frequencies as the temperature rises to 37° C. and then to 43° C. Once at 43° C., the enhancement in high frequency motion begins to decay. One of the most important findings in this experiment is the behavior after the tissue is returned to the physiological 37° C. temperature. The spectrograms show clear differences post-heat shock to pre-heat shock. The differential spectral densities for the shell are shown in the upper spectrogram and for the core in the lower spectrogram. In particular, there is an increase in the ultralow frequencies, which might be indicative of blebbing. Note too that the core, which is not fully necrotic in this tumor, but is hypoxic, shows stronger low-frequency enhancement, while the proliferating shell shows stronger high-frequency enhancement. The high frequencies are associated with organelle and vesicle motions, which in the proliferating shell may be associated with apoptosis, while the hypoxic core undergoes necrosis in response to the heat shock.

Figure 2B:
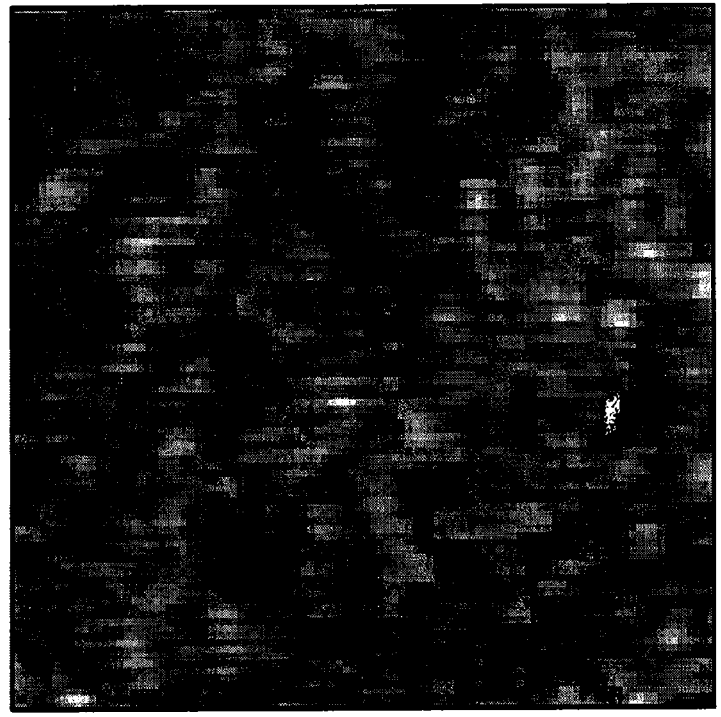
FIG. 2(b) shows a magnified portion of FIG. 2(a) where the spatial interference fringes modulate the speckle pattern with approximately 2-3 fringes within a speckle coherence length.
Figure 2A:
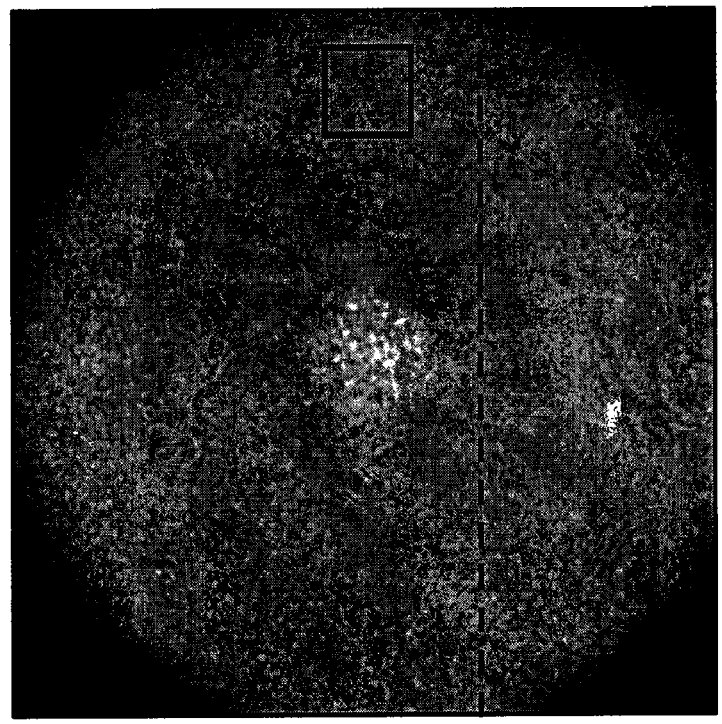
FIG. 2(a) shows full field holographic data
Figure 3:
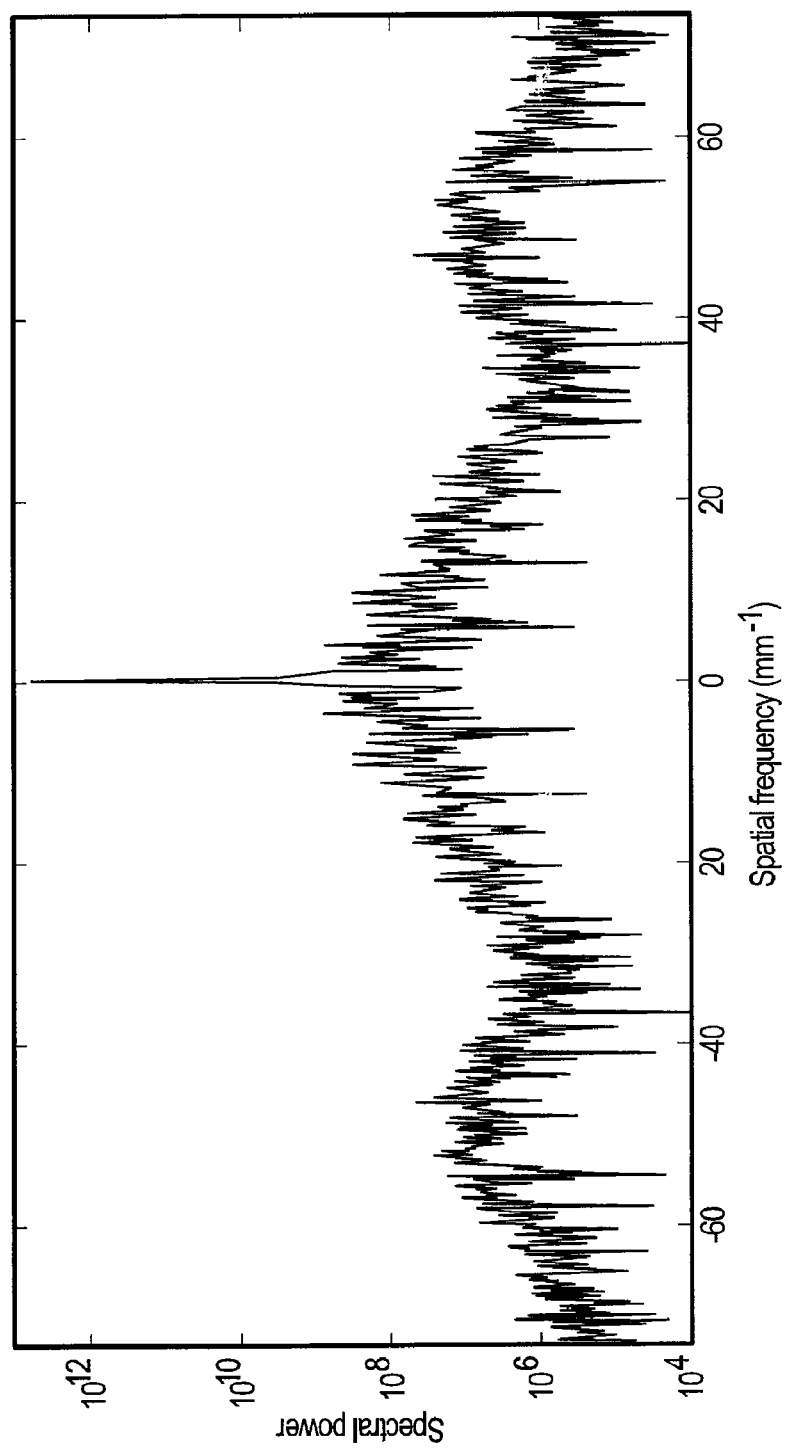
FIG. 3 shows the Fourier transform of the data along the dashed line in FIG. 2(a) where the two broad sideband peaks represent the image information.
Figures 4A, 4B:
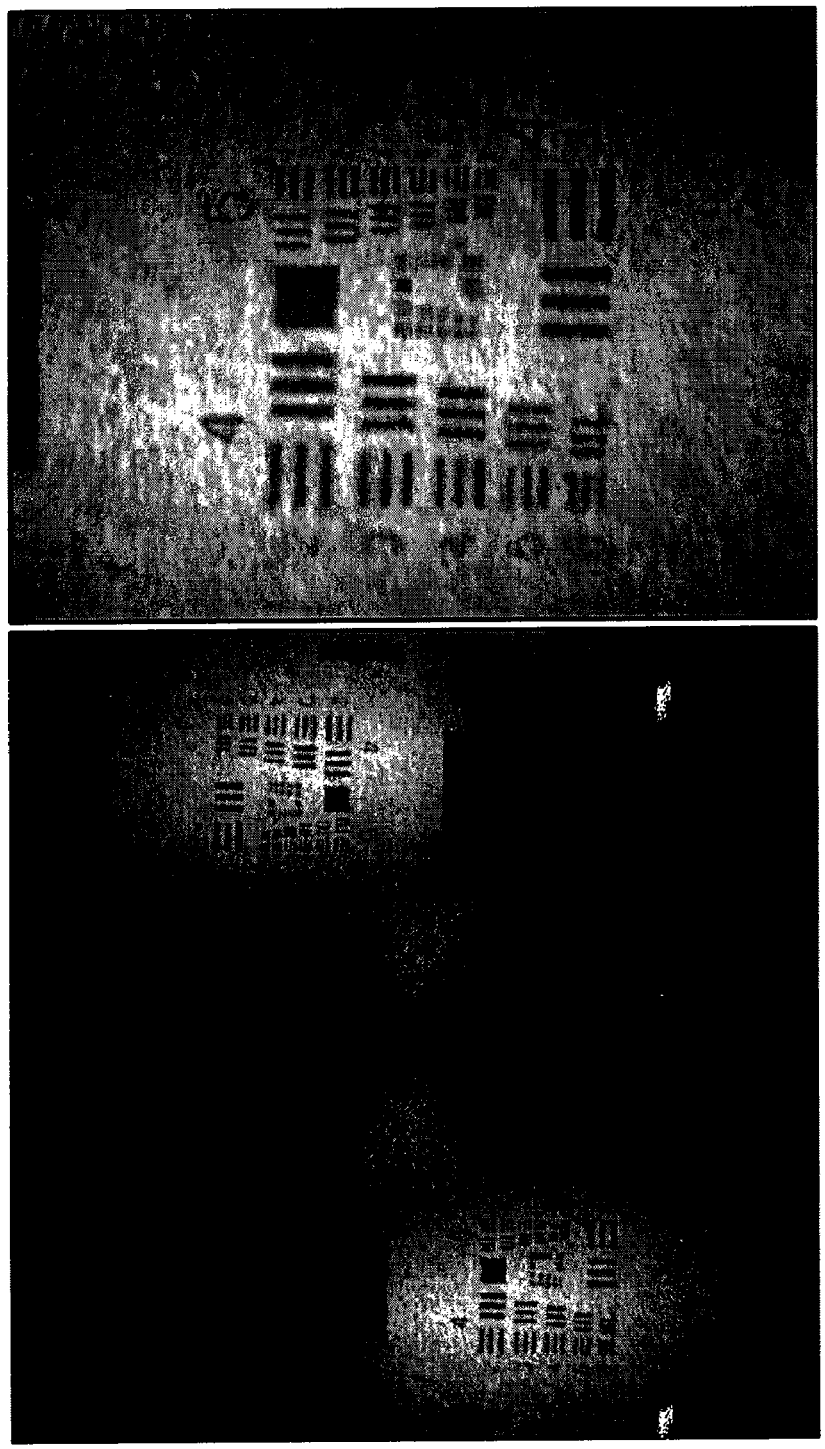
FIG. 4(a) shows demodulated and transformed images showing the direct image and its conjugate.
FIG. 4(b) is a magnified version of the lower-left reconstruction in FIG. 4(a)

The spectral difference in response to changes in temperature is shown in FIG. 2 for a tumor beginning at the physiological temperature of 37° C. and heat to 43° C. for only 10 minutes before returning to physiological temperature. The upper left image is a motility contrast image of the tumor. The differential spectrogram for the shell is shown on the upper right, the differential spectrogram for the core is shown in the lower right, and in the NSD density graph, the shell is the upper curve and the core is the lower curve. The frequency range spans from 0.003 Hz to 5 Hz. The thermal increase is most apparent in the shell in the high frequency band, and returns to normal after the temperature is decreased. There is no strong heat shock response.

Osmolarity

Osmolarity has a strong effect on the uptake of water into cells and tissue. Hypotonic conditions lead to strong cellular swelling (edema) and possibly bursting the cell, while hypertonic conditions desiccates the cells and causes them to contract. The change in the relative spectral density was monitored as the osmolarity of the growth medium around tumors was changed. The results of tumors responding to hypo- and hyper-osmolarity at room temperatures of 25° C. are shown in FIG. 29, and at physiological temperature of 37° C. in FIG. 30. In each of FIGS. 29 and 30, the differential spectrograph and motility contrast image for the hypotonic condition is on the left is and for the hypertonic condition is on the right. The osmolarity is changed from isotonic (300 mOsm) at zero minutes.

In FIG. 29, at room temperature, the osmolarity was changed from isotonic (300 mOsm) to hypotonic osmolarity (200 mOsm) on the left, and to hypertonic osmolarity (400 mOsm) on the right. The hypotonic condition caused an initial increase in higher frequencies, followed by a relaxation back to normal behavior. This transient effect is likely caused by the cell re-establishing homeostasis after the osmotic shock. However, for hypertonic conditions, there is no relaxation back to homeostasis.

In FIG. 30, at physiological temperature, the osmolarity was changed from isotonic to hypotonic osmolarity (150 mOsm) on the left, and to hypertonic osmolarity (500 mOsm) on the right. The initial transients are similar to those at room temperature, but both the hypo and hyper-tonic conditions decay rapidly (within minutes) and are followed by a much stronger longer-term behavior. For the extended hypotonic condition (cell swelling), the low frequencies are significantly enhanced. For the extended hypertonic condition (cell shrinkage), the high frequencies are enhanced.

The initial transient responses may be understood in terms of cell swelling and shrinking Desiccation of the cytosol under hypertonic conditions shrinks the cell volume, increases the viscosity, and increases the density of intracellular constituents, significantly impeding motion. This is reflected in the initial increase of the low frequencies. However, membrane vesicles may still be active as the cell tries to reestablish stasis. The vesicle activity might be the source of the high-frequency band increase for the hypertonic condition at long times. Conversely, cellular swelling under the hypotonic conditions increases the cell volume, decreases the density of intracellular constituents and reduces the viscosity. This leads to the initial increase in the high frequency motion that then decays. The longer-term low frequency enhancement may be the actual motions of the expanding cell membranes.

Response to pH

The pH of the growth medium is an important factor in tissue stasis. For instance, if the CO2 increases above 5% in the gas over the growth medium this can lead to acidification of the growth medium and decreased viability of the cells and tissues. FIG. 31 shows spectrogram fingerprints of tumors responding to pH of 6 (acidic) (left side) and pH of 8 (basic) (right side) growth medium are shown in FIG. 31. The acidic conditions slow down the intracellular motions. Conversely, the basic conditions enhance the higher frequencies, but less strongly, corresponding to more organelle motions.

Response to Hypoglycemia

A tumor responding to exposure to growth medium that has no glucose is shown in FIG. 32. A motility contrast image of the tumor is shown in the upper left. The differential spectrogram for the shell is shown on the upper right, the differential spectrogram for the core is shown in the lower right, and in the NSD density graph, the shell is the upper curve and the core is the lower curve. The healthy shell shows a weak initial response of suppressed high frequencies that then flips polarity as the high frequencies become enhanced. The hypoxic core, on the other hand, shows a strong increase of the ultralow frequencies (associated with membrane shape or cell motion), and suppression of the mid frequency range. This striking difference in the responses of the core and shell may reflect the different oxygen tension in these two materials. Glycolysis is the main metabolic pathway, and availability of oxygen is an important constituent in the different pathways for oxydative phosphorylation and anaerobic glycolysis.

Response to Anti-Mitotic Drugs

The most active use of the cytoskeletal machinery occurs during mitosis in which the entire cellular structure is reorganized prior to and during division. During mitosis, the microtubules form the mitotic spindle which is an organized mechanical structure that helps divide the intracellular contents for cell division. Actin plays an important role in cytokinesis at the end of mitosis when the cell membrane pinches off, and the cell physically divides. For these reasons, drugs that inhibit the motors and their tracks are common anti-cancer agents, arresting the cell cycle by arresting motion.

The largest class of anti-cancer therapeutic agents are known as anti-mitotic drugs (AMD), also called cytoskeletal drugs. These drugs affect the cellular cytoskeleton and prevent cells from entering the mitosis phase of the cell cycle. Common anti-mitotic drugs are colchicine, nocodazole, cytochalasin and taxol. These arrest mitosis through different mechanisms. Colchicine and nocodazole inhibit tubulin polymerization at the leading edge of the microtubules, which causes the degradation of microtubules in the cytosol through the process known as treadmilling that causes the microtubules to depolymerize at the opposite end. Taxol influences the microtubules by using a different mechanism that inhibits microtubule depolymerization and thus stabilizes the microtubules. Many of the microtubule-associated mitotic processes require dynamic instability and treadmilling, which are suppressed by Taxol stabilization of the microtubules. Cytochalasin is an actin drug that inhibits actin polymerization which degrades the cell cortex and prevents cytokinesis.

Cytochalasin D was applied to the tumor spheroids and monitored the relative changes in the fluctuation power spectral density. The results of an experiment that applied cytochalasin D are shown in FIG. 33 at room and at physiological temperatures. The upper spectrograph is for the shell at room temperature with 50 μg/ml of cytochalasin D applied. The lower spectrograph is for the shell at physiological temperature with 10 μg/ml of cytochalasin D applied. After the application of the dose, the middle-frequency fluctuations are enhanced. Because cytochalasin suppresses the actin cortex, which help give the cell membrane its rigidity, the enhanced mid-range frequency may represent larger membrane undulations.

The spectrograms of the four anti-mitotic drugs cytochalasin, nocodazole, taxol and colchicine are shown in FIG. 34 at a dose of 1 μg/ml. FIG. 34(*a*) shows nocodazole, FIG. 34(*b*) shows colchicine, FIG. 34(*c*) shows paclitaxel, and FIG. 34(*d*) shows cytochalasin. Nocodazole and Colchine both have the same mechanism of action—suppression of the microtubules in the cytoskeleton. Both show very similar spectrogram fingerprints with significant enhancement of lower frequencies. Paclitaxel (Taxol) shows only a weak change, which is consistent with its microtubule stabilization effects. Cytochalasin shows an enhancement of the mid-frequencies for about 2 hours after application of the drug, followed by a shift of the spectral weight to lower frequencies.

Figure 35A:
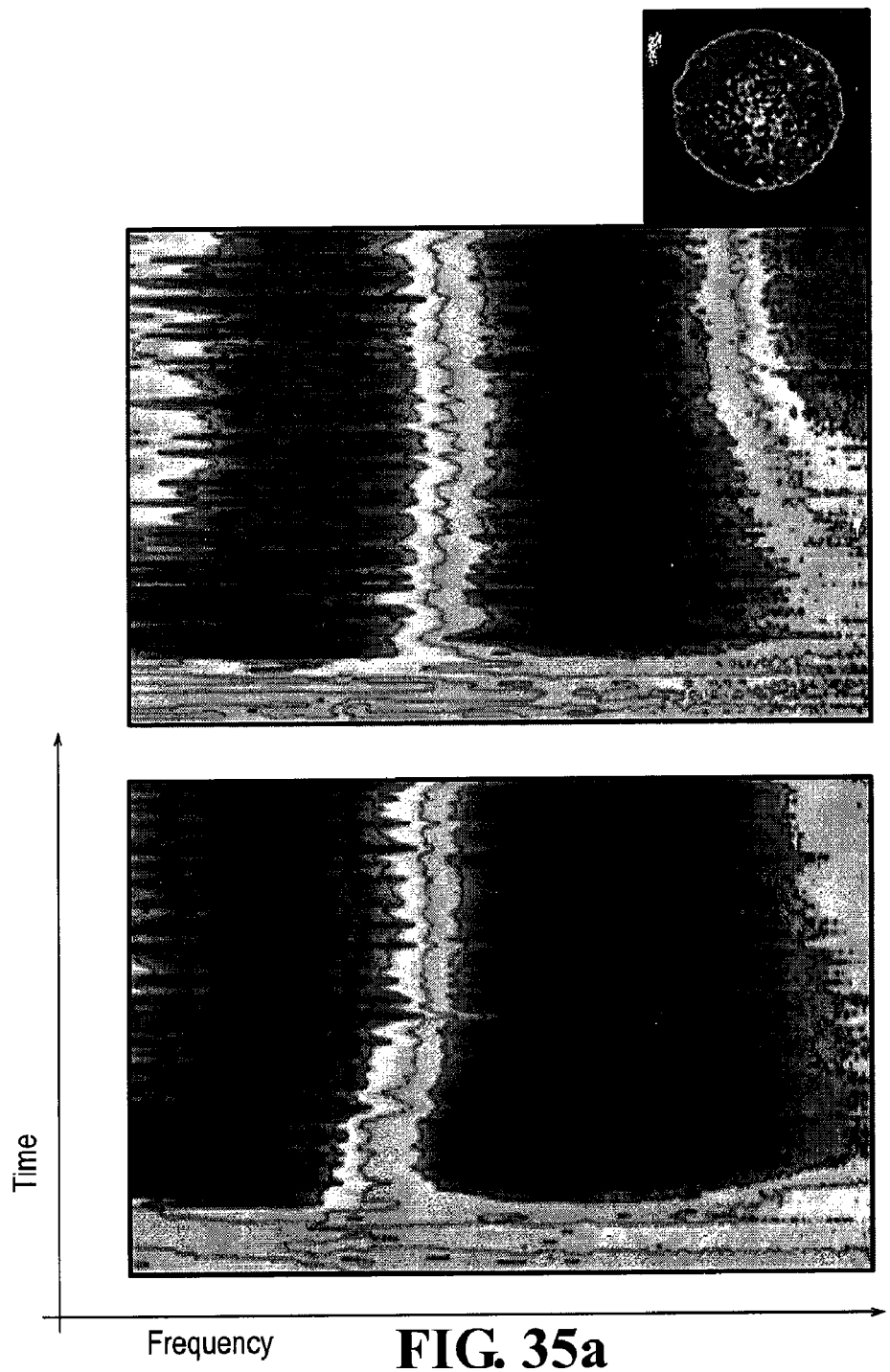
FIG. 35 shows a core-shell comparison between microtubule destabilizing (colchicine) (FIG. 35(a)) stabilizing (taxol) (FIG. 35(b)) drugs where the high-frequency organelle activity appears only in the healthy shell and not in the core
Figure 35B:
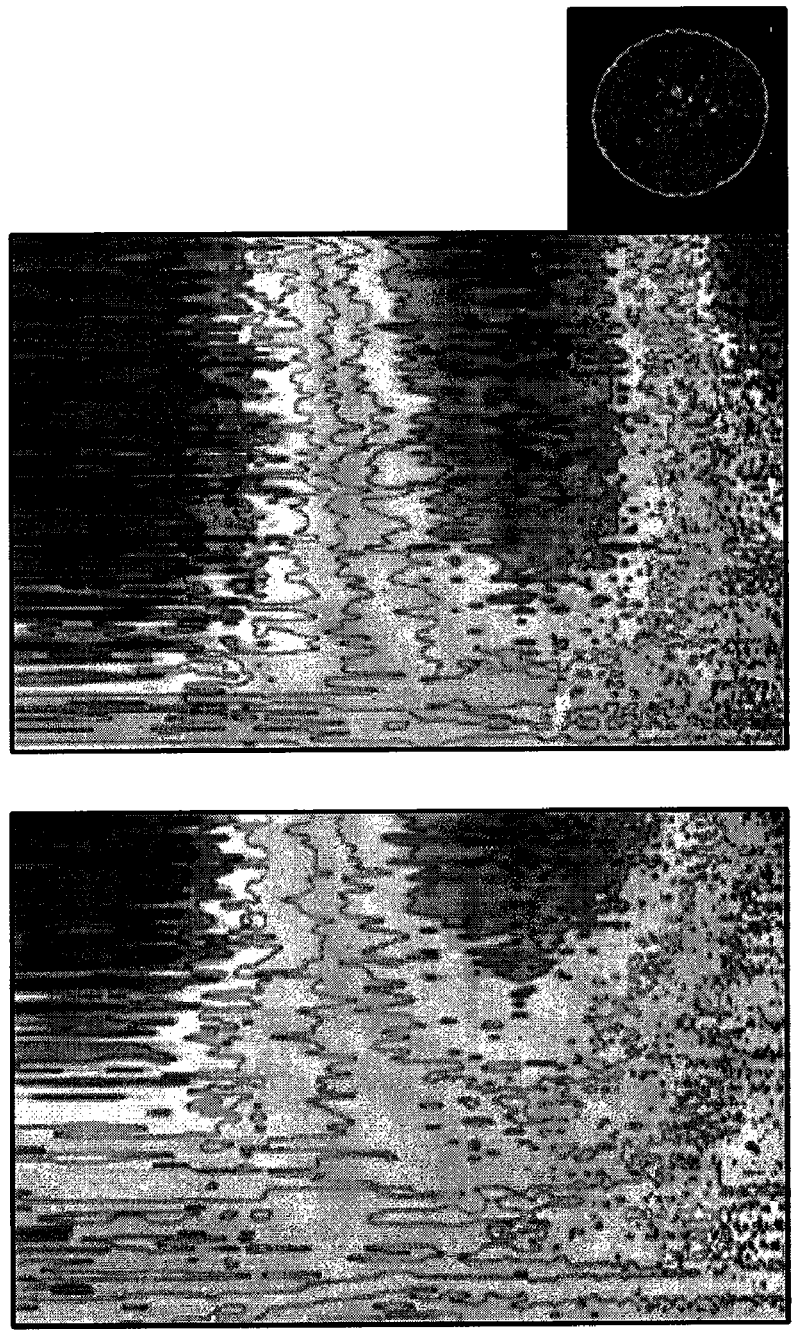

FIG. 35 shows a core-shell comparison between microtubule stabilizing (taxol) and destabilizing (colchicine) drugs. FIG. 35(*a*) (left side) shows the results for colchicine and FIG. 35(*b*) (right side) shows the results for taxol. For each drug, the upper spectrogram is for the shell and the lower spectrogram is for the core. The high-frequency organelle activity appears only in the healthy shell and not in the core.

Metabolic Drugs

Figure 37A:
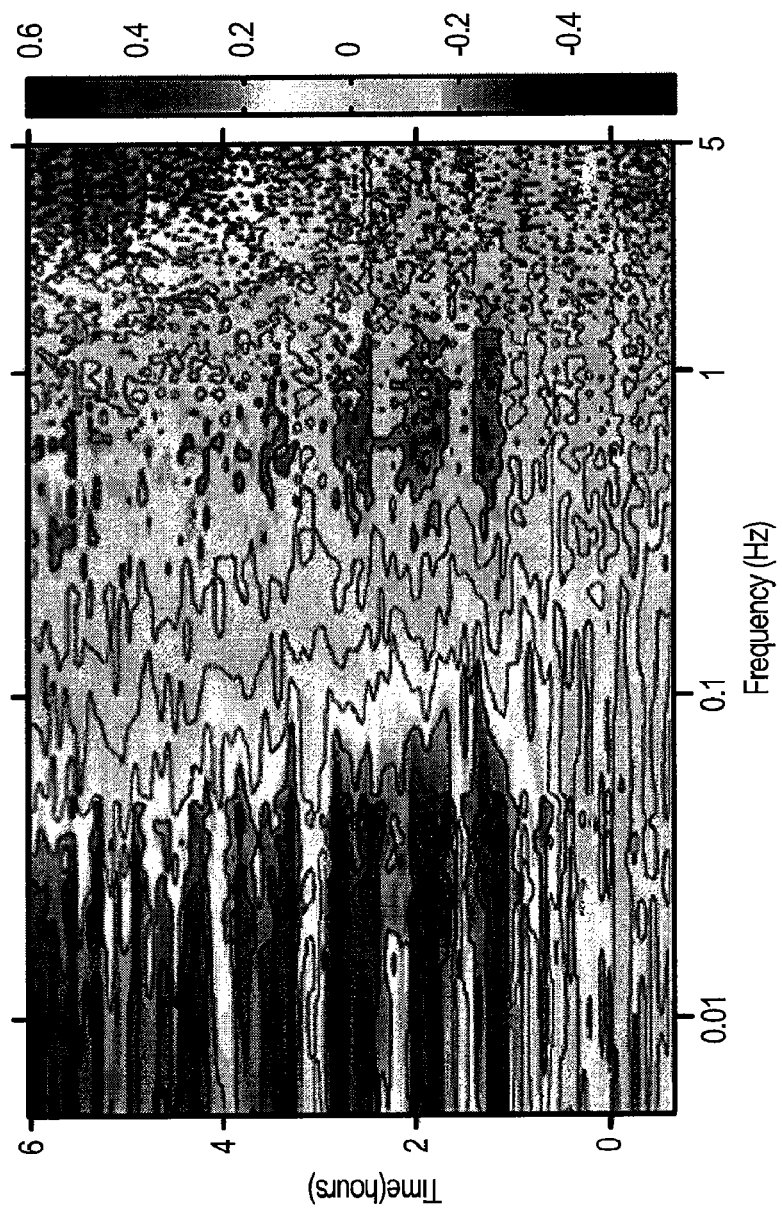
FIG. 37 shows induced oscillations caused by iodoacetate at 37° C.
Figure 37B:
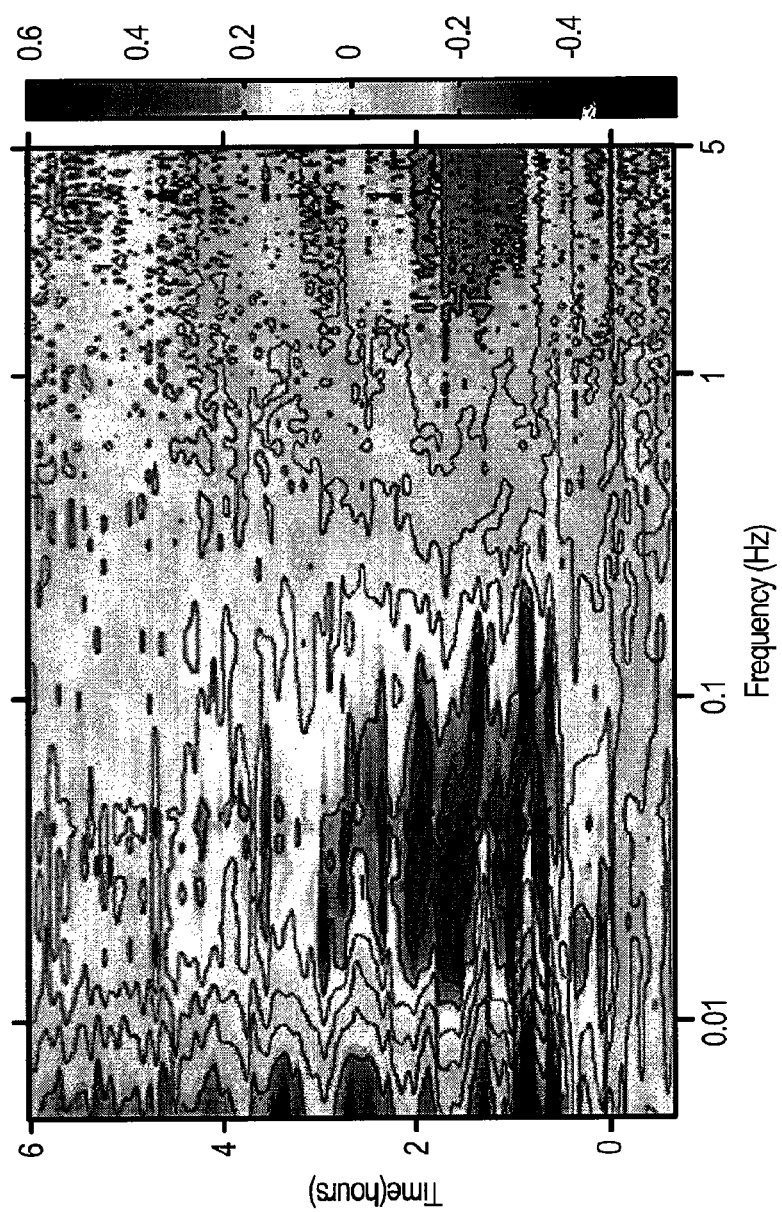

All cells run on ATP as their energy source. ATP can be generated in two ways: oxidative phosphorylation (electron transport in mitochondria) or anaerobic glycolysis. Certain metabolic drugs can shut down one or the other pathway. For instance, electron transport is shut down by KCN, while the anaerobic glycolysis is shut down by Iodoacetate. The spectrograms of these two drugs at 37° C. are shown in FIG. 36. FIG. 36(*a*) shows a motility contrast image and spectrogram of the shell for 10 μg/ml of iodoacetate, and FIG. 36(*b*) shows a motility contrast image and spectrogram of the shell for 20 μg/ml of KCN. For iodoacetate there is a strong increase for the high frequencies associated with organelle transport, possibly because of increased mitochondrial activity. KCN shows a weaker increase of higher frequencies. Iodoacetate has the interesting property that it induces oscillations in the mid-to-low frequency range, shown in FIG. 37. FIG. 37 shows spectrograms for the shell (left) and core (right) for 20 μg/ml of iodoacetate at 37° C.

Figure 38A:
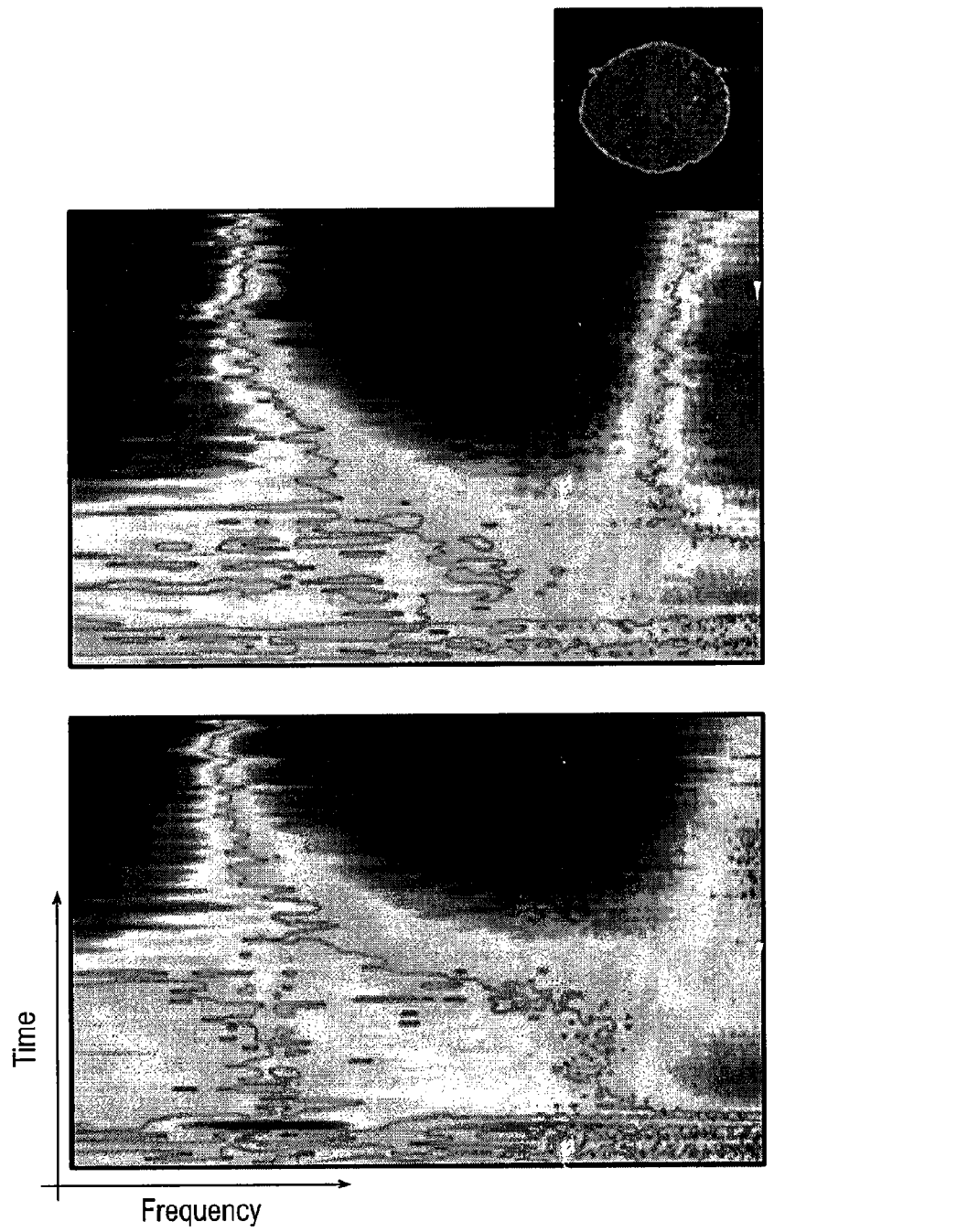
FIG. 38 shows a comparison of the core-shell for the drugs cytochalasin (anti-actin drug) (FIG. 38(a)) and KCN (anti electron transport) (FIG. 38(b)), where the enhanced organelle activity appears strongly only in the shell and not in the core.
Figure 38B:
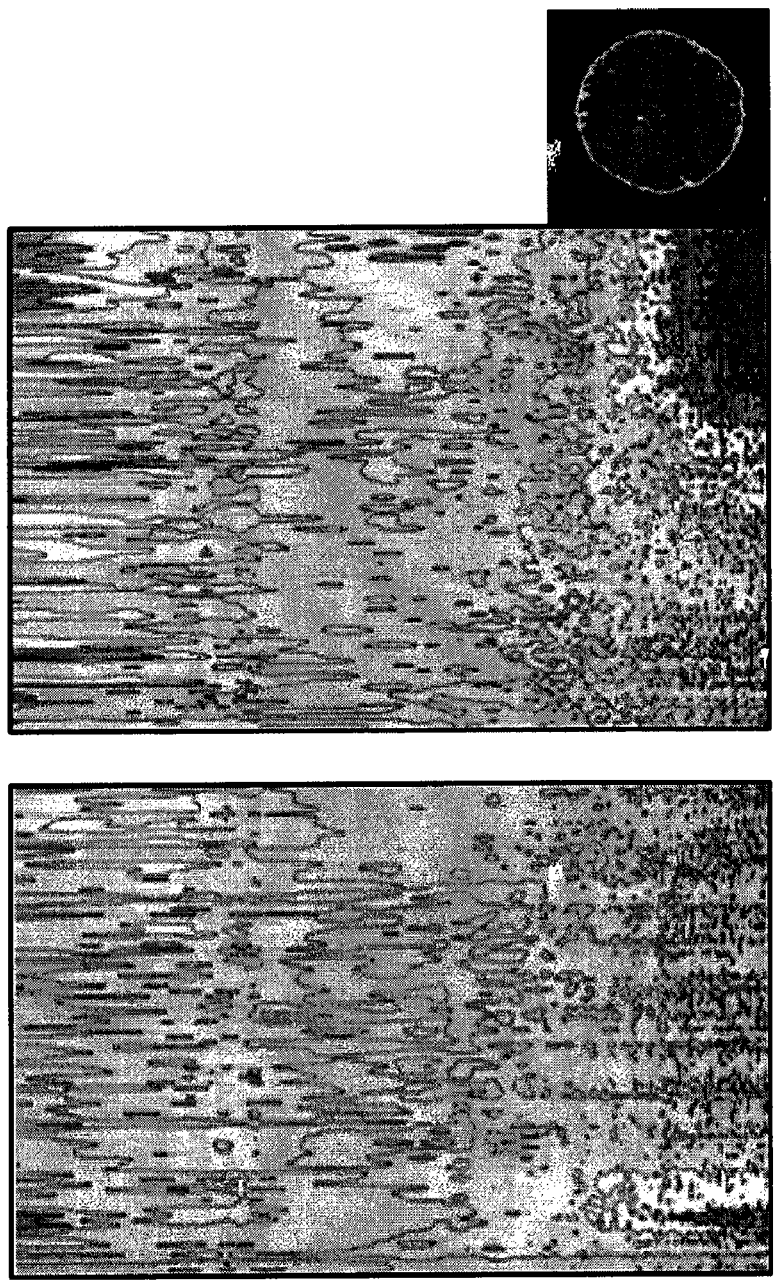

FIG. 38 shows a comparison of the core-shell for the drugs cytochalasin (anti-actin drug) and KCN (anti electron transport). FIG. 38(*a*) (left side) shows the results for cytochalasin and FIG. 38(*b*) (right side) shows the results for KCN. For each drug, the upper spectrogram is for the shell and the lower spectrogram is for the core. The high-frequency organelle activity appears only in the healthy shell and not in the core.

Spectrograms and Specificity

For drug screening applications, among the more important properties of an assay are specificity, sensitivity and dynamic range. Sensitivity defines the limit of detection, dynamic range defines how many orders of magnitude the response can vary between the lowest and the highest response, and specificity defines how specific the response is to the type of stimulus. Motion, collectively, is not highly specific, because there are so many contributions to motion. However, the spectrograms show which frequencies are affected, how rapidly they are affected, and how much they are affected. Therefore, a specific drug may have a specific signature in how it changes the different aspects of cellular motion.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A motility contrast imaging apparatus for imaging a tissue sample at a sample plane, the imaging apparatus comprising:
    an illumination source providing an illumination beam;
    a mirror positioned at the sample plane;
        a focusing element positioned wherein a first portion of the illumination beam is incident on the focusing element and a second portion of the illumination beam is not incident on the focusing element, the first portion of the illumination beam being focused by the focusing element on the mirror and thereby forming a reference beam, the second portion of the illumination beam being directed at the tissue sample and thereby forming a signal beam;
        a collecting element positioned to collect the reference beam after it has been reflected by the mirror and to collect the signal beam after it has been scattered by the tissue sample; and
        a detector for detecting the collected reflected reference beam and the collected scattered signal beam.

2. The motility contrast imaging apparatus of claim 1, further comprising a beam expander positioned to expand the illumination beam before the illumination beam is incident on the focusing element.

3. The motility contrast imaging apparatus of claim 2, wherein the beam expander is a cylindrical lens beam expander.

4. The motility contrast imaging apparatus of claim 1, wherein the focusing element is a lens.

5. The motility contrast imaging apparatus of claim 1, wherein the mirror is located in a well containing the tissue sample.

6. The motility contrast imaging apparatus of claim 1, wherein the collecting element is a Fourier-transform lens and the detector is located at the Fourier plane, the crossing angle between the reference beam and the signal beam at the detector providing a carrier frequency for digital holography.

7. The motility contrast imaging apparatus of claim 1, wherein the detector is a CCD chip.

8. A motility contrast imaging apparatus for imaging a tissue sample, the imaging apparatus comprising;
    an illumination source providing a signal beam and a reference beam;
    an opaque aperture mask having a signal opening, the signal beam being scattered by the tissue sample and then passing through the signal opening of the opaque aperture mask;
        a mirror located substantially adjacent laterally to the tissue sample, the reference beam being reflected by the mirror;
        a Fourier transform lens, the scattered signal beam passing through the Fourier transform lens;
        a prism adjacent laterally to the Fourier transform lens, the reflected reference beam being deflected by the prism to intersect an optical axis of the signal beam at the Fourier plane of the Fourier transform lens; and
        a detector located at the Fourier plane for detecting the scattered signal beam passing through the Fourier transform lens and the intersecting reference beam deflected by the prism.

9. The motility contrast imaging apparatus of claim 8, further comprising a polarizing beam splitter, the signal beam being deflected by the polarizing beam splitter and then backscattered by the tissue sample and the scattered signal beam passing through the polarizing beam splitter; the reference beam being deflected by the polarizing beam splitter and then reflected by the mirror and the reflected reference beam passing through the polarizing beam splitter; and a variable compensator tuned to compensate for path length differences traveled by the signal beam and the reference beam, at least one of the reference beam and the signal beam passing through the variable compensator.

10. The motility contrast imaging apparatus of claim 9, wherein the mirror is attached to the opaque aperture mask in advance of the tissue sample to thereby at least partially reduce for the difference between the distance traveled by the reference beam and relative to the distance traveled by the signal beam.

11. The motility contrast imaging apparatus of claim 10, wherein the tissue sample is on a plate tilted relative to the optical axis of the signal beam to prevent specular reflection.

12. The motility contrast imaging apparatus of claim 11, wherein the illumination source generates a Gaussian beam.

13. The motility contrast imaging apparatus of claim 8, wherein the mirror is laterally adjacent to the tissue sample and the opaque optical mask has a reference opening; the mirror and tissue sample being on one side of the opaque optical mask and the detector being on the opposite side of the opaque optical mask; the signal beam being side-scattered by the tissue sample and passing through the signal opening of the opaque optical mask towards the detector, and the mirror being positioned to reflect the reference beam through the reference opening of the opaque optical mask parallel to the signal beam towards the detector.

14. The motility contrast imaging apparatus of claim 8, further comprising a quarter wave plate located next to the opaque optical mask, the tissue sample and mirror being on one side of the quarter wave plate and the detector being on the opposite side of the quarter wave plate.

15. The motility contrast imaging apparatus of claim 9, wherein the variable compensator comprises a first dielectric plate placed in the signal path and a second dielectric plate placed in the reference path.

16. The motility contrast imaging apparatus of claim 9, wherein the variable compensator is tuned to define a depth gate within the tissue sample.

17. A motility contrast imaging apparatus for writing Fourier-domain holograms with speckle modulation from a tissue sample, the apparatus comprising:
- an illumination source for providing illumination pulses including a leading pulse and a trailing pulse;
- a focusing lens for focusing the illumination pulses in front of the tissue sample;
- a transparent coverslip covering the tissue sample whereby the illumination pulses must pass through the transparent cover slip to reach the tissue sample, the coverslip and tissue sample each comprising a separate target;
- a beam splitter for reflecting the illumination pulses, after the illumination pulses pass through the focusing lens, onto the targets and for passing through the return pulses;
- a Fourier transform lens for processing the return pulses; and
- a detector located at the Fourier plane of the Fourier transform lens for receiving the processed return pulses;
- wherein the illumination pulses are scattered by the tissue sample and are also reflected by the coverslip, and wherein one of the illumination pulses scattered by the tissue sample and the other one of the illumination pulses reflected by the coverslip coincidentally strike the detector to define a coherence-gated depth of the target showing interference at the detector.

18. The motility contrast imaging apparatus of claim 17, wherein the illumination source is a fiber-optic configuration with a variable delay.

19. The motility contrast imaging apparatus of claim 17, wherein the detector is a CCD array.

20. The motility contrast imaging apparatus of claim 1 wherein the focusing element is disposed off-axis relative to the optical axis of the illumination beam.

21. The motility contrast imaging apparatus of claim 1 wherein the signal beam is disposed off-axis relative to the optical axis of the illumination beam.

22. The motility contrast imaging apparatus of claim 1 wherein both the focusing element and the signal beam are disposed off-axis relative to the optical axis of the illumination beam and wherein the reference beam and the signal beam are collimated.

23. The motility contrast imaging apparatus of claim 1 wherein the collecting element is a single Fourier-transform lens that collects both the reflected reference beam and the scattered signal beam and wherein the crossing angle between the reference beam and the signal beam at the detector defines a digital holography carrier frequency.

24. The motility contrast imaging apparatus of claim 23 wherein the Fourier-transform lens defines an optical axis spaced from both the axis of the reflected reference beam and from the axis of the scattered signal beam.

25. The motility contrast imaging apparatus of claim 24 wherein the detector is positioned in the Fourier plane of the Fourier-transform lens.

26. The motility contrast imaging apparatus of claim 25 wherein the Fourier-transform lens is positioned between and equidistantly from the detection plane and the detector.

27. The motility contrast imaging apparatus of claim 13 wherein the mirror is positioned at a 45 degree angle relative to both the reference beam and the reflected reference beam.

28. The motility contrast imaging apparatus of claim 8 wherein the signal beam passes through the Fourier transform lens and strikes the detector without passing through the prism and wherein the reference beam passes through the prism and strikes the detector without passing through the Fourier transform lens.

29. The motility contrast imaging apparatus of claim 28 wherein the reference beam is an unfocused reference beam.

30. The motility contrast imaging apparatus of claim 17 wherein the delay between pulses is adjusted to identify speckles which are coherent with a selected depth.

31. The motility contrast imaging apparatus of claim 17 wherein the leading pulse scattered by the tissue sample and the trailing pulse reflected by the coverslip time coincidentally strike the detector.

* * * * *